United States Patent
Vankayalapati et al.

(10) Patent No.: US 12,275,738 B2
(45) Date of Patent: Apr. 15, 2025

(54) CDK9 INHIBITORS

(71) Applicant: Biolexis Therapeutics, Inc., Lehi, UT (US)

(72) Inventors: Hariprasad Vankayalapati, Sandy, UT (US); Zhaoliang Li, Salt Lake City, UT (US); Kyle Medley, American Fork, UT (US); Dongqing Yan, Salt Lake City, UT (US); David J. Bearss, Alpine, UT (US)

(73) Assignee: Biolexis Therapeutics, Inc., Lehi, UT (US)

( * ) Notice: Subject to any disclaimer, the term of this patent is extended or adjusted under 35 U.S.C. 154(b) by 0 days.

(21) Appl. No.: 18/296,930

(22) Filed: Apr. 6, 2023

(65) Prior Publication Data
US 2023/0322792 A1 Oct. 12, 2023

Related U.S. Application Data

(60) Provisional application No. 63/329,105, filed on Apr. 8, 2022.

(51) Int. Cl.
C07D 487/04 (2006.01)
A61P 35/00 (2006.01)

(52) U.S. Cl.
CPC ............ *C07D 487/04* (2013.01); *A61P 35/00* (2018.01)

(58) Field of Classification Search
CPC ................ C07D 487/04; A61P 35/00
See application file for complete search history.

(56) References Cited

U.S. PATENT DOCUMENTS

| | | |
|---|---|---|
| 5,033,252 A | 7/1991 | Carter |
| 5,052,558 A | 10/1991 | Carter |
| 5,323,907 A | 6/1994 | Kalvelage |
| 2005/0215569 A1 | 9/2005 | Atkinson et al. |
| 2013/0184285 A1 | 7/2013 | Brain et al. |
| 2017/0152269 A1 | 6/2017 | Li et al. |
| 2017/0173021 A1 | 6/2017 | Lowe et al. |
| 2020/0297704 A1 | 9/2020 | Yang et al. |
| 2020/0354350 A1 | 11/2020 | Chen et al. |
| 2021/0015819 A1 | 1/2021 | Heymach et al. |
| 2021/0275522 A1 | 9/2021 | Yang et al. |

FOREIGN PATENT DOCUMENTS

| | | |
|---|---|---|
| CN | 105111191 A | 12/2015 |
| WO | 2020/206035 A1 | 10/2020 |
| WO | WO-2020224568 A1 * | 11/2020 ........... A61K 31/506 |
| WO | 2021/236721 A1 | 11/2021 |
| WO | 2022/031587 A1 | 2/2022 |

OTHER PUBLICATIONS

Łukasik P, Załuski M, Gutowska I. Cyclin-Dependent Kinases (CDK) and Their Role in Diseases Development—Review. Int J Mol Sci. Mar. 13, 2021;22(6):2935. doi: 10.3390/ijms22062935. PMID: 33805800; PMCID: PMC7998717. (Year: 2021).*
Yin et al. A novel CDK9 inhibitor shows potent antitumor efficacy in preclinical hematologic tumor models. Mol Cancer Ther. Jun. 2014; 13(6):1442-56. doi: 10.1158/1535-7163.MCT-13-0849. Epub Mar. 31, 2014. PMID: 24688048. (Year: 2014).*
Cecil Textbook of Medicine, 1997, 20th Ed, Oncology (Year: 1997) (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022) (Year: 2022).*
Barlaam et al., "Discovery of AZD4573, a Potent and Selective Inhibitor of CDK9 That Enables Short Duration of Target Engagement for the Treatment of Hematological Malignancies," *Journal of Medicinal Chemistry* 63(24):15564-15590, Dec. 11, 2020.
Bundgaard, "Design of prodrugs: Bioreversible derivatives for various functional groups and chemical entities," in Bundgaard (ed.), *Design of Prodrugs*, Elsevier, Amsterdam, 1985. (3 pages).
Iacobucci et al., "Modeling and targeting of erythroleukemia by hematopoietic genome editing," *Blood* 137(12):1628-1640, Mar. 25, 2021.

(Continued)

*Primary Examiner* — Bruck Kifle
*Assistant Examiner* — Kevin S Martin
(74) *Attorney, Agent, or Firm* — Seed IP Law Group LLP

(57) ABSTRACT

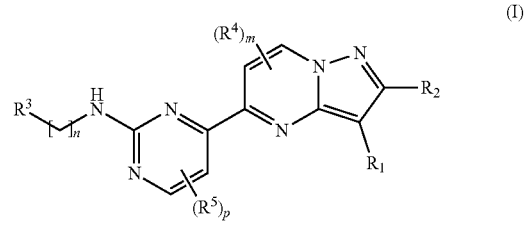

or a stereoisomer or salt (e.g., pharmaceutically acceptable salt) thereof, wherein $R^1$, $R^2$, $R^3$, $R^4$, $R^5$, p, m, and n are as defined herein. Use of the compounds as a component of a pharmaceutical compositions and methods for their use are also provided.

19 Claims, No Drawings

(56) References Cited

OTHER PUBLICATIONS

Ou et al., "CDK9 modulates circadian clock by attenuating REV-ERBα activity," *Biochemical and Biophysical Research Communications* 513:967-973, 2019.
Phillipson et al., "Discovery and SAR of novel pyrazolo[1,5-α]pyrimidines as inhibitors of CDK9," *Bioorganic & Medicinal Chemistry* 23(19):6280-6296, Oct. 1, 2015.
Yin et al., "A Novel CDK9 Inhibitor Shows Potent Antitumor Efficacy in Preclinical Hematologic Tumor Models," *Molecular Cancer Therapeutics* 13(6):1442-1456, Jun. 2014.
PubChem SID 396366457, Substance Record, Modify Date: Dec. 6, 2019. (4 pages).

\* cited by examiner

CDK9 INHIBITORS

STATEMENT REGARDING FEDERALLY SPONSORED RESEARCH OR DEVELOPMENT

Portions of the work described herein were made with government support under grant number W81XWH2110170 awarded by the United States Department of Defense. The government has certain rights in the invention.

BACKGROUND

Technical Field

The present disclosure generally relates to compounds that inhibit protein kinase activity such as cyclin-dependent protein kinases (CDKs), and to compositions and methods to treat cancers and other conditions that are associated with CDKs.

Description of the Related Art

Cyclin-dependent kinases (CDKs) are serine-threonine kinases that function to coordinate multiple cellular functions and phosphorylate substrates essential for progression through the cell cycle. Activity of specific CDKs at specific times is essential for both initiation and coordinated progress through the cell cycle. For example, CDK7, CDK8, and CDK9 play a role in regulating transcription to further influence cell proliferation and survival by driving the expression of numerous target genes. The relevance of CDKs to cancer growth and survival has garnered widespread interest in the generation of CDK inhibitors.

A great number of CDK9 inhibitors have been widely used in tumor cells to the rapid induction of apoptosis. However, a complex toxicity profile associated with activity beyond CDK9 has hampered development.

Therefore, there is a need for the rational design of specific and selective CDK9 inhibitors for the treatment of cancer and other conditions that are mediated and/or associated. The present disclosure fulfills these needs and offers other related advantages.

BRIEF SUMMARY

In brief, the present disclosure provides CDK9 inhibitor compounds, including stereoisomers or salts (e.g., pharmaceutically acceptable salts) thereof, which can be used alone or in combination with a pharmaceutically acceptable carrier. Methods for use of CDK9 inhibitor compounds for treatment of various diseases or conditions, such as bladder cancer, prostate cancer, and leukemia are also provided.

In one embodiment, compounds having the following Structure (I) are provided:

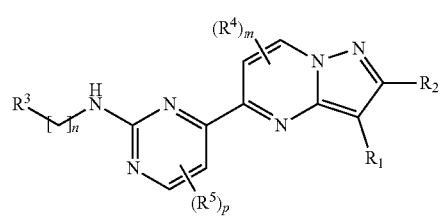

(I)

or a salt (e.g., pharmaceutically acceptable salt) or stereoisomer thereof, wherein $R^1$, $R^2$, $R^3$, $R^4$, $R^5$, p, m, and n are as defined herein. Use of the compounds as a component of a pharmaceutical compositions and methods for their use are also provided. Pharmaceutical compositions comprising one or more of the foregoing compounds of Structure (I) and a therapeutic agent are also provided.

In other embodiments, the present disclosure provides a method for administering a therapeutic agent to a patient in need thereof, the method comprising preparing a composition comprising the compound of Structure (I) and a therapeutic agent and delivering the composition to the patient.

These and other aspects of the disclosure will be apparent upon reference to the following detailed description.

DETAILED DESCRIPTION

In the following description, certain specific details are set forth in order to provide a thorough understanding of various embodiments of the disclosure. However, one skilled in the art will understand that embodiments of the disclosure may be practiced without these details. As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to."

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs. As used in the specification and claims, the singular form "a," "an" and "the" include plural references unless the context clearly dictates otherwise.

"Hydroxy" or "hydroxyl" refers to an —OH radical.

"Amino" refers to an —NH$_2$ radical.

"Cyano" refers to a —CN radical.

"Alkyl" refers to a saturated straight or branched hydrocarbon chain radical consisting solely of carbon and hydrogen atoms having from one to six carbon atoms ($C_1$-$C_6$ alkyl), which is attached to the rest of the molecule by a single bond. Hydrocarbon chain radicals include, for example, methyl, ethyl, n-propyl, 1 methylethyl (iso-propyl), n-butyl, n-pentyl, 1,1 dimethylethyl (t-butyl), iso-pentyl, n-hexyl, and the like. Unless stated otherwise specifically in the specification, an alkyl group is optionally substituted.

"Cycloalkyl" refers to a saturated cyclic hydrocarbon radical having from three to eight carbon atoms ($C_3$-$C_8$ cycloalkyl) attached to the rest of the molecule by a single bond. Saturated cyclic hydrocarbon radicals include, for example, cyclopropyl, cyclobutyl, cyclopentyl or cyclohexyl. Unless otherwise stated specifically in the specification, a cycloalkyl group is optionally substituted.

"Halo" refers to fluoro, chloro, bromo, or iodo. Halo belongs to group 17 of the periodic table.

"Alkoxy" refers to a radical of the formula —OR$_a$ where R$_a$ is an alkyl radical as defined above containing one to twelve carbon atoms ($C_1$-$C_{12}$ alkoxy), one to eight carbon atoms ($C_1$-$C_8$ alkoxy) or one to six carbon atoms ($C_1$-$C_6$ alkoxy), or any value within these ranges. Unless stated otherwise specifically in the specification, an alkoxy group is optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Haloalkoxy" refers to a radical having the following formula: —Ohaloalkyl, wherein haloalkyl is as defined above. Unless otherwise stated specifically in the specification, a haloalkoxy group is optionally substituted.

"Hydroxylalkyl" or "hydroxyalkyl" refers to an alkyl radical, as defined above that is substituted by one or more hydroxyl radical. The hydroxyalkyl radical is joined at the main chain through the alkyl carbon atom. Unless stated otherwise specifically in the specification, a hydroxyalkyl group is optionally substituted.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. When substituted, the aryl group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. In some embodiments, a heterocyclyl is saturated (i.e., contains no double or triple bonds). Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"Heteroaryl" refers to a 5- to 18-membered, for example 5- to 6-membered, ring system radical comprising one to thirteen ring carbon atoms, one to six ring heteroatoms selected from the group consisting of nitrogen, oxygen and sulfur, and at least one aromatic ring. Heteroaryl radicals may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

The term "substituted" used herein means any of the above groups (e.g., alkyl, cycloalkyl, haloalkyl, alkoxy, hydroxyalkyl, or heterocyclyl) wherein at least one hydrogen atom is replaced by a bond to a non-hydrogen atoms such as, but not limited to: a halogen atom such as F, Cl, Br, and I; oxo groups (=O); hydroxyl groups (—OH); alkoxy groups (—OR$^a$, where R$^a$ is $C_1$-$C_{12}$ alkyl or cycloalkyl); carboxyl groups (—OC(=O)R$^a$ or —C(=O)OR$^a$, where R$^a$ is H, $C_1$-$C_{12}$ alkyl or cycloalkyl); amine groups (—NR$^a$R$^b$, where R$^a$ and R$^b$ are each independently H, $C_1$-$C_{12}$ alkyl or cycloalkyl); $C_1$-$C_{12}$ alkyl groups; and cycloalkyl groups. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group. In other embodiments, the substituent is a carboxyl group. In other embodiments, the substituent is an amine group.

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" indicates a compound that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof but is converted in vivo to an active compound of the disclosure. Prodrugs are typically rapidly transformed in vivo to yield the parent compound of the disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the disclosure in vivo when such prodrug is administered to a mammalian subject. Prodrugs of a compound of the disclosure may be prepared by modifying functional groups present in the compound of the disclosure in such a way that the modifications are cleaved, either in routine manipulation or in vivo, to the parent compound of the disclosure. Prodrugs include compounds of the disclosure wherein a hydroxy, amino, or mercapto group is bonded to any group that, when the prodrug of the compound of the disclosure is administered to a mammalian subject, cleaves to form a free hydroxy, free amino or free mercapto group, respectively. Examples of prodrugs include, but are not limited to, acetate, formate, and benzoate derivatives of alcohol or amide derivatives of amine functional groups in the compounds of the disclosure and the like.

The embodiments disclosed herein is also meant to encompass all pharmaceutically acceptable compounds of the compound of Structure (I) being isotopically labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically labelled compounds of Structure (I), for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically labeled compounds of Structure (I) can generally be prepared by conventional techniques known to those skilled in the art or by processes analogous to those described in the Preparations and Examples as set out below using an appropriate isotopically-labeled reagent in place of the non-labeled reagent previously employed.

The embodiments disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid (TFA), undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the disclosure which, when administered to a mammal, preferably a human, is sufficient to effect treatment in the mammal, preferably a human. The amount of a lipid nanoparticle of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Protein kinase-mediated condition" or "disease," as used herein, refers to any disease or other deleterious condition in which a protein kinase is known to play a role and that are alleviated by treatment with a protein kinase inhibitor. In certain embodiments, the cancer is a cancer of colon, breast, stomach, prostate, pancreas, or ovarian tissue.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their salt (e.g., pharmaceutically acceptable salt), may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. The present disclosure also contemplates "diastereomers", which refers to non-mirror image of non-identical stereoisomers. Diastereomers occur when two or more stereoisomers of a compound have different configurations at one or more of the equivalent stereocenters and are not mirror images of each other.

A "tautomer" refers to a proton shift from one atom of a molecule to another atom of the same molecule. The present disclosure includes tautomers of any said compounds.

Compounds

In an aspect, the present disclosure provides CDK9 inhibitor compounds, including stereoisomers or salts (e.g., pharmaceutically acceptable salts) thereof, which can be used alone or in combination with a pharmaceutically acceptable carrier. Methods for use of CDK9 inhibitor compounds for treatment of various diseases or conditions, such as bladder cancer, prostate cancer, and leukemia are also provided.

In one embodiment, the compounds have the following Structure (I):

(I)

or a stereoisomer or salt thereof, wherein:
- $R^1$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- $R^2$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- $R^3$ is $C_3$-$C_8$ cycloalkyl or 3-10 membered heterocyclyl;
- each occurrence of $R^4$ is independently halo, hydroxy, cyano, amino, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- m is 0, 1, or 2; and
- n is 0, 1, 2, 3, or 4,
- wherein each of $R^1$, $R^2$, $R^3$ and $R^4$ is optionally substituted with one or more substituent. For example, in some embodiments, each $C_1$-$C_6$ alkyl, $C_3$-$C_8$ cycloalkyl, $C_1$-$C_6$ haloalkyl, $C_1$-$C_6$ alkoxy, $C_1$-$C_6$ hydroxyalkyl, and 3-10 membered heterocyclyl is optionally substituted.

One embodiment provides a compound having the following Structure (I):

(I)

or a stereoisomer or salt thereof, wherein:
- $R^1$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- $R^2$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- $R^3$ is $C_3$-$C_8$ cycloalkyl or 3-10 membered heterocyclyl;
- each occurrence of $R^4$ and $R^5$ are independently halo, hydroxy, cyano, amino, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- m is 0, 1, or 2;
- n is 0, 1, 2, 3, or 4; and
- p is 0, 1, or 2,
- wherein each $R^1$, $R^2$, $R^3$, $R^4$, and $R^5$ is optionally substituted with one or more substituents.

Another embodiment provides a compound having the following Structure (I):

(I)

or a stereoisomer or salt thereof, wherein:
- $R^1$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- $R^2$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- $R^3$ is $C_3$-$C_8$ cycloalkyl or 3-10 membered heterocyclyl;
- each occurrence of $R^4$ and $R^5$ are independently halo, hydroxy, cyano, amino, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
- m is 0, 1, or 2;
- n is 0, 1, 2, 3, or 4; and
- p is 0, 1, or 2,
- wherein each $R^1$, $R^2$, $R^3$, $R^4$, and $R^5$ (e.g., alkyl, cycloalkyl, haloalkyl, alkoxy, hydroxyalkyl, or heterocyclyl) is optionally substituted with one or more substituents selected from the group consisting of $C_1$-$C_{12}$alkyl, $C_3$-$C_{12}$cycloalkyl, halo, oxo, hydroxy, cyano, alkoxy, —C(=O)OR$^a$, and —NR$^b$R$^c$, wherein:
- each occurrence of R$^a$ is independently hydrogen, $C_1$-$C_{12}$ alkyl, or cycloalkyl; each occurrence of R$^a$ and R$^b$ are each independently hydrogen, $C_1$-$C_{12}$ alkyl, $C_3$-$C_{12}$ cycloalkyl, —C(=O)alkyl (e.g., —C(=O)—$C_1$-$C_{12}$ alkyl), 3-10 membered heterocyclyl, or 3-10 membered heteroaryl.

In some embodiments, $R^1$ is hydrogen, $C_1$-$C_6$ alkyl, or $C_3$-$C_8$ cycloalkyl. In certain embodiments, $R^1$ is hydrogen, cyclopropyl, cyclobutyl, cyclopentyl, cyclohexyl, isopropyl, methyl, or ethyl. In some embodiments, $R^1$ is hydrogen, cyclopropyl, cyclobutyl, isopropyl, or methyl. In certain embodiments, $R^1$ is unsubstituted.

In some embodiments, $R^2$ is hydrogen or $C_1$-$C_6$ alkyl. In certain embodiments, $R^2$ is $C_1$-$C_6$ alkyl. In some embodiments, $R^2$ is —CH$_3$. In some other embodiments, $R^2$ is hydrogen. In some embodiments, $R^2$ is unsubstituted.

In certain embodiments, at least one of $R^1$ or $R^2$ is hydrogen. In certain embodiments, both of $R^1$ and $R^2$ are hydrogen.

In some embodiments, n is 0 or 1. In certain embodiments, n is 2, 3, or 4. In some embodiments, n is 1. In certain embodiments, n is 0.

In some embodiments, $R^3$ is $C_3$-$C_8$ cycloalkyl. In certain embodiments, $R^3$ is $C_5$-$C_6$cycloalkyl. In some embodiments, $R^3$ is 3-10 membered heterocyclyl. In certain embodiments, $R^3$ is 5-6 membered heterocyclyl. In some embodiments, $R^3$ is substituted.

In some embodiments, $R^3$ is substituted with one or more substituents selected from the group consisting of hydroxy, amino, cyano, halo, $C_1$-$C_6$ alkyl, $C_3$-$C_8$ cycloalkyl, $C_1$-$C_6$ haloalkyl, or —N(R$^{3b}$)R$^{3a}$, wherein R$^{3a}$ is 3-10 membered heterocyclyl or 3-10 membered heteroaryl and R$^{31}$ is hydrogen or $C_1$-$C_6$ alkyl.

In some embodiments, $R^3$ is substituted with one or more substituents selected from the group consisting of hydroxy, amino, cyano, halo, $C_1$-$C_6$ alkyl, $C_3$-$C_8$ cycloalkyl, $C_1$-$C_6$ haloalkyl, or —N($R^{3b}$)$R^{3a}$, wherein $R^{3a}$ is —C(=O)alkyl, 3-10 membered heterocyclyl or 3-10 membered heteroaryl and $R^{3b}$ is hydrogen or $C_1$-$C_6$ alkyl.

In some embodiments, $R^3$ is substituted with one or more substituents selected from the group consisting of hydroxyl, amino, or —N(H)$R^{3c}$, wherein $R^{3c}$ is 5-6 membered heterocyclyl.

In some embodiments, $R^3$ is substituted with one or more substituents selected from the group consisting of hydroxyl, amino, or —N(H)$R^{3c}$, wherein $R^{3c}$ is —C(=O)CH$_3$, or 5-6 membered heterocyclyl.

In some other embodiments, $R^3$ is unsubstituted.

In some embodiments, $R^3$ has one of the following structures:

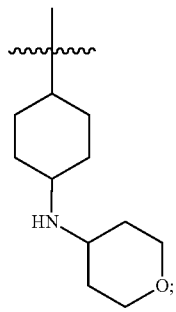

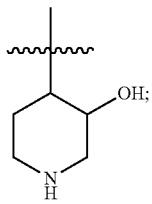

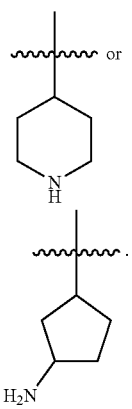

In certain embodiments, $R^3$ has one of the following structures:

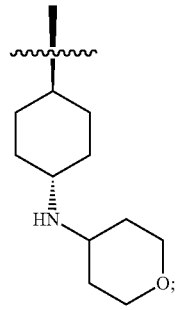

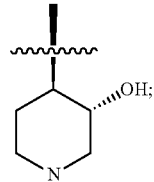

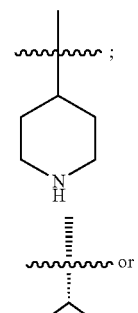

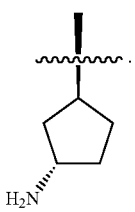

In some embodiments, $R^3$ has one of the following structures:

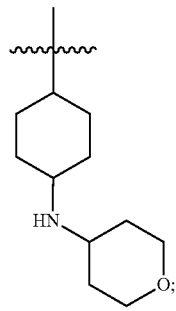

-continued
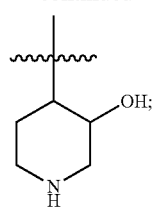
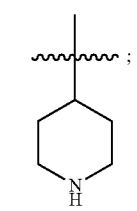
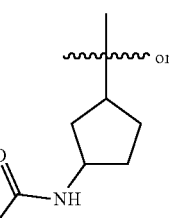
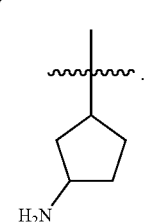
In certain embodiments, R³ has one of the following structures:
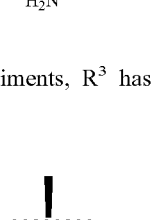
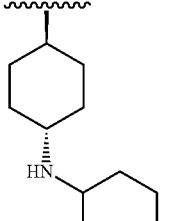
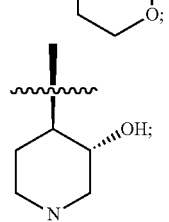
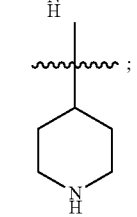
-continued
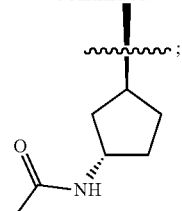
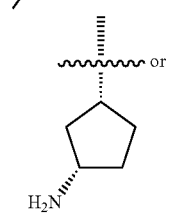
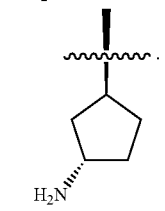
In some embodiments, R³ has the following structure:
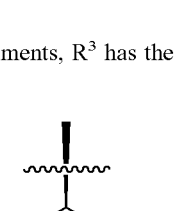
In certain embodiments, R³ has the following structure:
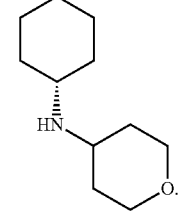
In some embodiments, R³ has the following structure:
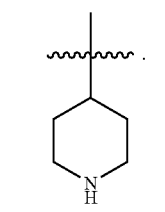

In certain embodiments, R³ has the following structure:

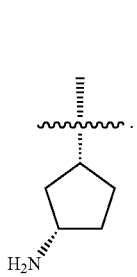

In some embodiments, R³ has the following structure:

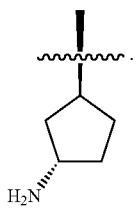

In some embodiments, R³ has the following structure:

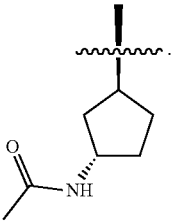

In certain embodiments, m is 1 or 2. In some embodiments, m is 0. In some embodiments, m is 0 or 1. In certain embodiments, each occurrence of R⁴ is halo. In some embodiments, each occurrence of R⁴ is independently fluoro, chloro, or bromo. In some embodiments, each occurrence of R⁴ is fluoro.

In some embodiments, p is 0. In some embodiments, p is 1 or 2. In some embodiments, p is 1 and R⁵ is halo. In certain embodiments, p is 1 and R⁵ is chloro. In some embodiments, R⁵ is 2 and each occurrence of R⁵ is chloro.

In some embodiments, the compound is a free base form. In certain embodiments, the compound is a pharmaceutically acceptable salt. In some embodiments, the compound is a trifluoroacetic acid salt. In some embodiments, the compound is a hydrochloric acid salt. In some embodiments, the compound is a formic acid salt. In certain embodiments, the compound is a tautomer.

In various different embodiments, the compound has one of the structures set forth in Table 1 below (or a stereoisomer or salt thereof).

TABLE 1

Representative compounds of Structure (I)

| No. | Compound | Name | Mol. Wt. | IC50 (μM) |
|---|---|---|---|---|
| I-1 | 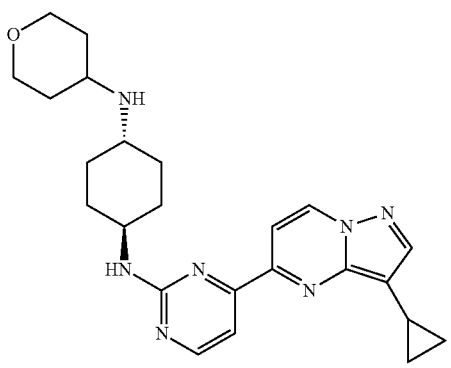 [SMILES: c1cc(-c2ccn3ncc(C4CC4)c3n2)nc(N[C@H]2CC[C@H](NC3CCOCC3)CC2)n1] | trans-N¹-[4-[(3-cyclopropyl)pyrazolo[1,5-a]pyrimidin-5-yl]pyrimidin-2-yl]-N4-(tetrahydro-2H-pyran-4-yl)cyclohexane-1,4-diamine | 433.56 | ++ |

TABLE 1-continued

Representative compounds of Structure (I)

| No. | Compound | Name | Mol. Wt. | IC50 (μM) |
|---|---|---|---|---|
| I-2 | | trans-N$^1$-[4-[(3-cyclobutyl)pyrazolo[1,5-a]pyrimidin-5-yl]pyrimidin-2-yl]- 24-(tetrahydro-2H-pyran-4-yl)cyclohexane-1,4-diamine | 447.59 | ++ |
| I-3 | | trans-N$^1$-[4-[(3-isopropyl)pyrazolo[1,5-a]pyrimidin-5-yl]pyrimidin-2-yl]- N4_(tetrahydro-2H-pyran-4-yl)cyclohexane-1,4-diamine | 435.58 | +++ |
| I-4 | | trans-5-[2-(3-hydroxypiperidin-4-yl)methylamino-pyrimidin-4-yl]-3-cyclopropyl pyrazolo[1, 5-a]pyrimidine | 365.44 | +++ |
| I-5† | | trans-5-[2-(3-hydroxypiperidin-4-yl)methylamino-pyrimidin-4-yl]-3-cyclobutyl pyrazolo[1, 5-a]pyrimidine | 607.51 | ++ |
| I-6† | | trans-5-[2-(3-hydroxypiperidin-4-yl)methylamino-pyrimidin-4-yl]-3-isopropylpyrazolo[1, 5-a]pyrimidine | 595.50 | +++ |

TABLE 1-continued

Representative compounds of Structure (I)

| No. | Compound | Name | Mol. Wt. | IC50 (μM) |
|---|---|---|---|---|
| I-7† | | trans-5-[2-(3-hydroxypiperidin-4-yl)methylamino pyrimidin-4-yl]pyrazolo[1,5-a]pyrimidine | 553.42 | ++ |
| I-8† | | trans-5-[2-(piperidin-4-yl)aminopyrimidin-4-yl]pyrazolo[1,5-a]pyrimidine | 523.40 | ++ |
| I-9† | | (1S,3R)-[3-[4-[pyrazolo[1,5-a]pyrimidin-5-yl]pyrimidin-2-yl]aminocyclopentan-1-yl]-1,3-diamine | 523.40 | +++ |
| I-10† | | trans-$N^1$-[4-[pyrazolo[1,5-a]pyrimidin-5-yl]pyrimidin-2-yl]-$N^4$-(tetrahydro-2H-pyran-4-yl)cyclohexane-1,4-diamine | 621.54 | ++ |
| I-11† | | (1S,3S)-[3-[4-[pyrazolo[1,5-a]pyrimidin-5-yl]pyrimidin-2-yl]aminocyclopentan-1-yl]-1,3-diamine | 523.40 | +++ |
| I-12† | | (1S,3S)-[3-[4-[3-methylpyrazolo[1,5-a]pyrimidin-5-yl]pyrimidin-2-yl]aminocyclopentan-1-yl]-1,3-diamine | 537.42 | +++ |
| I-13† | | (1S,3S)-[3-[4-[2-methylpyrazolo[1,5-a]pyrimidin-5-yl]pyrimidin-2-yl]aminocyclopentan-1-yl]-1,3-diamine | 537.42 | + |

TABLE 1-continued

Representative compounds of Structure (I)

| No. | Compound | Name | Mol. Wt. | IC50 (μM) |
|---|---|---|---|---|
| I-14† | | (1S,3S)-[3-[4-[3-isopropylpyrazolo[1,5-a]pyrimidin-5-yl]pyrimidin-2-yl]aminocyclopentan-1-yl]-1,3-diamine | 565.48 | +++ |
| I-15† | | (1S,3S)-[3-[4-[3-cyclopropyl pyrazolo[1,5-a]pyrimidin-5-yl]pyrimidin-2-yl]aminocyclopentan-1-yl]-1,3-diamine | 563.46 | — |
| I-16† | | (1S,3S)-[3-[4-[3-cyclobutylpyrazolo[1,5-a]pyrimidin-5-yl]pyrimidin-2-yl]aminocyclopentan-1-yl]-1,3-diamine | 577.49 | — |
| I-17 | | N-((1S,3S)-3-((4-(pyrazolo[1,5-a]pyrimidin-5-yl)pyrimidin-2-yl)amino)cyclopentyl)acetamide | 337.39 | — |
| I-18‡ | | (1S,3S)-N1-(5-chloro-4-(pyrazolo[1,5-a]pyrimidin-5-yl)pyrimidin-2-yl)cyclopentane-1,3-diamine | 366.25 | — |
| I-19# | | (1S,3S)-N1-(4-(pyrazolo[1,5-a]pyrimidin-5-yl)pyrimidin-2-yl)cyclopentane-1,3-diamine | | — |

†Also obtained as a trifluoroacetic acid salt
‡Also obtained as a hydrochloric acid salt
Also obtained as a formic acid salt
$IC_{50}$ values:
+++ represents a value below 1 μM
++ represents a value above 1 μM and below 5 μM
+ represents a value above 5 μM and below 10 μM It is understood that any embodiment of the compounds of Structure (I) as set forth above, and any specific substituent and/or variable in the compound of Structure (I) as set forth above may be independently combined with other embodiments and/or substituents and/or variables of compounds of Structure (I) to form embodiments of the disclosure not specifically set forth above. In addition, in the event that a list of substituents and/or variables is listed for any particular R group or variables n or m in a particular embodiment and/or claim, it is understood that each individual substituent and/or variable may be deleted from the particular embodiment and/or claim and that the remaining list of substituents and/or variables will be considered to be within the scope of the disclosure. It is understood that in the present description, combinations of substituents and/or variables of the depicted formulae are permissible only if such contributions result in stable compounds.

Pharmaceutical Compositions

Other embodiments are directed to pharmaceutical compositions. The pharmaceutical composition comprises anyone (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long-acting formulations are administered by implantation (for example subcutaneously or intramuscularly) or by intramuscular injection. Furthermore, in other embodiments, the compound is delivered in a targeted drug delivery system, for example, in a liposome coated with and organ specific antibody. In such embodiments, the liposomes are targeted to and taken up selectively by the organ. In yet other embodiments, the compound as described herein is provided in the form of a rapid release formulation, in the form of an extended-release formulation, or in the form of an intermediate release formulation. In yet other embodiments, the compound described herein is administered topically.

In treatment methods according to embodiments of the disclosure, an effective amount of at least one compound of Structure (I) is administered to a subject suffering from or diagnosed as having such a disease, disorder, or medical condition. Effective amounts or doses may be ascertained by methods such as modeling, dose escalation studies or clinical trials, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The compounds according to the disclosure are effective over a wide dosage range. For example, in the treatment of adult humans, dosages from 10 to 5000 mg, from 100 to 5000 mg, from 1000 mg to 4000 mg per day, and from 1000 to 3000 mg per day are examples of dosages that are used in some embodiments. The exact dosage will depend upon the route of administration, the form in which the compound is administered, the subject to be treated, the body weight of the subject to be treated, and the preference and experience of the attending physician.

In some embodiments, compounds of the disclosure are administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, compounds of the disclosure are administered in multiple doses. In some embodiments, dosing is about once, twice, three times, four times, five times, six times, or more than six times per day. In other embodiments, dosing is about once a month, once every two weeks, once a week, or once every other day. In another embodiment compounds of the disclosure and another agent (e.g., anti-cancer agent) are administered together about once per day to about 6 times per day. In another embodiment the administration of compounds of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of compounds of the disclosure may continue as long as necessary. In some embodiments, compounds of the disclosure are administered for more than 1, 2, 3, 4, 5, 6, 7, 14, or 28 days. In some embodiments, compounds of the disclosure are administered for less than 28, 14, 7, 6, 5, 4, 3, 2, or 1 day. In some embodiments, compounds of the disclosure are administered chronically on an ongoing basis, e.g., for the treatment of chronic effects.

In some embodiments, the compounds of the disclosure are administered in individual dosage forms. It is known in the art that due to inter-subject variability in compound pharmacokinetics, individualization of dosing regimen is necessary for optimal therapy.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the disclosed compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising one or more compounds of Structure (I), and a pharmaceutically acceptable carrier.

Provided herein are pharmaceutical compositions comprising one or more compounds selected from compounds of Structure (I) and pharmaceutically acceptable diluent(s), excipient(s), and carrier(s). In certain embodiments, the compounds described are administered as pharmaceutical compositions in which one or more compounds selected from compounds of Structure (I) are mixed with other active ingredients, as in combination therapy. Encompassed herein are all combinations of actives set forth in the combination therapies section below and throughout this disclosure. In specific embodiments, the pharmaceutical compositions include one or more compounds of Structure (I).

A pharmaceutical composition, as used herein, refers to a mixture of one or more compounds selected from compounds of Structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, therapeutically effective amounts of one or more compounds selected from compounds of Structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds selected from compounds of Structure (I) are formulated in aqueous solutions. In specific embodiments, the aqueous solution is selected from, by way of example only, a physiologically compatible buffer, such as Hank's solution, Ringer's solution, or physiological saline buffer. In other embodiments, one or more compounds selected from compounds of Structure (I) are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds described herein are formulated for parental injection, including formulations suitable for bolus injection or continuous infusion. In specific embodiments, formulations for injection are presented in unit dosage form (e.g., in ampoules) or in multi dose containers. Preservatives are, optionally, added to the injection formulations. In still other embodiments, the pharmaceutical compositions are formulated in a form suitable for parenteral injection as sterile suspensions, solutions, or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water soluble form. In additional embodiments, suspensions of one or more compounds selected from compounds of Structure (I) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions include at least one pharmaceutically acceptable carrier, diluent or excipient, and one or more compounds selected from compounds of Structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass un-solvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical compositions comprising one or more compounds selected from compounds of Structure (I) illustratively takes the form of a liquid where the agents are present in solution, in suspension or both. Typically, when the composition is administered as a suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of one or more compounds selected from compounds of Structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained release system, such as semipermeable matrices of solid hydrophobic polymers containing the therapeutic agent. Various sustained release materials are useful herein. In some embodiments, sustained release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds selected from compounds of Structure (I) provided in the pharmaceutical compositions of the present disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds selected from compounds of Structure (I) provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the amount the one or more compounds selected from compounds of Structure (I) provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds selected from compounds of Structure (I) provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Packaging materials for use in packaging pharmaceutical compositions described herein include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. In some embodiments, the pack or dispenser device is accompanied by instructions for administration. In certain embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

One embodiment provides a method of treating neuroendocrine prostate cancer (NEPC). Some embodiments provide a method for treating overexpression of N-MYC or MCL-1. Some embodiments provide a method of treating metastatic castration-resistant prostate cancers, or CRPCs. In some embodiments the disorder or disease includes treatment of a tumor with drug resistance. In some embodiments, the NEPC arises from prostate adenocarcinoma, androgen deprivation therapy (ADT), or abnormal expression and activation of various kinases. Some embodiments provide a method for treating hematological tumors or solid tumors.

In some embodiments, the method includes inhibiting or silencing pCDK9, pSer2, P-TEFb, MYC oncogene transcriptional activity, or suppression of active super-enhancer complex.

In some embodiments, the method includes promoting prostate cancer cell death and overcoming drug resistance (e.g., chemotherapeutic resistance and other current targeted therapeutics).

In certain embodiments, the method includes inhibiting CDK9, N-MYC, C-MYC, and its associated super-enhancer genes expression profile. In some embodiments, the method includes increasing the (median) survival time to greater than 12, 13, 13.5, 13.6, 13.7, 14, 18, 20 or 36 months. In some embodiments, the method further comprises administering a compound of Structure (I) in combination with another chemotherapeutic (e.g., docetaxel, abiraterone, enzalutamide).

In some embodiments, the method includes inhibiting CDK9 as a treatment for prostate tumors. In some embodiments, the method includes increasing prostate cancer cell death and overcoming the resistance due to chemo- and current targeted therapeutics. In some embodiments, the method includes inhibiting the CDK9-cyclin T complex, which phosphorylates the negative elongation factor (NELF) complex, DRB-sensitivity inducing factor (DSIF), and the Ser2 of the CTD of RNAPII, thereby affecting the removal of elongation blocks.

In some embodiments, the method includes reversibly binding to and inhibiting CDK9. In some embodiments, the method includes treating malignant prostate cancer cells, especially those of the CRPC, mCRPC, NEPC and treatment-resistant subtype origin, while also demonstrating no toxicity to normal prostate cells. In some embodiments, the method includes modulating N-MYC, C-MYC and MCL-1 transcription (e.g., in NEPC cells such as 22RV1, LASCPC-01, C4-2 and C4-2B from prostate cancer patients). In certain embodiments, the method includes orally administering compound of Structure (I). In some embodiments, the method includes globally modulating transcription, silencing, and inhibiting CDK9. In some embodiments, the method includes dually inhibiting CDK9, MYC, and associated super-enhancer genes. In some embodiments, the method includes inhibiting tumor growth.

In certain embodiments, the method includes binding or targeting residues within the CDK9 ATP binding site, for example, gate keeper Phe103, hinge residues Asp104, Phe105, Cys106 and DFG loop (167, 168, 169 residues) including back pocket K48 and sugar binding pockets residues Glu107, His108 and Asp109.

As mentioned above, the compounds and compositions of the disclosure will find utility in a broad range of diseases and conditions mediated by protein kinases, including diseases and conditions mediated by kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, a pharmaceutical composition has a compound described above and a pharmaceutically acceptable carrier including, for example, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In some embodiments, a method treating a disease or disorder, the method includes administering an effective amount of the compound or the pharmaceutical composition described herein to a subject in need thereof.

In some embodiments, the disease or disorder is a kinase-expressing cancer. In some specific embodiments, the cancer is bladder cancer. In some other specific embodiments, the cancer is prostate cancer. In some other specific embodiments, the cancer is a hematological malignancy such as acute myeloid leukemia. In some other specific embodiments, the disease or disorder is an autoimmune or inflammatory disease.

Preparation of Compounds

Preparation methods for the above compounds and compositions are described herein below and/or known in the art. It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the disclosure.

Furthermore, all compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

The following Reaction Scheme illustrates methods to make compounds of this disclosure, i.e., compounds of Structure (I):

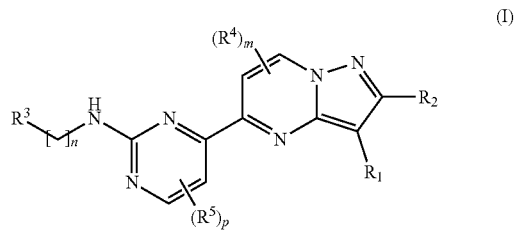

or a salt (e.g., pharmaceutically acceptable salt) or stereoisomer thereof, wherein $R^1$, $R^2$, $R^3$, $R^4$, $R^5$, p, m, and n are as defined herein. It is understood that one skilled in the art may be able to make these compounds by similar methods or by combining other methods known to one skilled in the art. It is also understood that one skilled in the art would be able to make, in a similar manner as described below, other compounds of Structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this disclosure.

The following examples are provided for purpose of illustration and not limitation.

Abbreviations

° C. (degree Celsius); $^1$H NMR (proton Nuclear Magnetic Resonance); DCM (dichloromethane); DMSO (dimethylsulfoxide); eq (equivalent); EtOAc (ethyl acetate); g (gram); h (hour); MeOH (methanol); mg (milligram); min (minute); mL (milliliter); mmol (millimole); TFA (trifluoroacetic acid); THF (tetrahydrofuran); TLC (Thin Layer Chromatography); LDA (lithium diisopropylamide); AcOH (acetic acid); mCPBA (3-chloroperbenzoic acid).

Example 1

Synthesis of Compound 1-1

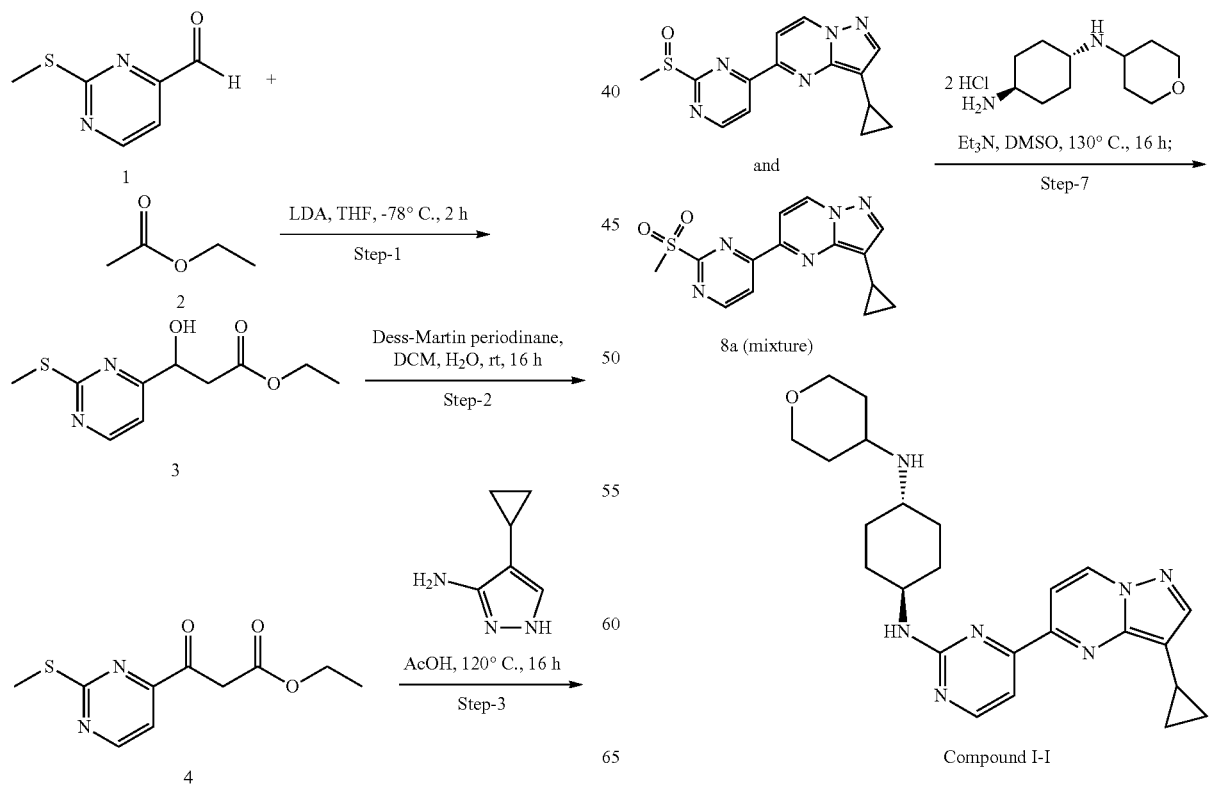

Synthesis of 3-hydroxy-3-(2-methylsulfanylpyrimidin-4-yl)propanoic acid ethyl ester (3)

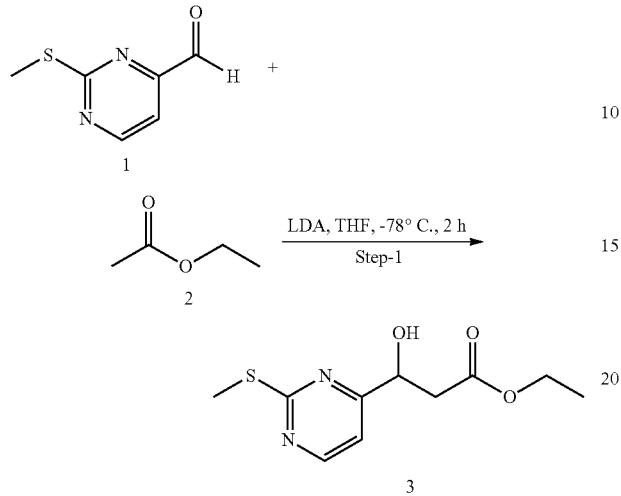

To a stirred solution of lithium diisopropylamide (LDA, 2M in THF/heptane/ethylbenzene) (2.25 mL, 4.5 mmol, 1.5 eq) in THF (10 mL) at −78° C. was added ethyl acetate (2) (793 mg, 9.0 mmol, 3.0 eq). The mixture is stirred for 1 h at −78° C. Then 2-(methylsulfanyl)pyrimidine-4-carbaldehyde (1) (460 mg, 3.0 mmol, 1.0 eq) dissolved in THF was added dropwise to the reaction mixture. After stirring 2 h at −78° C., the solution was poured into aqueous saturated NH₄Cl. The mixture was extracted with ethyl acetate. And the organic layer was washed with brine solution, dried over sodium sulfate and concentrated to provide crude product which was purified by Combiflash Chromatography (4 g column) to afford crude 3-hydroxy-3-(2-methylsulfanylpyrimidin-4-yl)propanoic acid ethyl ester (3) as brown oil (540 mg, Yield: 74%). TLC system: Hexane:EtOAc (1:1), $R_f$ value: ~0.3.

Synthesis of 3-(2-methylsulfanylpyridin-4-yl)-3-oxo-propanoic acid ethyl ester (4)

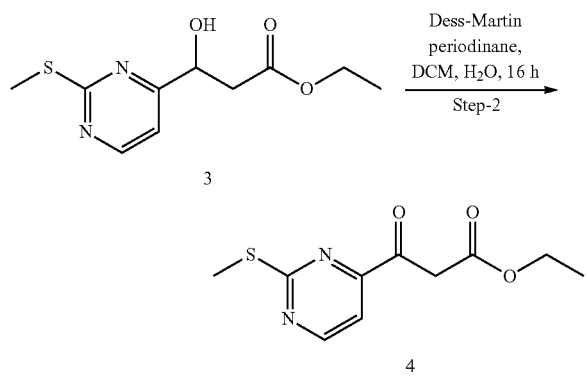

To a stirred solution of 3-hydroxy-3-(2-methylsulfanylpyrimidin-4-yl)propanoic acid ethyl ester (3) (440 mg, 1.82 mmol, 1.0 eq) in DCM (10 mL) at 0° C. was added Dess-Martine periodinane (925 mg, 2.18 mol, 1.2 eq), followed by H₂O (40 mg, 2.18 mol, 1.2 eq). After stirring 16 h at room temperature, aqueous saturated sodium thiosulfate (Na₂S₂O₃) was added to the reaction. The mixture was extracted with ethyl acetate. And the organic layer was washed with brine solution, dried over sodium sulfate and concentrated to provide crude product which was purified by Combiflash Chromatography (4 g column) to afford crude 3-(2-methylsulfanylpyridin-4-yl)-3-oxo-propanoic acid ethyl ester (4) as yellow solid (320 mg, Yield: 73%). TLC system: Hexane:EtOAc (2:1), $R_f$ value: ~0.5.

Synthesis of 3-cyclopropyl-5-(2-methylsulfanylpyrimidin-4-yl)pyrazolo[1,5-a]pyrimidin-7-ol (5a)

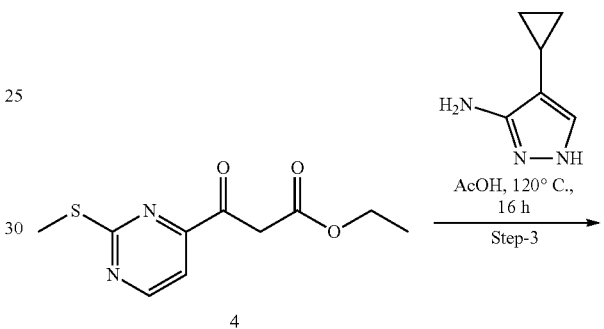

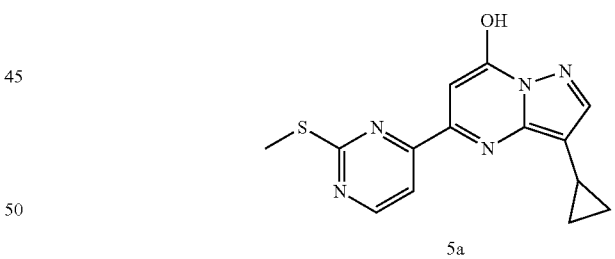

To a stirred solution of 3-(2-methylsulfanylpyridin-4-yl)-3-oxo-propanoic acid ethyl ester (4) (75 mg, 0.31 mmol, 1.0 eq) in acetic acid (AcOH) (5 mL) at room temperature was added 3-amino-4-cyclopropyl-1H-pyrazole (46 mg, 0.37 mmol, 1.2 eq). The reaction mixture was heated to 120° C. for 16 h. After the reaction mixture was then evaporated to remove the acetic acid, water was added. The mixture was extracted with ethyl acetate. And the organic layer was washed with brine solution, dried over sodium sulfate and concentrated to provide crude product 3-cyclopropyl-5-(2-methylsulfanylpyrimidin-4-yl)pyrazolo[1,5-a]pyrimidin-7-ol (5a) as brown solid (93 mg, Yield: 100%). TLC system: DCM:MeOH (10:1), $R_f$ value: ~0.4.

Synthesis of 7-chloro-3-cyclopropyl-5-(2-methylsulfanylpyrimidin-4-yl)pyrazolo[1,5-a]pyrimidine (6a)

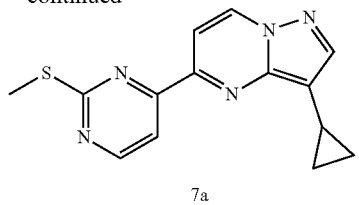

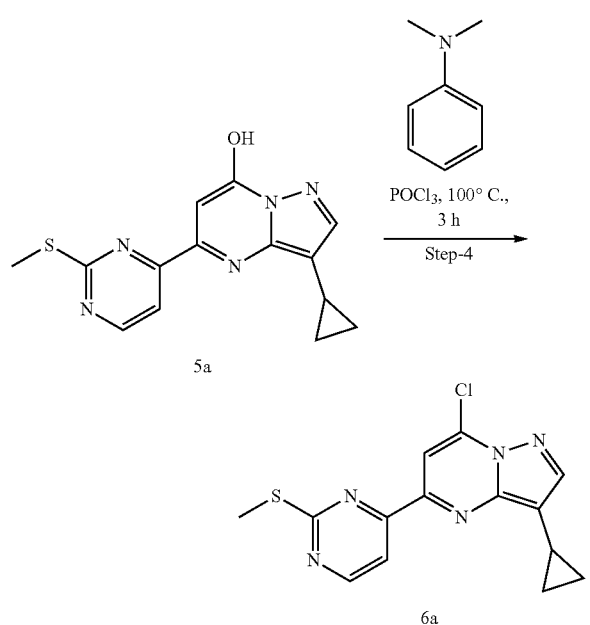

To a stirred solution of 3-cyclopropyl-5-(2-methylsulfanylpyrimidin-4-yl)pyrazolo[1,5-a]pyrimidin-7-ol (5a) (93 mg, 0.31 mmol, 1.0 eq) in Phosphorus (V) oxychloride (POCl₃) (5 mL) at room temperature was added N,N-dimethylaniline (82 mg, 0.68 mmol, 2.2 eq). The reaction mixture was heated to 100° C. for 3 h. After the reaction mixture was added to ice dropwise, aqueous saturated NaHCO₃ was added to adjust pH 7-8. The mixture was extracted with ethyl acetate, and then the organic layer was washed with brine solution, dried over sodium sulfate and concentrated to provide the product which was purified by Combiflash Chromatography (4 g column) to afford 7-chloro-3-cyclopropyl-5-(2-methylsulfanylpyrimidin-4-yl)pyrazolo[1,5-a]pyrimidine (6a) as yellow solid (55 mg, Yield: 56%). TLC system: Hexane:EtOAc (4:1), R_f value: ~0.3.

Synthesis of 3-cyclopropyl-5-(2-methylsulfanylpyrimidin-4-yl)pyrazolo[1,5-a]pyrimidin (7a)

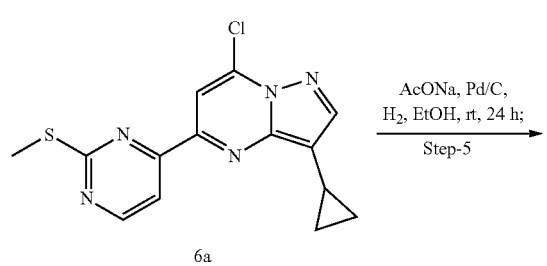

To a stirred solution of 7-chloro-3-cyclopropyl-5-(2-methylsulfanylpyrimidin-4-yl)pyrazolo[1,5-a]pyrimidine (6a) (60 mg, 0.19 mmol, 1.0 eq) in ethanol (10 mL) at room temperature was added sodium acetate (18 mg, 0.21 mmol, 1.1 eq) and 10% Pd/C (6 mg, 10% of 6a). The reaction mixture was stirred under an atmosphere of H₂ for 24 h. The mixture was filtered over Celite® (i.e., diatomaceous earth), washed with ethyl acetate, dried over sodium sulfate and then concentrated to provide the product which was purified by Combiflash Chromatography (4 g column) to afford 3-cyclopropyl-5-(2-methylsulfanylpyrimidin-4-yl)pyrazolo[1,5-a]pyrimidine (7a) as yellow solid (35 mg, Yield: 65%). TLC system: Hexane:EtOAc (2:1), R_f value: ~0.3.

Synthesis of Mixture of 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a)

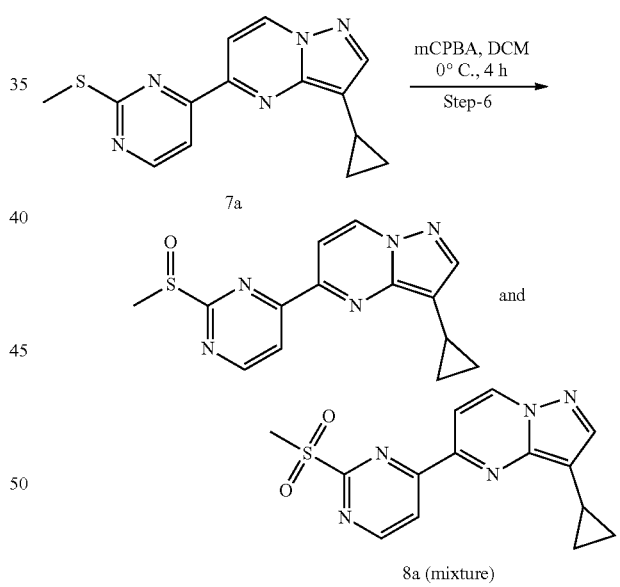

To a stirred solution of 3-cyclopropyl-5-(2-methylsulfanylpyrimidin-4-yl)pyrazolo[1,5-a]pyrimidine (7a) (35 mg, 0.12 mmol, 1.0 eq) in DCM (4 mL) cooled to 0° C. was added 3-chloroperbenzoic acid (mCPBA) (purity, 77%) (36 mg, 0.16 mmol, 1.3 eq). The reaction mixture was stirred at 0° C. for 4 h. After completion of the reaction by TLC, the reaction mixture was quenched with sat aq. NaHCO₃ solution (10 mL) and extracted with ethyl acetate. The combined organic layers were washed with brine solution, dried over sodium sulfate and concentrated to afford crude mixture of 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a) as a yellow solid (36 mg, yield: 89%). TLC system: EtOAc (100%) $R_f$ value: ~0.01 and 0.6.

Synthesis of trans-$N^1$-[4-[(3-cyclopropyl)pyrazolo [1,5-a]pyrimidin-5-yl]pyrimidin-2-yl]-$N^4$-(tetrahydro-2H-pyran-4-yl)cyclohexane-1,4-diamine (Compound I-1)

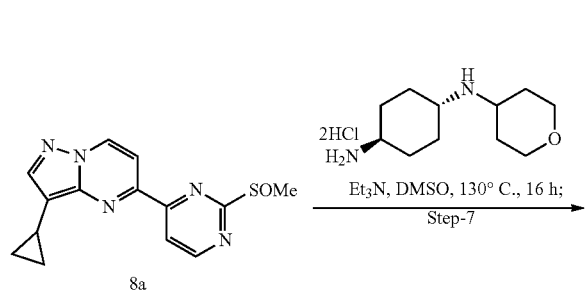

To a stirred solution of mixture of 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a) (25 mg, 0.08 mmol, 1 eq) and (1R*,4R*)—$N^1$-(tetrahydro-2H-pyran-4-yl)cyclohexane-1, 4-diamine dihydrochloride (33 mg, 0.12 mmol, 1.5 eq) in DMSO (5 mL) at room temperature was added trimethylamine (Et$_3$N) (33 mg, 0.32 mmol, 4 eq) and the reaction mixture was stirred at 130° C. for 16 h. After completion of reaction by TLC, reaction mixture was cooled to room temperature, quenched with H$_2$O and extracted with ethyl acetate. The organic layer was washed with brine solution, dried over anhydrous sodium sulfate and then concentrated to provide product which was purified by Combiflash Chromatography (4 g column) to afford trans-$N^1$-[4-[(3-cyclopropyl)pyrazolo[1,5-a]pyrimidin-5-yl]pyrimidin-2-yl]-$N^4$-(tetrahydro-2H-pyran-4-yl)cyclohexane-1,4-diamine (Compound I-1) as yellow solid (15 mg, 43%). TLC system: DCM:MeOH (2:1), $R_f$ value: ~0.3; $^1$HNMR (400 MHz, MeOD-d4) δ 8.82 (d, J=7.3 Hz, 1H), 8.39 (d, J=5.0 Hz, 1H), 7.94 (s, 1H), 7.84 (d, J=7.3 Hz, 1H), 7.57 (d, J=5.0 Hz, 1H), 3.99-3.95 (m, 2H), 3.92-3.82 (m, 1H), 3.47-3.41 (m, 2H), 3.04-2.97 (m, 1H), 2.87-2.81 (m, 1H), 2.21-2.11 (m, 3H), 2.10-2.04 (m, 2H), 1.91-1.87 (m, 2H), 1.50-1.34 (m, 6H), 1.02-0.97 (m, 4H); HRMS (ESI) m/z: [M+H]$^+$ calcd for C$_{24}$H$_{31}$N$_7$O, 434.2663. found 434.2668.

Example 2

Synthesis of Compound 1-2

41
-continued

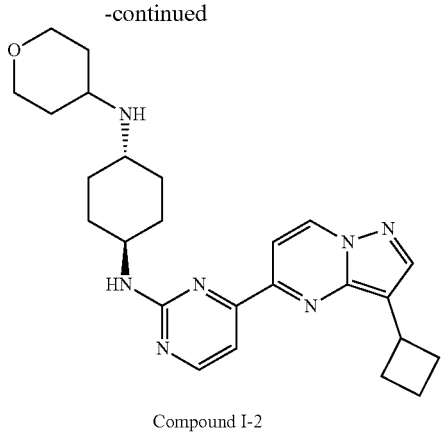

Compound I-2

A precursor 3-(2-methylsulfanylpyridin-4-yl)-3-oxo-propanoic acid ethyl ester (4) was prepared according to the syntheses described in EXAMPLE 1 following the steps 1 and 2.

Synthesis of 3-cyclobutyl-5-(2-methylsulfanylpyrimidin-4-yl)pyrazolo[1,5-a]pyrimidin-7-ol (5b)

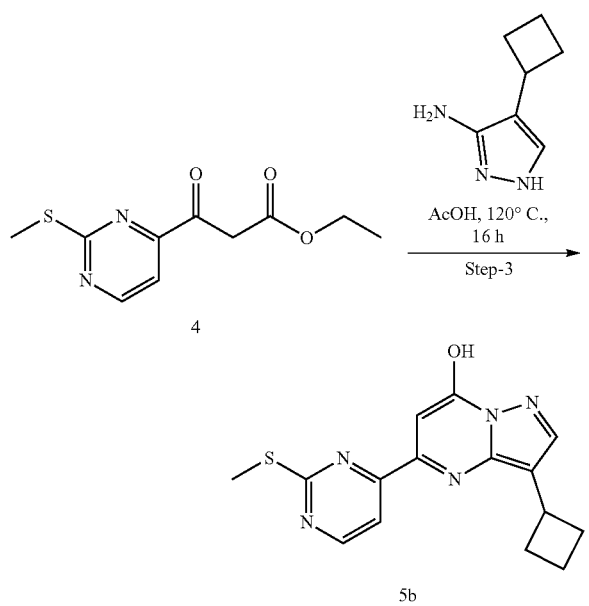

To a stirred solution of 3-(2-methylsulfanylpyridin-4-yl)-3-oxo-propanoic acid ethyl ester (4) (150 mg, 0.65 mmol, 1.0 eq) in acetic acid (AcOH) (5 mL) at room temperature was added 4-cyclobutyl-1H-pyrazol-5-amine (103 mg, 0.75 mmol, 1.2 eq). The reaction mixture was heated to 120° C. for 16 h. After the reaction mixture was evaporated to remove the acetic acid, water was added. The mixture was extracted with ethyl acetate. And the organic layer was washed with brine solution, dried over sodium sulfate and concentrated to provide crude product 3-cyclobutyl-5-(2-methylsulfanylpyrimidin-4-yl)pyrazolo[1,5-a]pyrimidin-7-ol (5b) as brown solid (194 mg, Yield: 100%). TLC system: DCM:MeOH (10:1), $R_f$ value: ~0.3.

42

Synthesis of 7-chloro-3-cyclobutyl-5-(2-methylsulfanylpyrimidin-4-yl)pyrazolo[1,5-a]pyrimidine (6b)

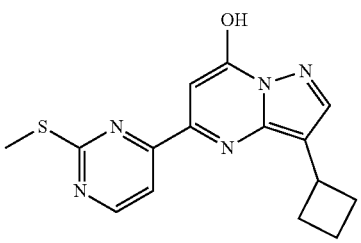 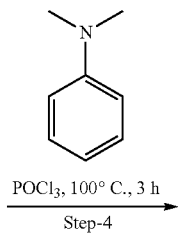

To a stirred solution of 3-cyclobutyl-5-(2-methylsulfanylpyrimidin-4-yl)pyrazolo[1,5-a]pyrimidin-7-ol (5b) (194 mg, 0.62 mmol, 1.0 eq) in Phosphorus (V) oxychloride ($POCl_3$) (5 mL) at room temperature was added N,N-dimethylaniline (165 mg, 1.36 mmol, 2.2 eq). The reaction mixture was heated to 100° C. for 3 h. After the reaction mixture was added to ice dropwise, aqueous saturated $NaHCO_3$ was added to adjust pH 7-8. The mixture was extracted with ethyl acetate, and then the organic layer was washed with brine solution, dried over sodium sulfate and concentrated to provide the product which was purified by Combiflash Chromatography (4 g column) to afford 7-chloro-3-cyclobutyl-5-(2-methylsulfanylpyrimidin-4-yl)pyrazolo[1,5-a]pyrimidine (6b) as yellow solid (150 mg, Yield: 73%). TLC system: Hexane:EtOAc (4:1), $R_f$ value: ~0.3.

Synthesis of 3-cyclobutyl-5-(2-methylsulfanyl-pyrimidin-4-yl)pyrazolo[1,5-a]pyrimidine (7b)

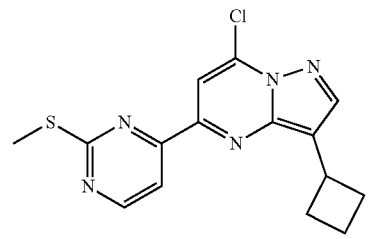

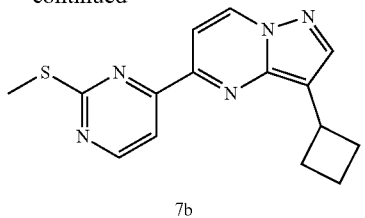

7b

To a stirred solution of 7-chloro-3-cyclobutyl-5-(2-methylsulfanylpyrimidin-4-yl)pyrazolo[1,5-a]pyrimidine (6b) (150 mg, 0.45 mmol, 1.0 eq) in ethanol (10 mL) at room temperature was added sodium acetate (41 mg, 0.50 mmol, 1.1 eq) and 10% Pd/C (15 mg, 10% of 6b). The reaction mixture was stirred under an atmosphere of H₂ for 24 h. Then the mixture was filtered over Celite® (i.e., diatomaceous earth), washed with ethyl acetate, dried over sodium sulfate and then concentrated to provide the product which was purified by Combiflash Chromatography (4 g column) to afford 3-cyclobutyl-5-(2-methylsulfanylpyrimidin-4-yl) pyrazolo[1,5-a]pyrimidine (7b) as yellow solid (95 mg, Yield: 71%). TLC system: Hexane:EtOAc (4:1), $R_f$ value: ~0.2.

Synthesis of Mixture of 3-cyclobutyl-5-(2-methylsulfinylpyrimidin-4-yl)pyrazolo[1,5-a]pyrimidine and 3-cyclobutyl-5-(2-methylsulfonylpyrimidin-4-yl)pyrazolo[1,5-a]pyrimidine(8b)

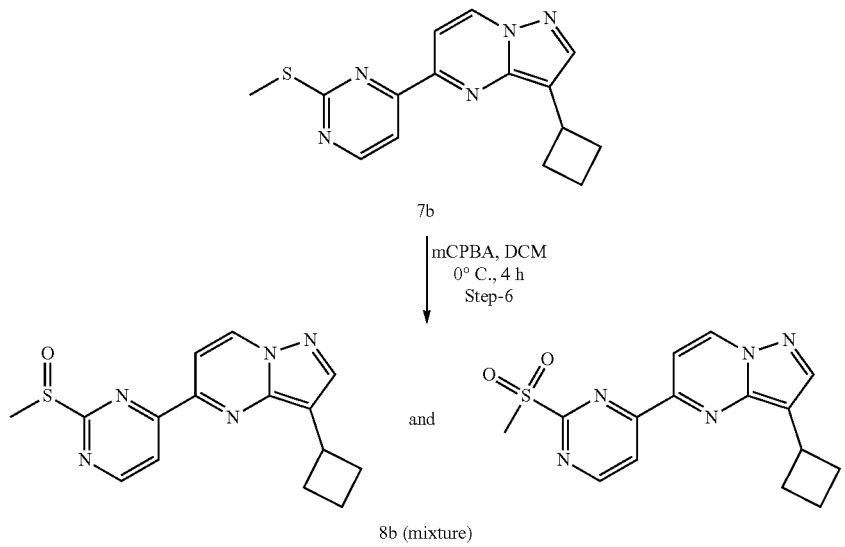

8b (mixture)

To a stirred solution of 3-cyclobutyl-5-(2-methylsulfanylpyrimidin-4-yl)pyrazolo[1,5-a]pyrimidine (7b) (95 mg, 0.32 mmol, 1.0 eq) in DCM (4 mL) cooled to 0° C. and added mCPBA (purity, 77%) (94 mg, 0.42 mmol, 1.3 eq). The reaction mixture was stirred at 0° C. for 4 h. After completion of reaction by TLC, the reaction mixture was quenched with sat aq. NaHCO₃ solution (10 mL) and extracted with ethyl acetate. The combined organic layers were washed with brine solution, dried over sodium sulfate and concentrated to afford crude mixture of 3-cyclobutyl-5-(2-methylsulfinylpyrimidin-4-yl)pyrazolo[1,5-a]pyrimidine and 3-cyclobutyl-5-(2-methylsulfonylpyrimidin-4-yl) pyrazolo[1,5-a]pyrimidine(8b) as a yellow solid (100 mg, yield: 100%). TLC system: EtOAc (100%) $R_f$ value: ~0.05.

Synthesis of trans-N¹-[4-[(3-cyclobutyl)pyrazolo[1,5-a]pyrimidin-5-yl]pyrimidin-2-yl]-N⁴-(tetrahydro-2H-pyran-4-yl)cyclohexane-1,4-diamine (Compound I-2)

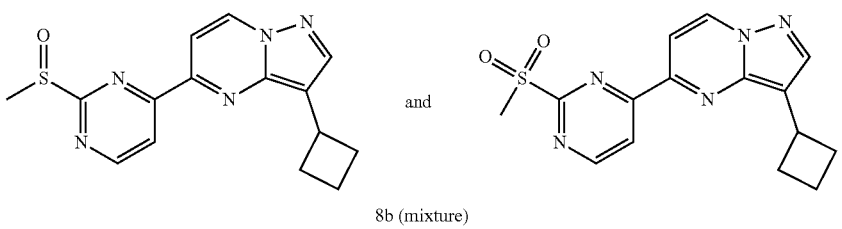

8b (mixture)

-continued

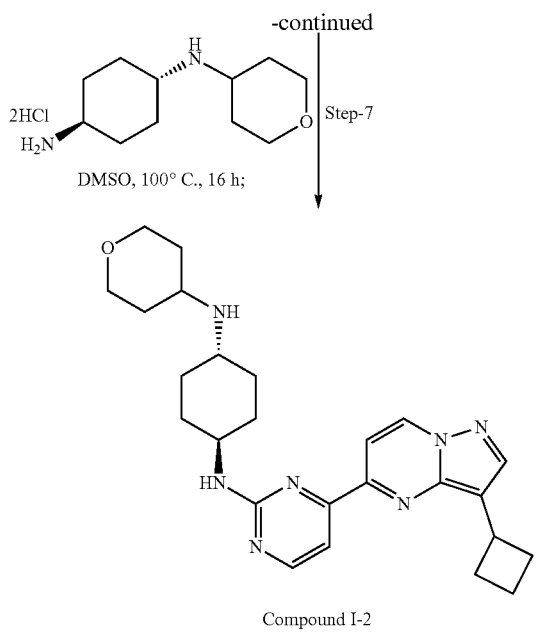

Compound I-2

To a stirred solution of mixture of 3-cyclobutyl-5-(2-methylsulfinylpyrimidin-4-yl)pyrazolo[1,5-a]pyrimidine and 3-cyclobutyl-5-(2-methylsulfonylpyrimidin-4-yl)pyrazolo[1,5-a]pyrimidine(8b) (25 mg, 0.08 mmol, 1 eq) and (1R*,4R*)—N$^1$-(tetrahydro-2H-pyran-4-yl)cyclohexane-1,4-diamine dihydrochloride (33 mg, 0.12 mmol, 1.5 eq) in DMSO (5 mL) at room temperature was added trimethylamine (Et$_3$N) (33 mg, 0.32 mmol, 4 eq) and the reaction mixture was stirred at 100° C. for 16 h. After completion of reaction by TLC, the reaction mixture was cooled to room temperature, quenched with H$_2$O and extracted with ethyl acetate. The organic layer was washed with brine solution, dried over anhydrous sodium sulfate and then concentrated to provide product which was purified by Combiflash Chromatography (4 g column) to afford trans-N$^1$-[4-[(3-cyclobutyl)pyrazolo[1,5-a]pyrimidin-5-yl]pyrimidin-2-yl]-N$^4$-(tetrahydro-2H-pyran-4-yl)cyclohexane-1,4-diamine (Compound I-2) as yellow solid (15 mg, 42%). TLC system: DCM:MeOH (5:1), R$_f$ value: ~0.3; $^1$HNMR (400 MHz, MeOD-d4) δ 8.83 (d, J=7.3 Hz, 1H), 8.38 (d, J=5.0 Hz, 1H), 8.10 (s, 1H), 7.85 (d, J=7.3 Hz, 1H), 7.57 (d, J=5.0 Hz, 1H), 3.99-3.95 (m, 2H), 3.90-3.84 (m, 2H), 3.46-3.40 (m, 2H), 3.06-3.00 (m, 1H), 2.90-2.82 (m, 1H), 2.46-2.40 (m, 4H), 2.16-2.00 (m, 6H), 1.91-1.87 (m, 2H), 1.51-1.35 (m, 6H); HRMS (ESI) m/z: [M+H]$^+$ calcd for C$_{25}$H$_{33}$N$_7$O, 448.2819. found 448.2852.

Example 3

Synthesis of Compound I-3

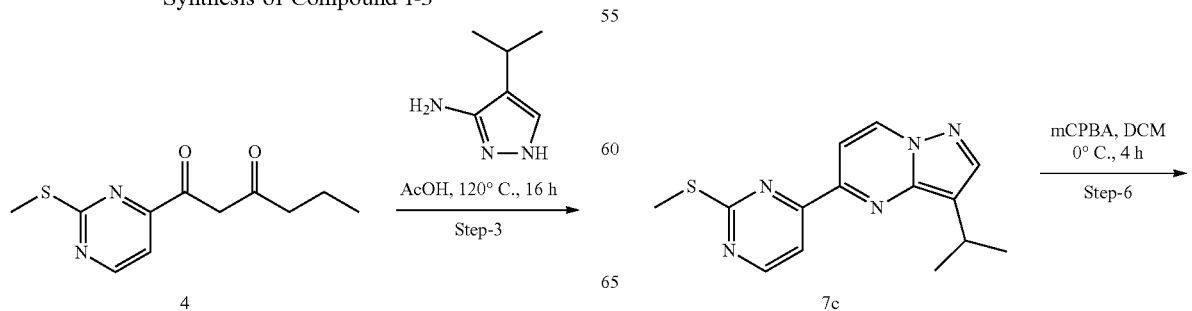

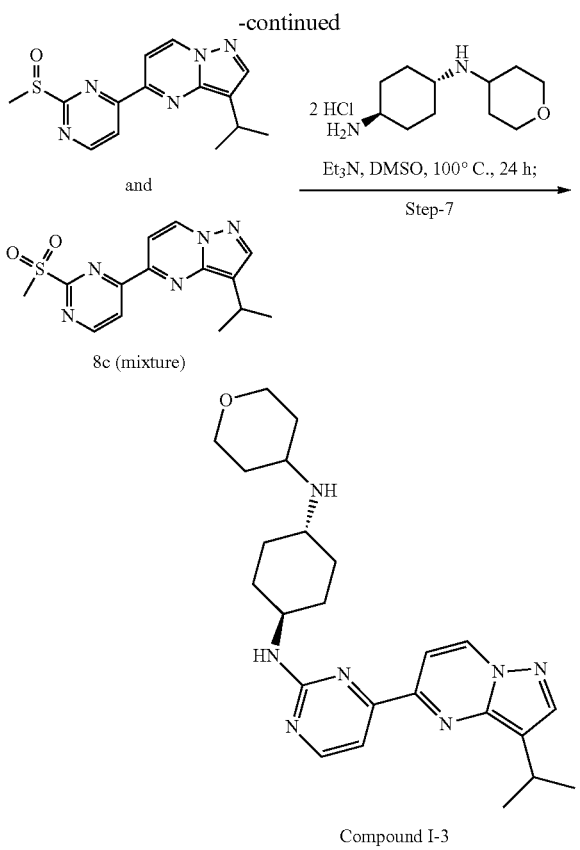

8c (mixture)

Compound I-3

A precursor 3-(2-methylsulfanylpyridin-4-yl)-3-oxo-propanoic acid ethyl ester (4) was prepared according to the syntheses described in EXAMPLE 1 following the steps 1 and 2.

Synthesis of 3-isopropyl-5-(2-methylsulfanylpyrimidin-4-yl)pyrazolo[1,5-a]pyrimidin-7-ol (5c)

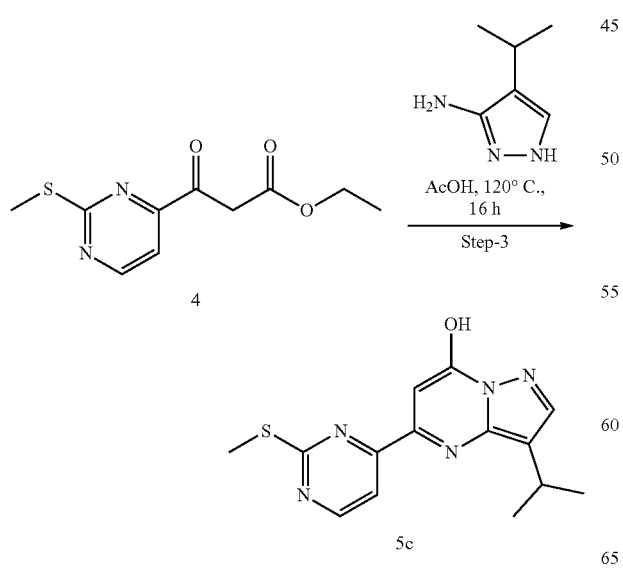

To a stirred solution of 3-(2-methylsulfanylpyrimidin-4-yl)-3-oxo-propanoic acid ethyl ester (4) (150 mg, 0.62 mmol, 1.0 eq) in acetic acid (AcOH) (5 mL) at room temperature was added 4-isopropyl-1H-pyrazol-5-amine (94 mg, 0.75 mol, 1.2 eq). The reaction mixture was heated to 120° C. for 16 h. After the reaction mixture was then evaporated to remove the AcOH, water was added. The mixture was extracted with ethyl acetate. And the organic layer was washed with brine solution, dried over sodium sulfate and concentrated to provide crude product 3-isopropyl-5-(2-methylsulfanylpyrimidin-4-yl)pyrazolo[1,5-a]pyrimidin-7-ol (5c) as brown solid (187 mg, Yield: 100%). TLC system: DCM:MeOH (10:1), $R_f$ value: ~0.3.

Synthesis of 7-chloro-3-isopropyl-5-(2-methylsulfanylpyrimidin-4-yl)pyrazolo[1,5-a]pyrimidine (6c)

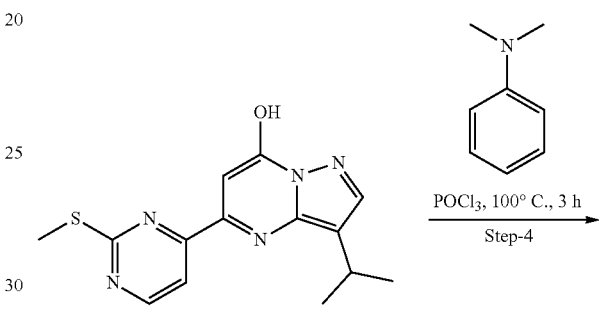

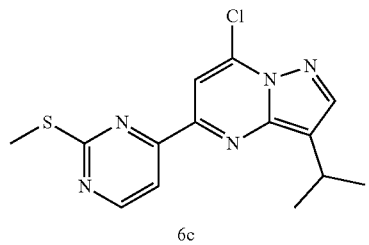

To a stirred solution of 3-isopropyl-5-(2-methylsulfanylpyrimidin-4-yl)pyrazolo[1,5-a]pyrimidin-7-ol (5c) (187 mg, 0.62 mmol, 1.0 eq) in Phosphorus (V) oxychloride (POCl$_3$) (5 mL) at room temperature was added N,N-dimethylaniline (165 mg, 1.36 mmol, 2.2 eq). The reaction mixture was heated to 100° C. for 3 h. After the reaction mixture was added to ice dropwise, aqueous saturated NaHCO$_3$ was added to adjust pH 7-8. The mixture was extracted with ethyl acetate, and then the organic layer was washed with brine solution, dried over sodium sulfate and concentrated to provide the product which was purified by Combiflash Chromatography (4 g column) to afford 7-chloro-3-isopropyl-5-(2-methylsulfanylpyrimidin-4-yl) pyrazolo[1,5-a]pyrimidine (6c) as yellow solid (130 mg, Yield: 66%). TLC system: Hexane:EtOAc (4:1), $R_f$ value: ~0.3.

Synthesis of 3-isopropyl-5-(2-methylsulfanylpyrimidin-4-yl)pyrazolo[1,5-a]pyrimidine (7c)

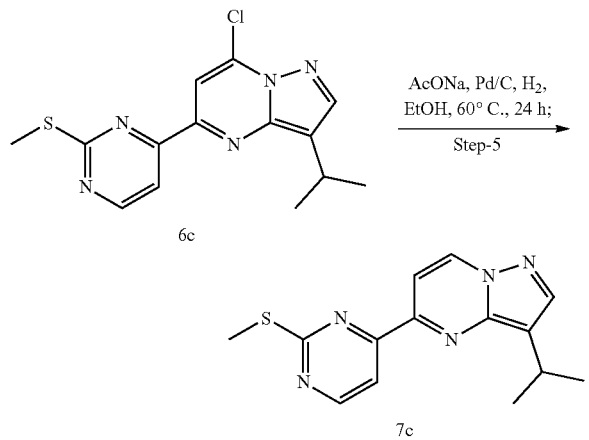

To a stirred solution of 7-chloro-3-isopropyl-5-(2-methylsulfanylpyrimidin-4-yl)pyrazolo[1,5-a]pyrimidine (6c, 3020-03_CDK9-P5-A) (130 mg, 0.41 mmol, 1.0 eq) in ethanol (10 mL) at room temperature was added sodium acetate (67 mg, 0.82 mmol, 1.1 eq) and 10% Pd/C (13 mg, 10% of 6c). The reaction mixture was stirred under an atmosphere of H₂ at 60° C. for 24 h. The mixture was filtered over Celite® (i.e., diatomaceous earth), washed with ethyl acetate, dried over sodium sulfate and then concentrated to provide the product which was purified by Combiflash Chromatography (4 g column) to afford 3-isopropyl-5-(2-methylsulfanylpyrimidin-4-yl)pyrazolo[1,5-a]pyrimidine (7c, 3020-04_CDK9-P7-A) as yellow solid (90 mg, Yield: 77%). TLC system: Hexane:EtOAc (2:1), $R_f$ value: ~0.3.

Synthesis of Mixture of 3-isopropyl-5-(2-methylsulfinylpyrimidin-4-yl)pyrazolo[1,5-a]pyrimidine and 3-isopropyl-5-(2-methylsulfonylpyrimidin-4-yl)pyrazolo[1,5-a]pyrimidine(8c)

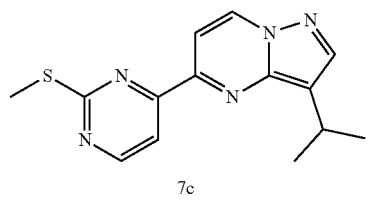

mCPBA, DCM
0° C., 4 h
Step-6

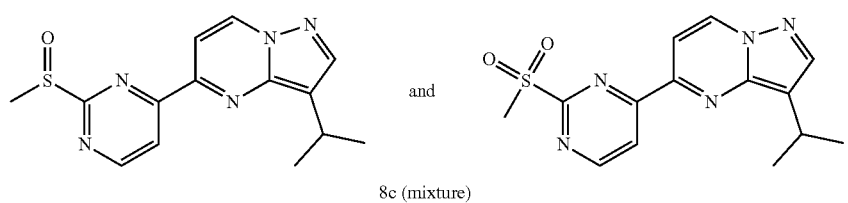

8c (mixture)

To a stirred solution of 3-isopropyl-5-(2-methylsulfanylpyrimidin-4-yl)pyrazolo[1,5-a]pyrimidine (7c) (95 mg, 0.33 mmol, 1.0 eq) in DCM (4 mL) cooled to 0° C. and added 3-chloroperbenzoic acid (mCPBA) (purity, 77%) (96 mg, 0.43 mmol, 1.3 eq). The reaction mixture was stirred at 0° C. for 4 h. After completion of reaction by TLC, the reaction mixture was quenched with sat aq. NaHCO₃ solution (10 mL) and extracted with ethyl acetate. The combined organic layers were washed with brine solution, dried over sodium sulfate and concentrated to afford crude mixture of 3-isopropyl-5-(2-methylsulfinylpyrimidin-4-yl)pyrazolo[1,5-a]pyrimidine and 3-isopropyl-5-(2-methylsulfonylpyrimidin-4-yl)pyrazolo[1,5-a]pyrimidine (8c) as a yellow solid (80 mg, yield: 81%). TLC system: DCM:MeOH (10:1) $R_f$ value: ~0.3 and 0.7.

Synthesis of trans-$N^1$-[4-[(3-isopropyl)pyrazolo[1,5-a]pyrimidin-5-yl]pyrimidin-2-yl]-$N^4$-(tetrahydro-2H-pyran-4-yl)cyclohexane-1,4-diamine (Compound I-3)

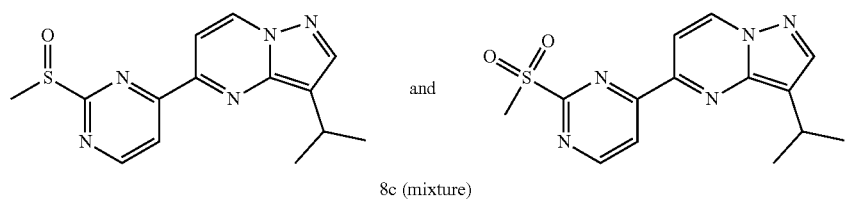

8c (mixture)

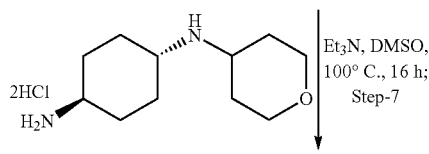

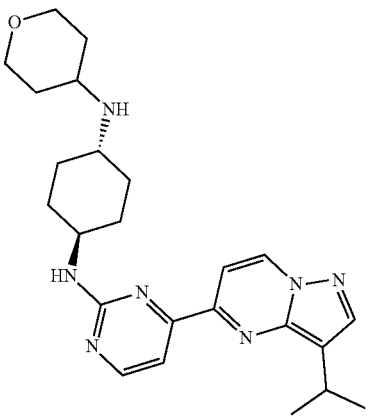

Compound I-3

To a stirred solution of mixture of 3-isopropyl-5-(2-methylsulfinyl-pyrimidin-4-yl)pyrazolo[1,5-a]pyrimidine and 3-isopropyl-5-(2-methylsulfonylpyrimidin-4-yl)pyrazolo[1,5-a]pyrimidine (8c) (25 mg, 0.08 mmol, 1 eq) and (1R*, 4R*)—N$^1$-(tetrahydro-2H-pyran-4-yl)cyclohexane-1,4-diamine dihydrochloride (33 mg, 0.12 mmol, 1.5 eq) in DMSO (5 mL) at room temperature was added sodium bicarbonate (NaHCO$_3$) (32 mg, 0.32 mmol, 4 eq) and the reaction mixture was stirred at 100° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford trans-N-[4-[(3-isopropyl)pyrazolo[1,5-a]pyrimidin-5-yl]pyrimidin-2-yl]-N$^4$-(tetrahydro-2H-pyran-4-yl)cyclohexane-1,4-diamine (Compound I-3) as yellow solid (14 mg, 40%). TLC system: DCM:MeOH (5:1), R$_f$ value: ~0.3; $^1$HNMR (400 MHz, MeOD-d4) δ 8.86 (d, J=7.3 Hz, 1H), 8.39 (d, J=5.0 Hz, 1H), 8.08 (s, 1H), 7.88 (d, J=7.3 Hz, 1H), 7.60 (d, J=5.0 Hz, 1H), 3.98-3.95 (m, 2H), 3.90-3.83 (m, 1H), 3.47-3.41 (m, 2H), 3.39-3.34 (m, 1H), 3.08-3.00 (m, 1H), 2.89-2.80 (m, 1H), 2.24-2.15 (m, 2H), 2.11-2.05 (m, 2H), 1.90-1.87 (m, 2H), 1.49-1.36 (m, 12H); HRMS (ESI) m/z: [M+H]$^+$ calcd for C$_{24}$H$_{33}$N$_7$O, 436.2819. found 436.2853.

Example 4

Synthesis of Compound I-4

A precursor 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a) was prepared according to the syntheses described in EXAMPLE 1 following the steps 1-6.

Synthesis of tert-butyl trans-4-[4-[(3-cyclopropyl)pyrazolo[1,5-a]pyrimidin-5-yl]pyrimidin-2-yl]aminomethyl-3-hydroxylpiperidine-1-carboxylate (9a)

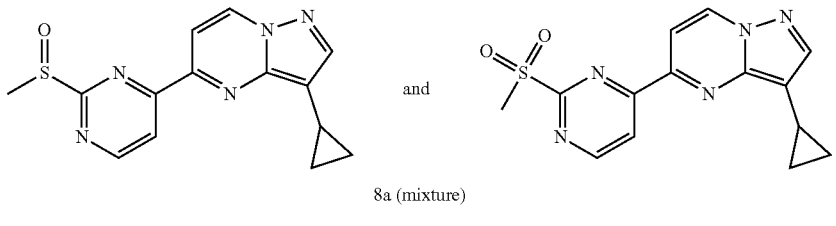

8a (mixture)

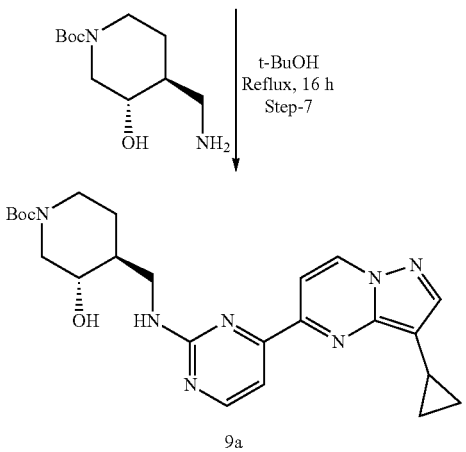

9a

To a stirred solution of mixture of 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a) (18 mg, 0.06 mmol, 1 eq) in tert-butanol (5 mL) at room temperature was added trans-1-Boc-4-aminomethyl-3-hydroxypiperidine (20 mg, 0.09 mmol, 1.5 eq) and the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl trans-4-[4-[(3-cyclopropyl)pyrazolo[1,5-a]pyrimidin-5-yl]pyrimidin-2-yl]aminomethyl-3-hydroxylpiperidine-1-carboxylate (9a) as yellow solid (20 mg, 71%). TLC system: EtOAc (100%), $R_f$ value: ~0.2.

Synthesis of trans-5-[2-(3-hydroxypiperidin-4-yl)methylaminopyrimidin-4-yl]-3-cyclopropylpyrazolo[1,5-a]pyrimidine (Compound I-4)

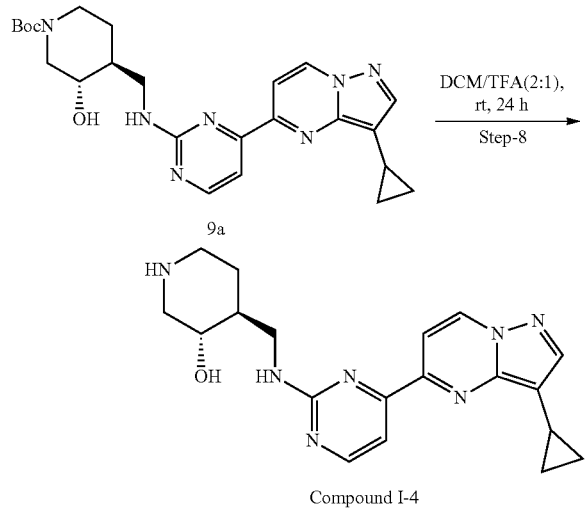

To a stirred solution of tert-butyl trans-4-[4-[(3-cyclopropyl)pyrazolo[1,5-a]pyrimidin-5-yl]pyrimidin-2-yl]aminomethyl-3-hydroxylpiperidine-1-carboxylate (9a) (20 mg, 0.04 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. The mixture was quenched with sat aq. $NaHCO_3$ solution (10 mL) and extracted with ethyl acetate. The combined organic layers were washed with brine solution, dried over sodium sulfate and then concentrated to provide product which was purified by Combiflash Chromatography (4 g column) to afford trans-5-[2-(3-hydroxypiperidin-4-yl)methylaminopyrimidin-4-yl]-3-cyclopropylpyrazolo[1, 5-a]pyrimidine (Compound I-4) as yellow solid (15 mg, 93%). TLC system: MeOH (100% with 1% Et3N), $R_f$ value: ~0.2; $^1$HNMR (400 MHz, MeOD-d4) δ 8.81 (d, J=7.3 Hz, 1H), 8.39 (d, J=5.1 Hz, 1H), 7.93 (s, 1H), 7.88 (d, J=7.3 Hz, 1H), 7.58 (d, J=5.1 Hz, 1H), 3.75-3.67 (m, 1H), 3.62-3.57 (m, 1H), 3.49-3.45 (m, 1H), 3.21-3.17 (m, 1H), 3.09-3.05 (m, 1H), 2.67-2.61 (m, 1H), 2.54-2.49 (m, 1H), 2.17-2.08 (m, 1H), 1.95-1.89 (m, 1H), 1.78-1.72 (m, 1H), 1.49-1.37 (m, 1H), 1.02-0.95 (m, 4H); HRMS (ESI) m/z: [M+H]$^+$ calcd for $C_{19}H_{23}N_7O$, 366.2037. found 366.2044.

Example 5

Synthesis of Compound I-5

A precursor 3-cyclobutyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8b) was prepared according to the syntheses described in EXAMPLE 1 following the steps 1-4 and EXAMPLE 2 following the steps 5-6. Synthesis of tert-butyl trans-4-[4-[(3-cyclobutyl)pyrazolo[1,5-a]pyrimidin-5-yl]pyrimidin-2-yl]aminomethyl-3-hydroxylpiperidine-1-carboxylate (9b)

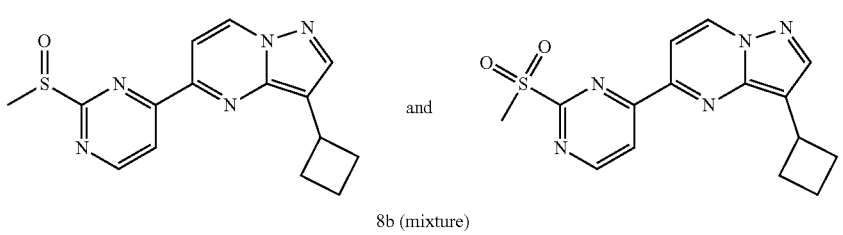

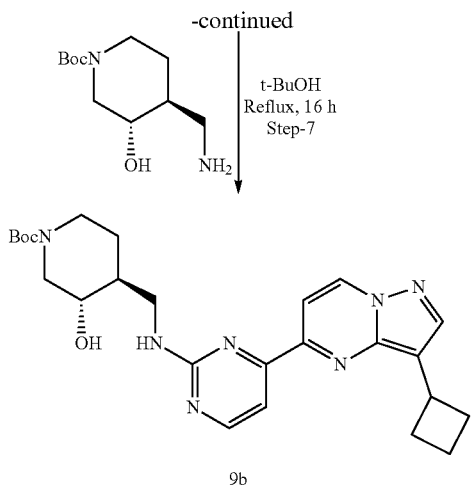

To a stirred solution of mixture of 3-cyclobutyl-5-(2-methylsulfinylpyrimidin-4-yl)pyrazolo[1,5-a]pyrimidine and 3-cyclobutyl-5-(2-methylsulfonylpyrimidin-4-yl)pyrazolo[1,5-a]pyrimidine (8b) (25 mg, 0.08 mmol, 1 eq) in tert-butanol (5 mL) at room temperature was added trans-1-Boc-4-aminomethyl-3-hydroxypiperidine (28 mg, 0.12 mmol, 1.5 eq) and the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl trans-4-[4-[(3-cyclobutyl)pyrazolo[1,5-a]pyrimidin-5-yl]pyrimidin-2-yl]aminomethyl-3-hydroxylpiperidine-1-carboxylate (9b) as yellow solid (35 mg, 92%). TLC system: EtOAc (100%), $R_f$ value: ~0.3.

Synthesis of trans-5-[2-(3-hydroxypiperidin-4-yl) methylaminopyrimidin-4-yl]-3-cyclobutylpyrazolo [1,5-a]pyrimidine (Compound I-5)

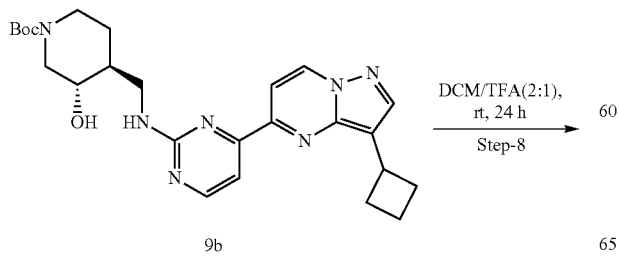

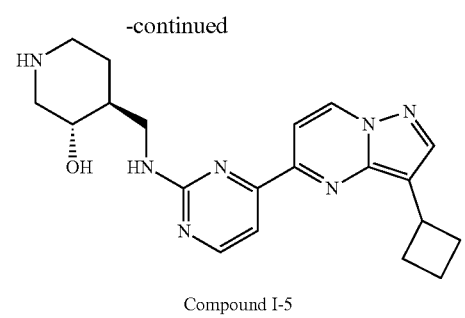

Compound I-5

To a stirred solution of tert-butyl trans-4-[4-[(3-cyclobutyl)pyrazolo[1,5-a]pyrimidin-5-yl]pyrimidin-2-yl] aminomethyl-3-hydroxylpiperidine-1-carboxylate (9b) (25 mg, 0.05 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid appeared in the reaction. The mixture was centrifuged, washed over diethyl ether and dried at room temperature to provide the product trans-5-[2-(3-hydroxypiperidin-4-yl)methylaminopyrimidin-4-yl]-3-cyclobutylpyrazolo[1, 5-a]pyrimidine Trifluoroacetate (Compound I-5) as yellow solid (30 mg, 100%); $^1$HNMR (400 MHz, MeOD-d4) δ 8.92 (d, J=7.3 Hz, 1H), 8.46 (d, J=5.6 Hz, 1H), 8.18 (s, 1H), 7.97 (broad peak, 1H), 7.79 (broad peak, 1H), 4.07-3.80 (m, 2H), 3.79-3.60 (m, 2H), 3.45-3.35 (m, 2H), 3.03-2.96 (m, 1H), 2.87-2.81 (m, 1H), 2.54-2.38 (m, 4H), 2.25-2.10 (m, 2H), 2.07-1.92 (m, 2H), 1.68-1.59 (m, 1H); HRMS (ESI) m/z: [M+H]$^+$ calcd for $C_{20}H_{25}N_7O$, 380.2193. found 380.2222.

Example 6

Synthesis of Compound I-6

A precursor 3-isopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8c) was prepared according to the syntheses described in EXAMPLE 1 following the steps 1-4 and EXAMPLE 3 following the steps 5-6.

Synthesis of tert-butyl trans-4-[4-[(3-isopropyl)pyrazolo[1,5-a]pyrimidin-5-yl]pyrimidin-2-yl]aminomethyl-3-hydroxylpiperidine-1-carboxylate (9c)

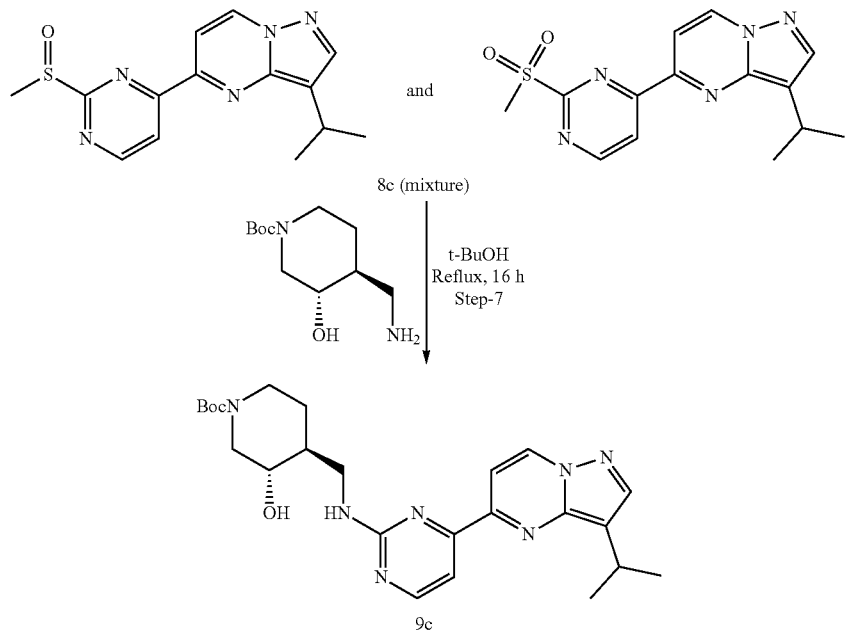

To a stirred solution of mixture of 3-isopropyl-5-(2-methylsulfinylpyrimidin-4-yl)pyrazolo[1,5-a]pyrimidine and 3-isopropyl-5-(2-methylsulfonylpyrimidin-4-yl)pyrazolo[1,5-a]pyrimidine (8c) (25 mg, 0.08 mmol, 1 eq) in tert-butanol (5 mL) at room temperature was added trans-1-Boc-4-aminomethyl-3-hydroxypiperidine (20 mg, 0.09 mmol, 1.5 eq) and the reaction mixture was stirred at 95° C. for 16 h. After completion of reaction by TLC, reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl trans-4-[4-[(3-isopropyl)pyrazolo[1,5-a]pyrimidin-5-yl]pyrimidin-2-yl]aminomethyl-3-hydroxylpiperidine-1-carboxylate (9c) as yellow solid (30 mg, 81%). TLC system: EtOAc (100%), $R_f$ value: ~0.2.

Synthesis of trans-5-[2-(3-hydroxypiperidin-4-yl)methylaminopyrimidin-4-yl]-3-isopropylpyrazolo[1,5-a]pyrimidine Trifluoroacetate (Compound I-6)

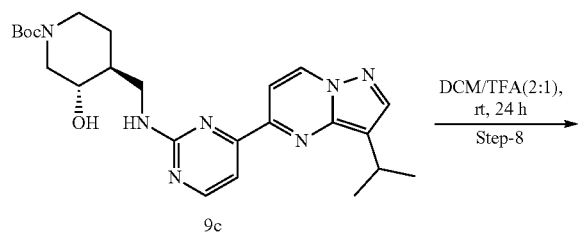

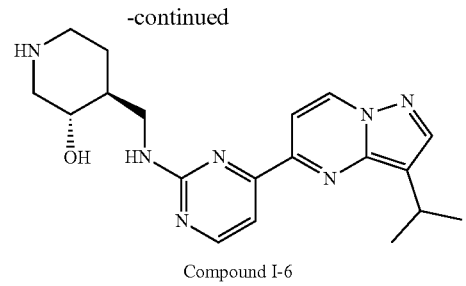

Compound I-6

To a stirred solution of tert-butyl trans-4-[4-[(3-isopropyl)pyrazolo[1,5-a]pyrimidin-5-yl]pyrimidin-2-yl]aminomethyl-3-hydroxylpiperidine-1-carboxylate (9c) (25 mg, 0.05 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, trans-5-[2-(3-hydroxypiperidin-4-yl)methylaminopyrimidin-4-yl]-3-isopropylpyrazolo[1,5-a]pyrimidine Trifluoroacetate (Compound I-6) as yellow solid (30 mg, 100%). $^1$HNMR (400 MHz, MeOD-d4) δ 8.93 (d, J=7.3 Hz, 1H), 8.46 (d, J=5.6 Hz, 1H), 8.13 (s, 1H), 7.99 (broad peak, 1H), 7.80 (broad peak, 1H), 3.97 (broad peak, 1H), 3.79-3.59 (m, 2H), 3.45-3.35 (m, 2H), 3.03-2.96 (m, 1H), 2.87-2.81 (m, 1H), 1.69-1.59 (m, 1H), 1.46 (d, J=6.9 Hz, 1H); HRMS (ESI) m/z: [M+H]$^+$ calcd for $C_{19}H_{25}N_7O$, 368.2193. found 368.2225.

Example 7

Synthesis of Compound I-7

A precursor 3-(2-methylsulfanylpyrimidin-4-yl)-3-oxo-propanoic acid ethyl ester (4) was prepared according to the syntheses described in EXAMPLE 1 following the steps 1-2.

Synthesis of 5-(2-methylsulfanylpyrimidin-4-yl)pyrazolo[1,5-a]pyrimidin-7-ol (5d)

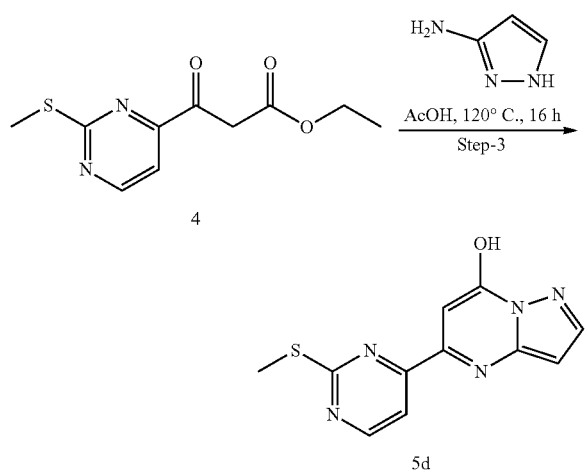

To a stirred solution of 3-(2-methylsulfanylpyrimidin-4-yl)-3-oxo-propanoic acid ethyl ester (4) (680 mg, 2.83 mmol, 1.0 eq) in acetic acid (AcOH) (10 mL) at room temperature was added 1H-pyrazol-5-amine (282 mg, 3.4 mmol, 1.2 eq). The reaction mixture was heated to 120° C. for 16 h. After the reaction mixture was then evaporated to remove the AcOH, water was added. The mixture was extracted with ethyl acetate. And the organic layer was washed with brine solution, dried over sodium sulfate and concentrated to provide crude 5-(2-methylsulfanylpyrimidin-4-yl)pyrazolo[1,5-a]pyrimidin-7-ol (5d) (734 mg, Yield: 100%). TLC system: DCM:MeOH (10:1), $R_f$ value: ~0.3.

Synthesis of 7-chloro-5-(2-methylsulfanylpyrimidin-4-yl)pyrazolo[1,5-a]pyrimidine (6d)

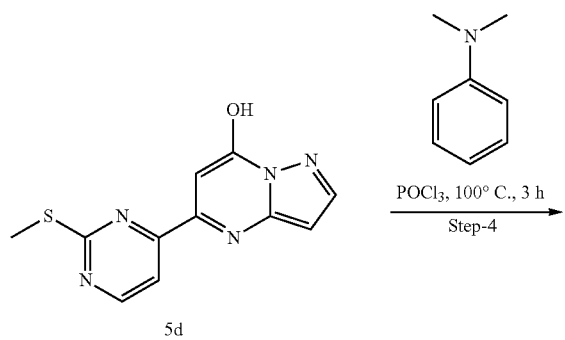

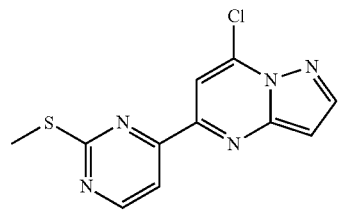

To a stirred solution of 5-(2-methylsulfanylpyrimidin-4-yl)pyrazolo[1,5-a]pyrimidin-7-ol (5d) (734 mg, 2.83 mmol, 1.0 eq) in Phosphorus (V) oxychloride (POCl₃) (5 mL) at room temperature was added N,N-dimethylaniline (755 mg, 6.23 mmol, 2.2 eq). The reaction mixture was heated to 100° C. for 3 h. After the reaction mixture was added to ice dropwise, aqueous saturated NaHCO₃ was added to adjust pH 7-8. The mixture was extracted with ethyl acetate, and then the organic layer was washed with brine solution, dried over sodium sulfate and concentrated to provide the product which was purified by Combiflash Chromatography (4 g column) to afford 7-chloro-5-(2-methylsulfanylpyrimidin-4-yl)pyrazolo[1,5-a]pyrimidine (6d) as yellow solid (420 mg, Yield: 53%). TLC system: Hexane:EtOAc (4:1), $R_f$ value: ~0.3.

Synthesis of 5-(2-methylsulfanylpyrimidin-4-yl)pyrazolo[1,5-a]pyrimidine (7d)

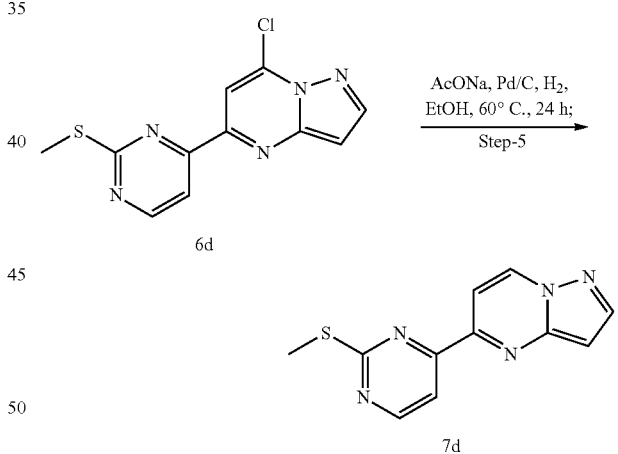

To a stirred solution of 7-chloro-5-(2-methylsulfanylpyrimidin-4-yl)pyrazolo[1,5-a]pyrimidine (6d) (400 mg, 1.44 mmol, 1.0 eq) in ethanol (10 mL) at room temperature was added sodium acetate (236 mg, 2.88 mmol, 2.0 eq) and 10% Pd/C (40 mg, 10% of 6). The reaction mixture was stirred under an atmosphere of H₂ at 60° C. for 24 h. The mixture was filtered over Celite® (i.e., diatomaceous earth), washed with ethyl acetate, dried over sodium sulfate and then concentrated to provide the product which was purified by combiflash chromatography (4 g column) to afford 5-(2-methylsulfanylpyrimidin-4-yl)pyrazolo[1,5-a]pyrimidine (7d) as yellow solid (210 mg, Yield: 60%). TLC system: Hexane:EtOAc (4:1), $R_f$ value: ~0.2.

Synthesis of Mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d)

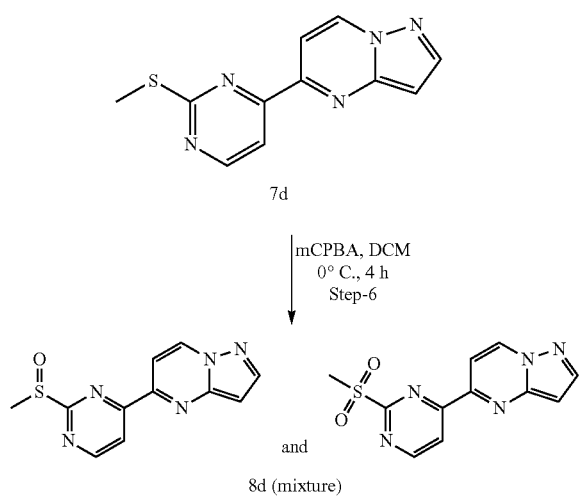

To a stirred solution of 5-(2-methylsulfanylpyrimidin-4-yl)pyrazolo[1,5-a]pyrimidine (7d) (60 mg, 0.25 mmol, 1.0 eq) in DCM (4 mL) cooled to 0° C. and added 3-chloroperbenzoic acid (mCPBA) (purity, 77%) (74 mg, 0.33 mmol, 1.3 eq). The reaction mixture was stirred at 0° C. for 4 h. After completion of reaction by TLC, reaction mixture was quenched with sat aq. NaHCO₃ solution (10 mL) and extracted with ethyl acetate. The combined organic layers were washed with brine solution, dried over sodium sulfate and concentrated to afford crude mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) as a yellow solid (65 mg, yield: 100%). TLC system: EtOAc (100%) R$_f$ value: ~0.01 and 0.4.

Synthesis of tert-butyl trans-3-hydroxyl-4-[4-[pyrazolo[1,5-a]pyrimidin-5-yl]pyrimidin-2-yl]aminomethylpiperidine-1-carboxylate (9d)

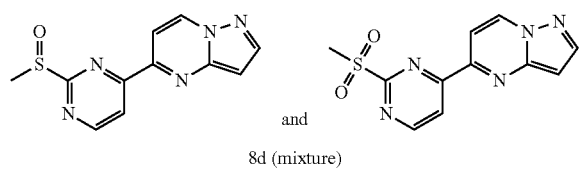

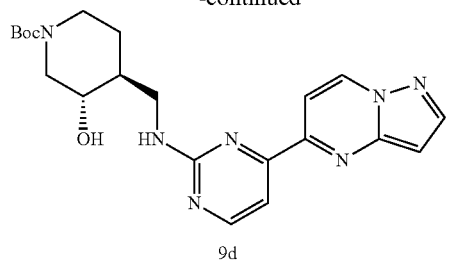

To a stirred solution of mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) (25 mg, 0.01 mmol, 1 eq) in tert-butanol (5 mL) at room temperature was added trans-1-Boc-4-aminomethyl-3-hydroxypiperidine (32 mg, 0.14 mmol, 1.5 eq) and the reaction mixture was stirred at 95° C. for 16 h. After completion of reaction by TLC, reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl trans-3-hydroxyl-4-[4-[pyrazolo[1,5-a]pyrimidin-5-yl]pyrimidin-2-yl]aminomethylpiperidine-1-carboxylate (9d) as yellow solid (28 mg, 68%). TLC system: EtOAc (100%), R$_f$ value: ~0.2.

Synthesis of trans-5-[2-(3-hydroxypiperidin-4-yl)methylaminopyrimidin-4-yl]pyrazolo[1,5-a]pyrimidine trifluoroacetate (Compound I-7)

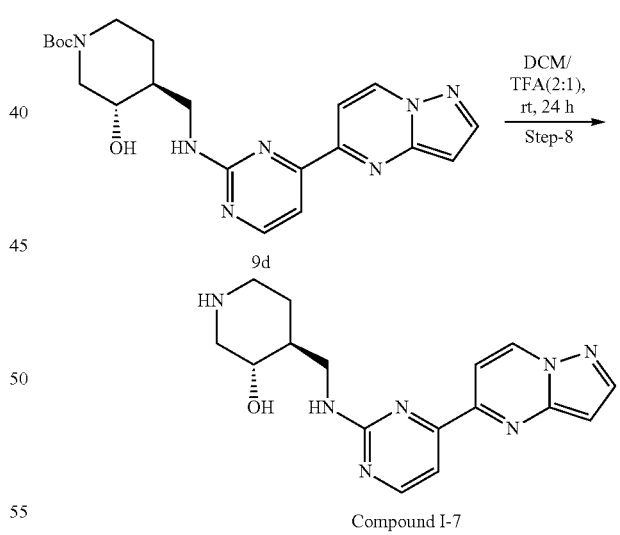

To a stirred solution of tert-butyl trans-3-hydroxyl-4-[4-[pyrazolo[1,5-a]pyrimidin-5-yl]pyrimidin-2-yl]aminomethylpiperidine-1-carboxylate (9d) (25 mg, 0.06 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid appeared in the reaction. The mixture was centrifuged, washed over diethyl ether and dried at room temperature to provide the product trans-5-[2-(3-hydroxypiperidin-4-yl)methylaminopyrimidin-4-yl]pyrazolo[1,5-a]pyrimidine Trifluoroacetate (Compound I-7) as yellow solid (25 mg, 96%); ¹HNMR (400 MHz, MeOD-d4) δ 9.03 (d, J=7.3 Hz, 1H), 8.47 (d, J=5.4 Hz, 1H), 8.26 (s, 1H), 8.04 (d, J=7.3 Hz, 1H), 7.75 (d, J=5.4 Hz, 1H), 6.87 (s, 1H), 3.89 (broad, 1H), 3.72-3.63 (m, 2H), 3.48-3.34 (m, 2H), 3.02-2.96 (m, 1H), 2.87-2.81 (m, 1H), 2.19-2.15 (m, 1H), 2.01-1.96 (m, 1H), 1.68-1.60 (m, 1H); HRMS (ESI) m/z: [M+H]⁺ calcd for $C_{16}H_{19}N_7O$, 326.1724. found 326.1729.

Example 8

Synthesis of Compound I-8

A precursor 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) was prepared according to the syntheses described in EXAMPLE 1 following the steps 1-2 and EXAMPLE 7 following the steps 3-6.

Synthesis of tert-butyl trans-4-[4-[pyrazolo[1,5-a]pyrimidin-5-yl]pyrimidin-2-yl]aminopiperidine-1-carboxylate (9e)

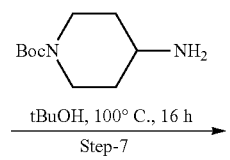

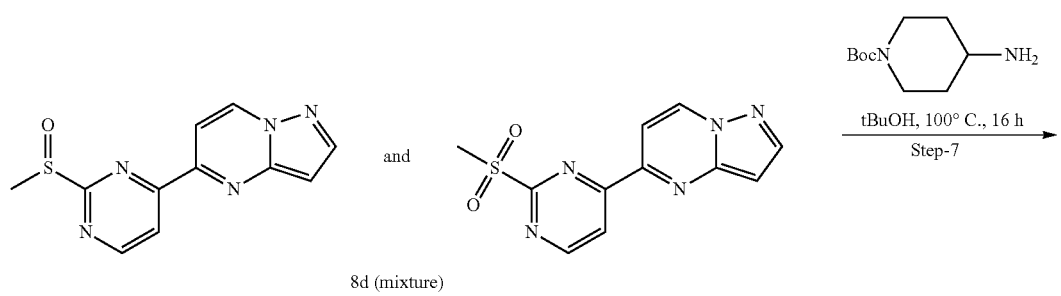

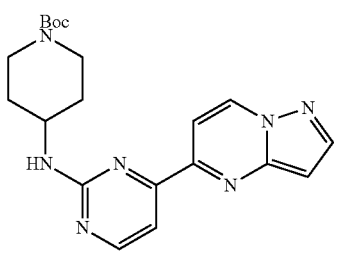 [SMILES: c1cc(-c2ccn3nccc3n2)nc(NC2CCNCC2)n1]

To a stirred solution of mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine(8d) (25 mg, 0.10 mmol, 1 eq) in tert-butanol (5 mL) at room temperature was added tert-Butyl 4-aminopiperidine-1-carboxylate (28 mg, 0.14 mmol, 1.5 eq) and the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl trans-4-[4-[pyrazolo[1,5-a]pyrimidin-5-yl]pyrimidin-2-yl]aminopiperidine-1-carboxylate (9e) as yellow solid (25 mg, 66%). TLC system: Hexane:EtOAc (1:1), $R_f$ value: ~0.2.

Synthesis of trans-5-[2-(piperidin-4-yl)aminopyrimidin-4-yl]pyrazolo[1,5-a]pyrimidine trifluoroacetate (Compound I-8)

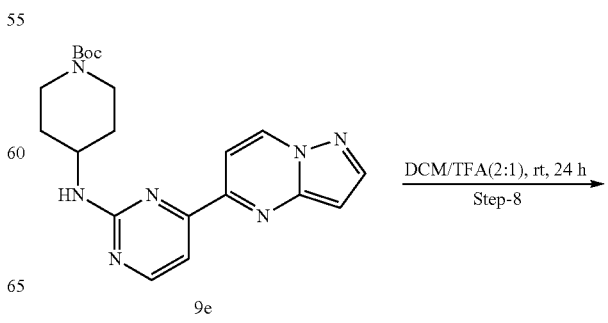

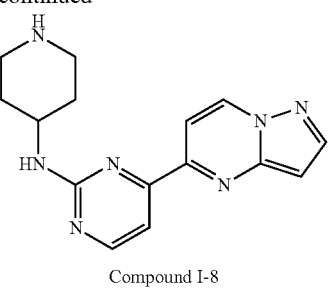

Compound I-8

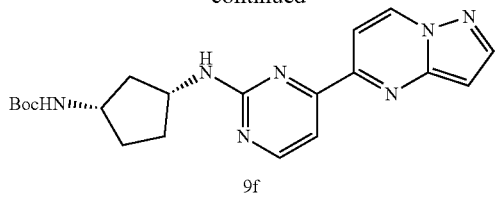

9f

To a stirred solution of tert-butyl trans-4-[4-[pyrazolo[1,5-a]pyrimidin-5-yl]pyrimidin-2-yl]aminopiperidine-1-carboxylate (9e) (25 mg, 0.06 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, trans-5-[2-(piperidin-4-yl)aminopyrimidin-4-yl]pyrazolo[1, 5-a]pyrimidine Trifluoroacetate (Compound I-8) as yellow solid (20 mg, 77%). $^1$HNMR (400 MHz, MeOD-d4) δ 9.01 (d, J=7.3 Hz, 1H), 8.50 (d, J=5.2 Hz, 1H), 8.24 (d, J=2.1 Hz, 1H), 8.02 (d, J=7.3 Hz, 1H), 7.72 (d, J=5.2 Hz, 1H), 6.84 (d, J=2.1 Hz, 1H), 4.27 (s, 1H), 3.51-3.48 (m, 2H), 3.26-3.19 (m, 2H), 2.35-2.31 (m, 2H), 1.92-1.83 (m, 2H); HRMS (ESI) m/z: [M+H]$^+$ calcd for $C_{15}H_{17}N_7$, 296.1618. found 296.1609.

To a stirred solution of mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) (25 mg, 0.10 mmol, 1 eq) in DMSO (5 mL) at room temperature was added (1S,3R)-3-amino-1-(BOC-amino)cyclopentane (28 mg, 0.14 mmol, 1.5 eq) and cesium fluoride (21 mg, 0.14 mmol, 1.5 eq). Then the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3R)-[3-[4-[pyrazolo[1,5-a]pyrimidin-5-yl]pyrimidin-2-yl]aminocyclopentan-1-yl]aminocarboxylate (9f) as yellow solid (22 mg, 58%). TLC system: Hexane:EtOAc (1:1), R$_f$ value: ~0.2.

Example 9

Synthesis of Compound I-9

A precursor 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) was prepared according to the syntheses described in EXAMPLE 1 following the steps 1-2 and EXAMPLE 7 following the steps 3-6.

Synthesis of tert-butyl (1S, 3R)-[3-[4-[pyrazolo[1,5-a]pyrimidin-5-yl]pyrimidin-2-yl]aminocyclopentan-1-yl]aminocarboxylate (9f)

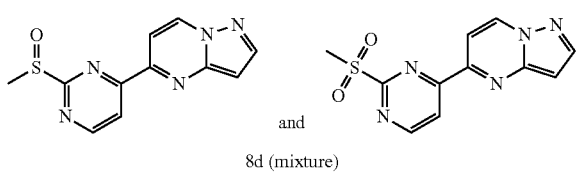

8d (mixture)

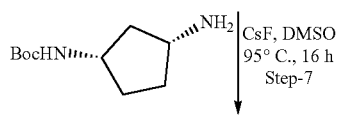

Synthesis of (1S, 3R)-[3-[4-[pyrazolo[1,5-a]pyrimidin-5-yl]pyrimidin-2-yl]aminocyclopentan-1-yl]-1,3-diamine Trifluoroacetate (Compound I-9)

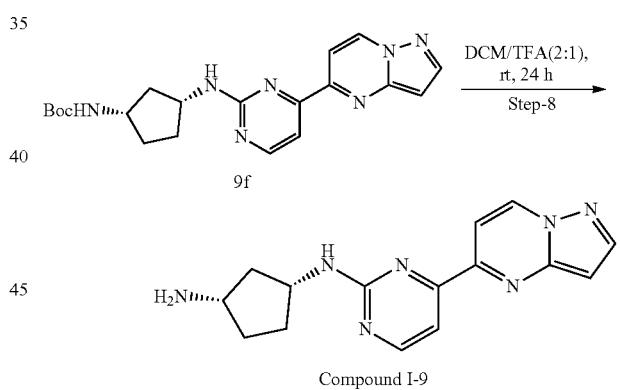

Compound I-9

To a stirred solution of tert-butyl (1S, 3R)-[3-[4-[pyrazolo[1,5-a]pyrimidin-5-yl]pyrimidin-2-yl]aminocyclopentan-1-yl]aminocarboxylate (9f) (20 mg, 0.05 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid appeared in the reaction. The mixture was centrifuged, washed over diethyl ether and dried at room temperature to provide the product, (1S, 3R)-[3-[4-[pyrazolo[1,5-a]pyrimidin-5-yl]pyrimidin-2-yl]aminocyclopentan-1-yl]-1,3-diamine Trifluoroacetate (Compound I-9) as yellow solid (20 mg, 100%). $^1$HNMR (400 MHz, MeOD-d4) δ 9.03 (d, J=7.3 Hz, 1H), 8.48 (d, J=5.5 Hz, 1H), 8.25 (d, J=2.1 Hz, 1H), 8.00 (d, J=7.3 Hz, 1H), 7.75 (d, J=5.5 Hz, 1H), 6.86 (d, J=2.1 Hz, 1H), 4.51-4.48 (m, 1H), 3.74-3.70 (m, 1H), 2.76-2.69 (m, 1H), 2.28-2.17 (m, 2H), 1.98-1.86 (m, 2H), 1.75-1.68 (m, 1H); HRMS (ESI) m/z: [M+H]$^+$ calcd for $C_{15}H_{17}N_7$, 296.1618. found 296.1616.

Example 10

Synthesis of Compound I-10

A precursor 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8d) was prepared according to the syntheses described in EXAMPLE 1 following the steps 1-4 and EXAMPLE 7 following the steps 5-6.

Synthesis of trans-N$^1$-[4-[pyrazolo[1,5-a]pyrimidin-5-yl]pyrimidin-2-yl]-N$^4$-(tetrahydro-2H-pyran-4-yl) cyclohexane-1,4-diamine (Compound I-10)

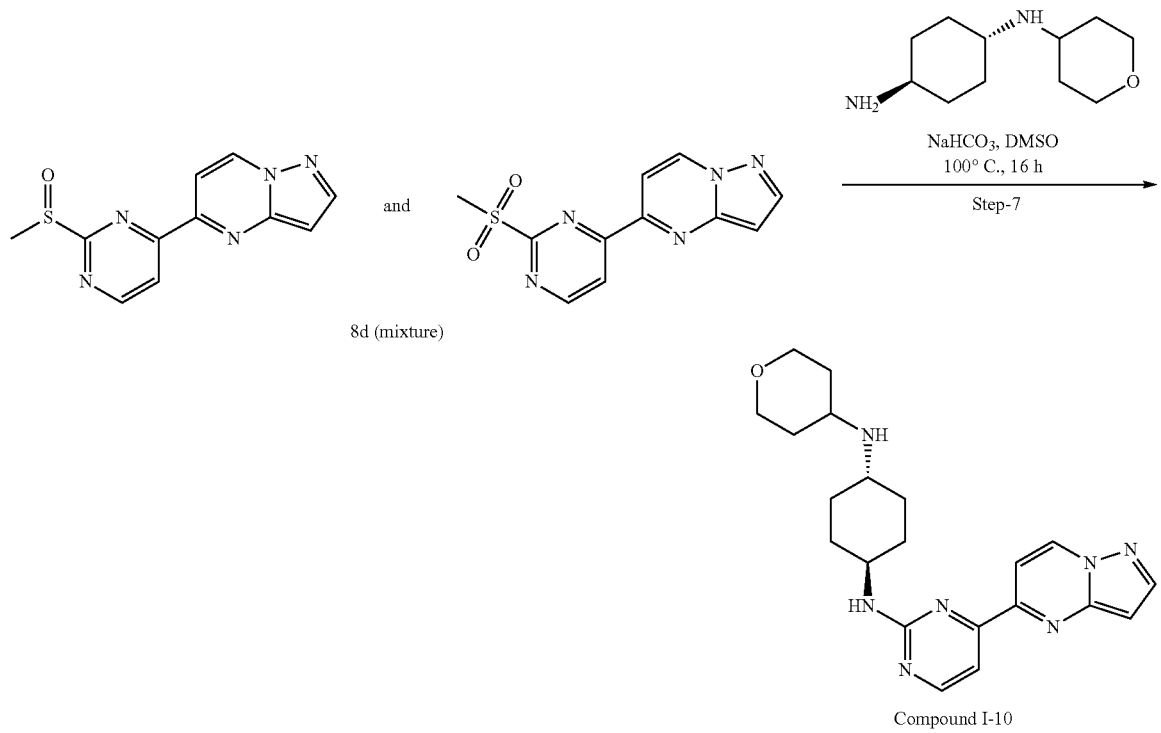

To a stirred solution of mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) (26 mg, 0.10 mmol, 1 eq) and (1R*, 4R*)—N1-(tetrahydro-2H-pyran-4-yl)cyclohexane-1,4-diamine dihydrochloride (41 mg, 0.15 mmol, 1.5 eq) in DMSO (5 mL) at room temperature was added sodium bicarbonate (NaHCO$_3$) (34 mg, 0.40 mmol, 4 eq) and the reaction mixture was stirred at 100° C. for 16 h. After completion of reaction by TLC, reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford trans-N$^1$-[4-[pyrazolo[1,5-a]pyrimidin-5-yl]pyrimidin-2-yl]-N$^4$-(tetrahydro-2H-pyran-4-yl)cyclohexane-1,4-diamine (Compound I-10) as yellow solid (4 mg, 8%). TLC system: MeOH (100%), R$_f$ value: ~0.1; $^1$HNMR (400 MHz, MeOD-d4) δ 8.97 (d, J=7.3 Hz, 1H), 8.41 (d, J=5.1 Hz, 1H), 8.20 (d, J=2.0 Hz, 1H), 7.96 (d, J=7.3 Hz, 1H), 7.57 (d, J=5.1 Hz, 1H), 6.79 (d, J=2.0 Hz, 1H), 3.99-3.95 (s, 2H), 3.90-3.85 (m, 1H), 3.47-3.41 (m, 2H), 3.06-3.00 (m, 1H), 2.89-2.82 (m, 1H), 2.19-2.15 (m, 2H), 2.09-2.05 (m, 2H), 1.91-1.88 (m, 2H), 1.51-1.36 (m, 6H); HRMS (ESI) m/z: [M+H]$^+$ calcd for $C_{21}H_{27}N_7O$, 394.2350, found 394.2336.

Example 11

Synthesis of Compound I-11

A precursor 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8d) was prepared according to the syntheses described in EXAMPLE 1 following the steps 1-4 and EXAMPLE 7 following the steps 5-6.

Synthesis of tert-butyl (1S, 3S)-[3-[4-[pyrazolo[1,5-a]pyrimidin-5-yl]pyrimidin-2-yl]aminocyclopentan-1-yl]aminocarboxylate (9g)

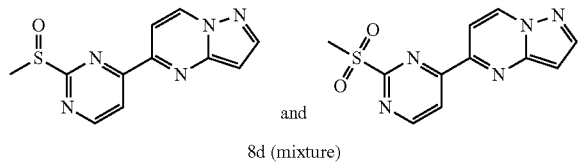

and 8d (mixture)

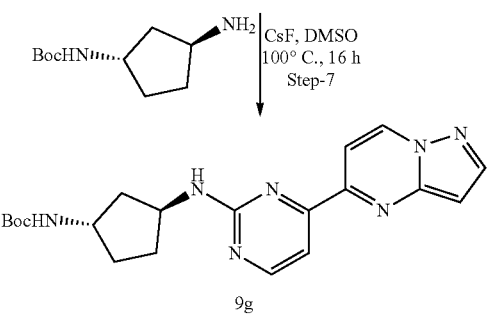

To a stirred solution of mixture of 5-(2-methylsulfinylpyrimidin-4-yl)pyrazolo[1,5-a]pyrimidine and 5-(2-methylsulfonylpyrimidin-4-yl)pyrazolo[1,5-a]pyrimidine (8d) (25 mg, 0.10 mmol, 1 eq) in DMSO (5 mL) at room temperature was added (1S,3S)-3-amino-1-(BOC-amino)cyclopentane (28 mg, 0.14 mmol, 1.5 eq) and cesium fluoride (21 mg, 0.14 mmol, 1.5 eq). Then the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3S)-[3-[4-[pyrazolo[1,5-a]pyrimidin-5-yl]pyrimidin-2-yl]aminocyclopentan-1-yl]aminocarboxylate (9 g) as yellow solid (28 mg, 74%). TLC system: EtOAc:Hexane (1:1), $R_f$ value: ~0.2.

Synthesis of (1S, 3S)-[3-[4-[pyrazolo[1,5-a]pyrimidin-5-yl]pyrimidin-2-yl]aminocyclopentan-1-yl]-1,3-diamine Trifluoroacetate (Compound I-11)

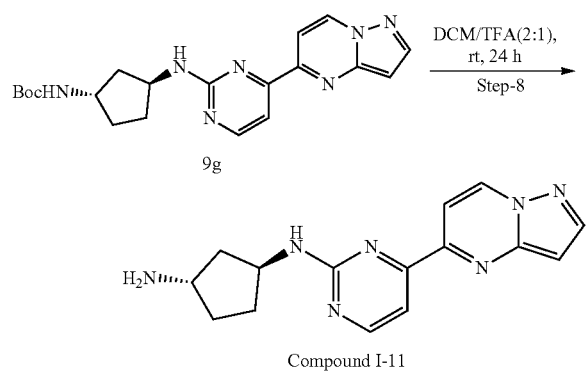

To a stirred solution of tert-butyl (1S, 3S)-[3-[4-[pyrazolo[1,5-a]pyrimidin-5-yl]pyrimidin-2-yl]aminocyclopentan-1-yl]aminocarboxylate (9 g) (25 mg, 0.06 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, (1S, 3S)-[3-[4-[pyrazolo[1,5-a]pyrimidin-5-yl]pyrimidin-2-yl]aminocyclopentan-1-yl]-1,3-diamine Trifluoroacetate (Compound I-11) as yellow solid (30 mg, 94%). $^1$HNMR (400 MHz, CDCl3) δ 9.04 (d, J=7.1 Hz, 1H), 8.50 (d, J=4.9 Hz, 1H), 8.27 (d, J=2.0 Hz, 1H), 8.04 (d, J=7.1 Hz, 1H), 7.74 (d, J=4.9 Hz, 1H), 6.87 (d, J=2.0 Hz, 1H), 4.66 (s, broad, 1H), 3.87-3.83 (m, 1H), 2.41-2.35 (m, 2H), 2.22-2.18 (m, 2H), 1.85-1.73 (m, 2H); HRMS (ESI) m/z: [M+H]$^+$ calcd for $C_{15}H_{17}N_7$, 296.1618. found 296.1609.

Example 12

Synthesis of Compound I-12

A precursor 3-(2-methylsulfanylpyridin-4-yl)-3-oxo-propanoic acid ethyl ester (4) was prepared according to the syntheses described in EXAMPLE 1 following the steps 1 and 2.

Synthesis of 3-methyl-5-(2-methylsulfanylpyrimidin-4-yl)pyrazolo[1,5-a]pyrimidin-7-ol (5 h)

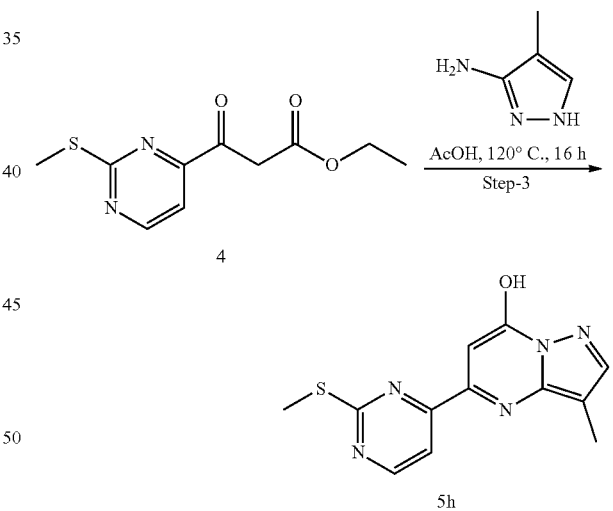

To a stirred solution of 3-(2-methylsulfanyl-pyrimidin-4-yl)-3-oxo-propanoic acid ethyl ester (4) (240 mg, 1.0 mmol, 1.0 eq) in acetic acid (AcOH) (10 mL) at room temperature was added 4-methyl-1H-pyrazol-5-amine (100 mg, 1.2 mmol, 1.2 eq). The reaction mixture was heated to 120° C. for 16 h. After the reaction mixture was then evaporated to remove the AcOH, water was added. The mixture was extracted with ethyl acetate. And the organic layer was washed with brine solution, dried over sodium sulfate and concentrated to provide crude 3-methyl-5-(2-methylsulfanylpyrimidin-4-yl)pyrazolo[1,5-a]pyrimidin-7-ol (5 h) (273 mg, Yield: 100%). TLC system: DCM:MeoH (10:1), $R_f$ value: ~0.3.

Synthesis of 7-chloro-3-methyl-5-(2-methylsulfanylpyrimidin-4-yl)pyrazolo[1,5-a]pyrimidine (6 h)

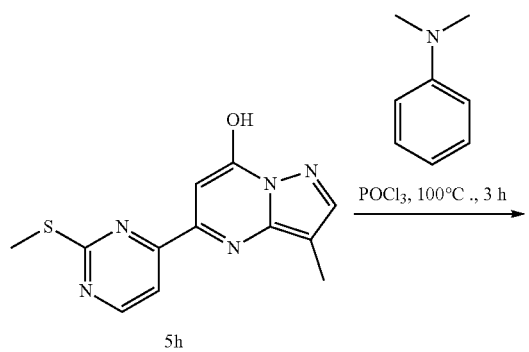

To a stirred solution of 3-methyl-5-(2-methylsulfanylpyrimidin-4-yl)pyrazolo[1,5-a]pyrimidin-7-ol (5 h) (273 mg, 1.0 mmol, 1.0 eq) in Phosphorus (V) oxychloride (POCl$_3$) (5 mL) at room temperature was added N,N-dimethylaniline (267 mg, 2.2 mmol, 2.2 eq). The reaction mixture was heated to 100° C. for 3 h. After the reaction mixture was added to ice dropwise, aqueous saturated NaHCO$_3$ was added to adjust pH 7-8. The mixture was extracted with ethyl acetate, and then the organic layer was washed with brine solution, dried over sodium sulfate and concentrated to provide the product which was purified by combiflash chromatography (4 g column) to afford 7-chloro-3-methyl-5-(2-methylsulfanylpyrimidin-4-yl)pyrazolo[1,5-a]pyrimidine (6 h) as yellow solid (260 mg, Yield: 89%). TLC system: Hexane:EtOAc (4:1), R$_f$ value: ~0.3.

Synthesis of 3-methyl-5-(2-methylsulfanylpyrimidin-4-yl)pyrazolo[1,5-a]pyrimidine (7 h)

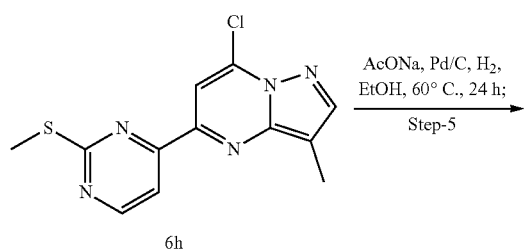

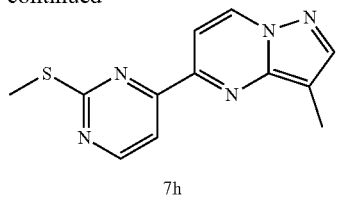

To a stirred solution of 7-chloro-3-methyl-5-(2-methylsulfanylpyrimidin-4-yl)pyrazolo[1,5-a]pyrimidine (6 h) (260 mg, 0.89 mmol, 1.0 eq) in ethanol (10 mL) at room temperature was added sodium acetate (146 mg, 1.78 mmol, 2.0 eq) and 10% Pd/C (26 mg, 10% of 6 h). The reaction mixture was stirred under an atmosphere of H$_2$ at 60° C. for 24 h. The mixture was filtered over Celite® (i.e., diatomaceous earth), washed with ethyl acetate, dried over sodium sulfate and then concentrated to provide the product which was purified by Combiflash Chromatography (4 g column) to afford 3-methyl-5-(2-methylsulfanylpyrimidin-4-yl)pyrazolo[1,5-a]pyrimidine (7 h) (117 mg, Yield: 51%). TLC system: Hexane:EtOAc (2:1), R$_f$ value: ~0.3.

Synthesis of Mixture of 3-methyl-5-(2-methylsulfinylpyrimidin-4-yl)pyrazolo[1,5-a]pyrimidine and 3-methyl-5-(2-methylsulfonylpyrimidin-4-yl)pyrazolo[1,5-a]pyrimidine (8 h)

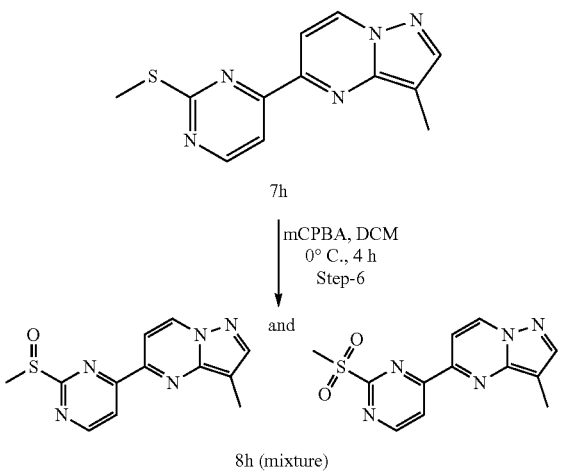

To a stirred solution of 3-methyl-5-(2-methylsulfanylpyrimidin-4-yl)pyrazolo[1,5-a]pyrimidine (7 h) (110 mg, 0.43 mmol, 1.0 eq) in DCM (4 mL) cooled to 0° C. and added 3-chloroperbenzoic acid (mCPBA) (purity, 77%) (126 mg, 0.56 mmol, 1.3 eq). The reaction mixture was stirred at 0° C. for 4 h. After completion of reaction by TLC, the reaction mixture was quenched with sat aq. NaHCO$_3$ solution (10 mL) and extracted with ethyl acetate. The combined organic layers were washed with brine solution, dried over sodium sulfate and concentrated to afford crude mixture of 3-methyl-5-(2-methylsulfinylpyrimidin-4-yl)pyrazolo[1,5-a]pyrimidine and 3-methyl-5-(2-methylsulfonylpyrimidin-4-yl)pyrazolo[1,5-a]pyrimidine (8 h) as a yellow solid (118 mg, yield: 100%). TLC system: EtOAc (100%) R$_f$ value: ~0.01 and 0.4.

Synthesis of tert-butyl (1S, 3S)-[3-[4-[3-methylpyrazolo[1,5-a]pyrimidin-5-yl]pyrimidin-2-yl]aminocyclopentan-1-yl]aminocarboxylate (9 h)

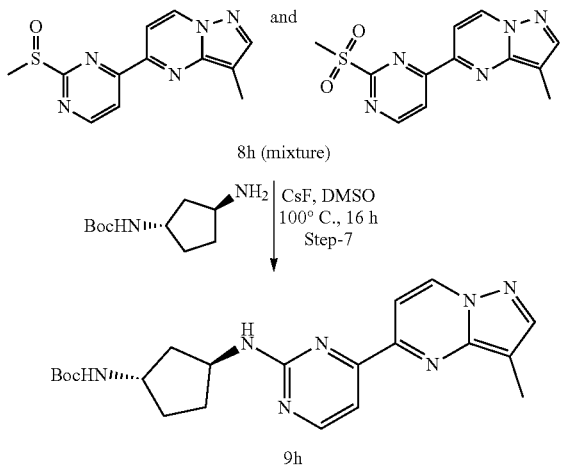

8h (mixture)

9h

To a stirred solution of mixture of 3-methyl-5-(2-methylsulfinylpyrimidin-4-yl)pyrazolo[1,5-a]pyrimidine and 3-methyl-5-(2-methylsulfonylpyrimidin-4-yl)pyrazolo[1,5-a]pyrimidine (8 h) (27 mg, 0.10 mmol, 1 eq) in DMSO (5 mL) at room temperature was added (1S,3S)-3-amino-1-(BOC-amino)cyclopentane (30 mg, 0.15 mmol, 1.5 eq) and cesium fluoride (23 mg, 0.15 mmol, 1.5 eq). Then the reaction mixture was stirred at 95° C. for 16 h. After completion of reaction by TLC, reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3S)-[3-[4-[3-methylpyrazolo[1,5-a]pyrimidin-5-yl]pyrimidin-2-yl]aminocyclopentan-1-yl]aminocarboxylate (9 h) as yellow solid (22 mg, 54%). TLC system: Hexane:EtOAc (1:1), $R_f$ value: ~0.2.

Synthesis of (1S, 3S)-[3-[4-[3-methylpyrazolo[1,5-a]pyrimidin-5-yl]pyrimidin-2-yl]aminocyclopentan-1-yl]-1,3-diamine Trifluoroacetate (Compound I-12)

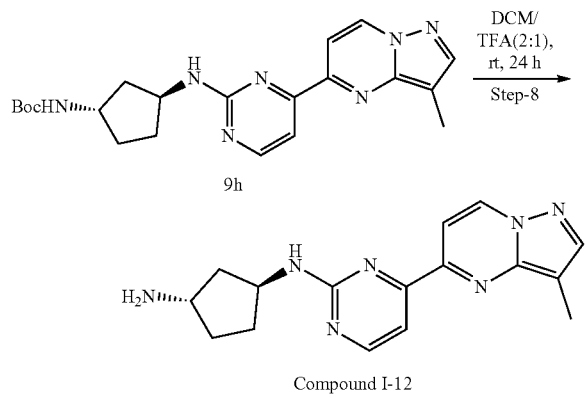

Compound I-12

To a stirred solution of tert-butyl (1S, 3S)-[3-[4-[3-methylpyrazolo[1,5-a]pyrimidin-5-yl]pyrimidin-2-yl]aminocyclopentan-1-yl]aminocarboxylate (9 h) (22 mg, 0.05 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, (1S, 3S)-[3-[4-[3-methylpyrazolo[1,5-a]pyrimidin-5-yl]pyrimidin-2-yl]aminocyclopentan-1-yl]-1,3-diamine Trifluoroacetate (Compound I-12) as yellow solid (29 mg, 9100%). $^1$HNMR (400 MHz, MeOD-d4) δ 8.90 (d, J=7.3 Hz, 1H), 8.47 (d, J=5.3 Hz, 1H), 8.08 (s, 1H), 7.96 (d, J=7.3 Hz, 1H), 7.76 (d, J=5.3 Hz, 1H), 4.66-4.59 (m, 1H), 3.86-3.80 (m, 1H), 2.44 (s, 3H), 2.40-2.32 (m, 2H), 2.20-2.16 (m, 2H), 1.81-1.71 (m, 2H); HRMS (ESI) m/z: [M+H]$^+$ calcd for $C_{16}H_{19}N_7$, 310.1775, found: 310.1730.

Example 13

Synthesis of Compound I-13

A precursor 3-(2-methylsulfanylpyridin-4-yl)-3-oxo-propanoic acid ethyl ester (4) was prepared according to the syntheses described in EXAMPLE 1 following the steps 1 and 2.

Synthesis of 2-methyl-5-(2-methylsulfanylpyrimidin-4-yl)pyrazolo[1,5-a]pyrimidin-7-ol (5i)

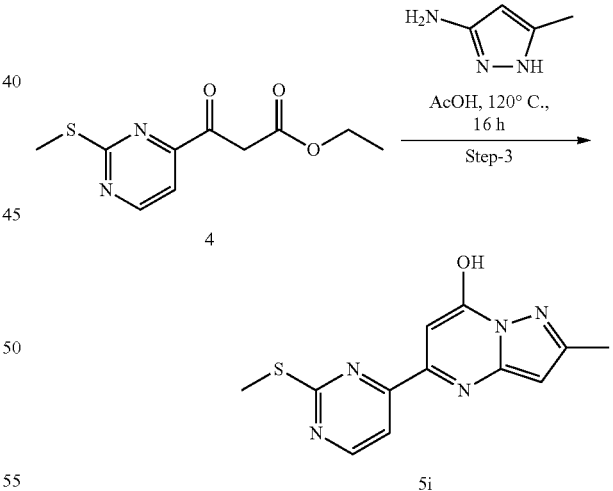

5i

To a stirred solution of 3-(2-methylsulfanyl-pyrimidin-4-yl)-3-oxo-propanoic acid ethyl ester (4) (240 mg, 1.0 mmol, 1.0 eq) in acetic acid (AcOH) (10 mL) at room temperature was added 5-methyl-1H-pyrazol-5-amine (100 mg, 1.2 mmol, 1.2 eq). The reaction mixture was heated to 120° C. for 16 h. After the reaction mixture was then evaporated to remove the AcOH, water was added. The mixture was extracted with ethyl acetate. And the organic layer was washed with brine solution, dried over sodium sulfate and concentrated to provide crude 2-methyl-5-(2-methylsulfanylpyrimidin-4-yl)pyrazolo[1,5-a]pyrimidin-7-ol (5i) (273 mg, Yield: 100%). TLC system: DCM:MeOH (10:1), $R_f$ value: ~0.3.

Synthesis of 7-chloro-2-methyl-5-(2-methylsulfanyl-pyrimidin-4-yl)pyrazolo[1,5-a]pyrimidine (6i)

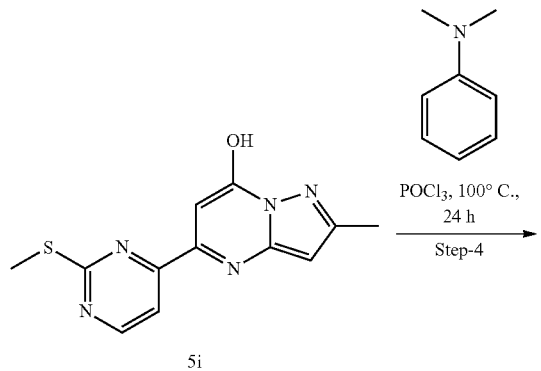

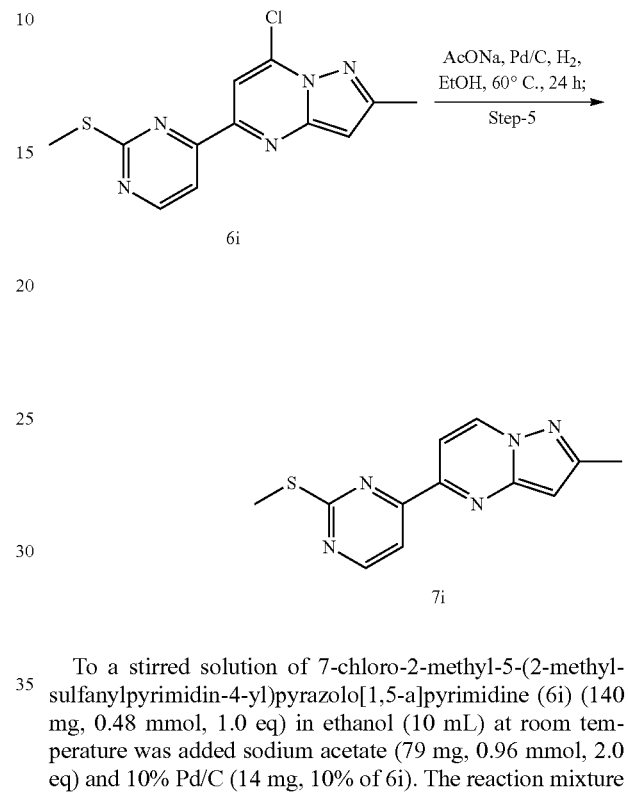

To a stirred solution of 2-methyl-5-(2-methylsulfanylpyrimidin-4-yl)pyrazolo[1,5-a]pyrimidin-7-ol (5i) (273 mg, 1.0 mmol, 1.0 eq) in Phosphorus (V) oxychloride (POCl₃) (5 mL) at room temperature was added N,N-dimethylaniline (267 mg, 2.2 mmol, 2.2 eq). The reaction mixture was heated to 100° C. for 3 h. After the reaction mixture was added to ice dropwise, aqueous saturated NaHCO₃ was added to adjust pH 7-8. The mixture was extracted with ethyl acetate, and then the organic layer was washed with brine solution, dried over sodium sulfate and concentrated to provide the product which was purified by Combiflash Chromatography (4 g column) to afford 7-chloro-2-methyl-5-(2-methylsulfanyl-pyrimidin-4-yl)pyrazolo[1,5-a]pyrimidine (6i) as yellow solid (140 mg, Yield: 48%). TLC system: Hexane:EtOAc (4:1), $R_f$ value: ~0.3.

Synthesis of 2-methyl-5-(2-methylsulfanylpyrimidin-4-yl)pyrazolo[1,5-a]pyrimidine (7i)

To a stirred solution of 7-chloro-2-methyl-5-(2-methylsulfanylpyrimidin-4-yl)pyrazolo[1,5-a]pyrimidine (6i) (140 mg, 0.48 mmol, 1.0 eq) in ethanol (10 mL) at room temperature was added sodium acetate (79 mg, 0.96 mmol, 2.0 eq) and 10% Pd/C (14 mg, 10% of 6i). The reaction mixture was stirred under an atmosphere of H₂ at 60° C. for 24 h. The mixture was filtered over Celite® (i.e., diatomaceous earth), washed with ethyl acetate, dried over sodium sulfate and then concentrated to provide the product which was purified by Combiflash Chromatography (4 g column) to afford 2-methyl-5-(2-methylsulfanylpyrimidin-4-yl)pyrazolo[1,5-a]pyrimidine (7i) (88 mg, Yield: 71%). TLC system: Hexane:EtOAc (2:1), $R_f$ value: ~0.3.

Synthesis of Mixture of 2-methyl-5-(2-methylsulfinylpyrimidin-4-yl)pyrazolo[1,5-a]pyrimidine and 2-methyl-5-(2-methylsulfonylpyrimidin-4-yl)pyrazolo[1,5-a]pyrimidine (8i)

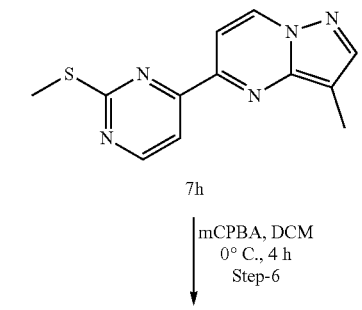

mCPBA, DCM
0° C., 4 h
Step-6

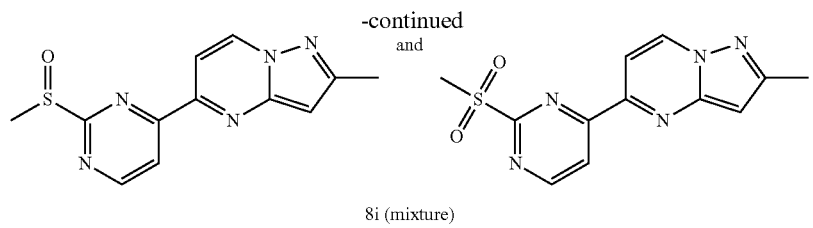

8i (mixture)

To a stirred solution of 2-methyl-5-(2-methylsulfanylpyrimidin-4-yl)pyrazolo[1,5-a]pyrimidine (7i) (80 mg, 0.31 mmol, 1.0 eq) in DCM (4 mL) cooled to 0° C. and added 3-chloroperbenzoic acid (mCPBA) (purity, 77%) (90 mg, 0.40 mmol, 1.3 eq). The reaction mixture was stirred at 0° C. for 4 h. After completion of reaction by TLC, reaction mixture was quenched with sat aq. NaHCO₃ solution (10 mL) and extracted with ethyl acetate. The combined organic layers were washed with brine solution, dried over sodium sulfate and concentrated to afford crude mixture of 2-methyl-5-(2-methylsulfinylpyrimidin-4-yl)pyrazolo[1,5-a]pyrimidine and 2-methyl-5-(2-methylsulfonylpyrimidin-4-yl)pyrazolo[1,5-a]pyrimidine (8i) as a yellow solid (85 mg, yield: 100%). TLC system: EtOAc (100%) R$_f$ value: ~0.01 and 0.4.

Synthesis of tert-butyl (1S, 3S)-[3-[4-[2-methylpyrazolo[1,5-a]pyrimidin-5-yl]pyrimidin-2-yl]aminocyclopentan-1-yl]aminocarboxylate (9i)

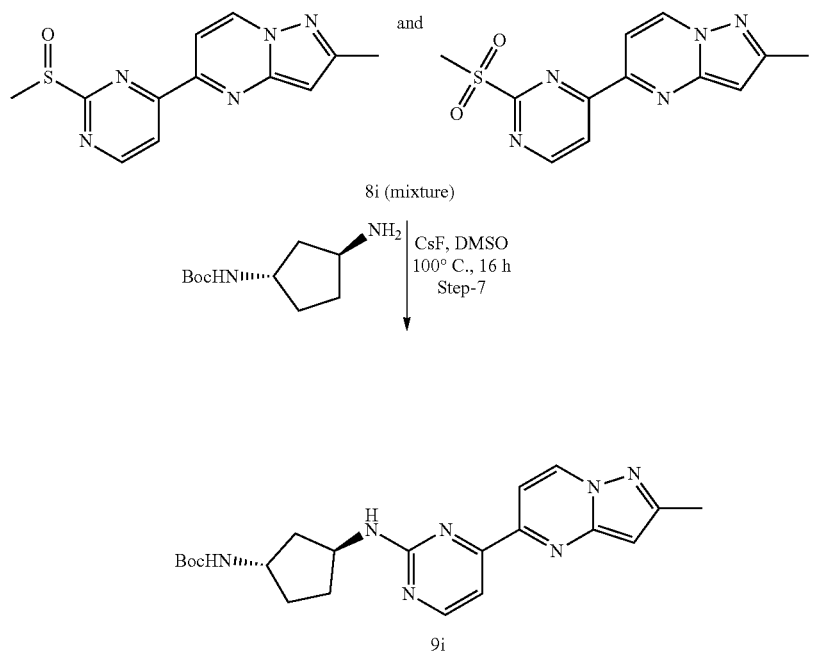

To a stirred solution of mixture of 2-methyl-5-(2-methylsulfinylpyrimidin-4-yl)pyrazolo[1,5-a]pyrimidine and 2-methyl-5-(2-methylsulfonylpyrimidin-4-yl)pyrazolo[1,5-a]pyrimidine (8i) (25 mg, 0.10 mmol, 1 eq) in DMSO (5 mL) at room temperature was added (1S,3S)-3-amino-1-(BOC-amino)cyclopentane (28 mg, 0.14 mmol, 1.5 eq) and cesium fluoride (21 mg, 0.14 mmol, 1.5 eq). Then the reaction mixture was stirred at 95° C. for 16 h. After completion of the reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3S)-[3-[4-[2-methylpyrazolo[1,5-a]pyrimidin-5-yl]pyrimidin-2-yl]aminocyclopentan-1-yl]aminocarboxylate (9i) as yellow solid (14 mg, 38%). TLC system: Hexane:EtOAc (1:1), R$_f$ value: ~0.2.

Synthesis of (1S, 3S)-[3-[4-[2-methylpyrazolo[1,5-a]pyrimidin-5-yl]pyrimidin-2-yl]aminocyclopentan-1-yl]-1,3-diamine Trifluoroacetate (Compound I-13)

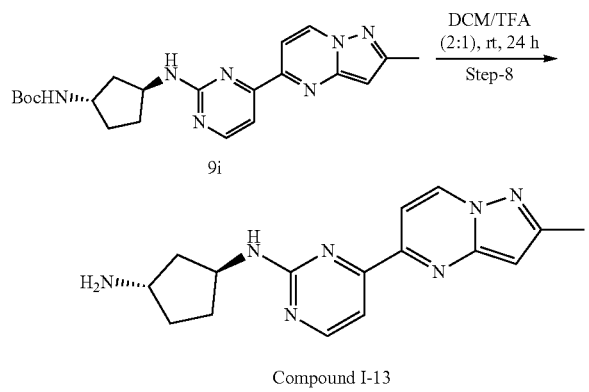

9i

Compound I-13

To a stirred solution of tert-butyl (1S, 3S)-[3-[4-[2-methylpyrazolo[1,5-a]pyrimidin-5-yl]pyrimidin-2-yl]aminocyclopentan-1-yl]aminocarboxylate (9i) (11 mg, 0.027 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, (1S, 3S)-[3-[4-[2-methylpyrazolo[1,5-a]pyrimidin-5-yl]pyrimidin-2-yl]aminocyclopentan-1-yl]-1,3-diamine Trifluoroacetate (Compound I-13) as yellow solid (8 mg, 53%). $^1$HNMR (400 MHz, MeOD-d4) δ 8.87 (d, J=7.2 Hz, 1H), 8.46 (d, J=5.2 Hz, 1H), 7.93 (d, J=7.2 Hz, 1H), 7.65 (d, J=5.2 Hz, 1H), 6.63 (s, 1H), 4.64-4.57 (m, 1H), 3.84-3.79 (m, 1H), 2.53 (s, 3H), 2.37-2.31 (m, 2H), 2.18-2.15 (m, 2H), 1.80-1.70 (m, 2H); HRMS (ESI) m/z: [M+H]$^+$ calcd for $C_{16}H_{19}N_7$, 310.1775, found: 310.1726.

Example 14

Synthesis of Compound I-14

A precursor 3-isopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8c) was prepared according to the syntheses described in EXAMPLE 1 following the steps 1-4 and EXAMPLE 3 following the steps 5-6.

Synthesis of tert-butyl (1S, 3S)-[3-[4-[3-isopropylpyrazolo[1,5-a]pyrimidin-5-yl]pyrimidin-2-yl]aminocyclopentan-1-yl]aminocarboxylate (9j)

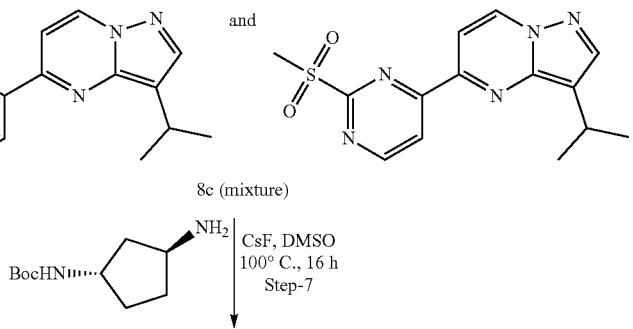

8c (mixture)

CsF, DMSO
100° C., 16 h
Step-7

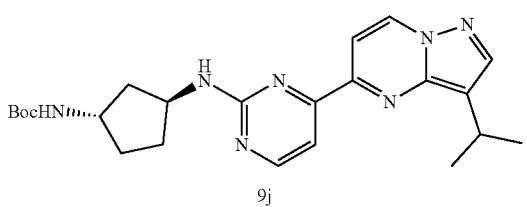

9j

To a stirred solution of mixture of 3-isopropyl-5-(2-methylsulfinylpyrimidin-4-yl)pyrazolo[1,5-a]pyrimidine and 3-isopropyl-5-(2-methylsulfonyl-pyrimidin-4-yl)pyrazolo[1,5-a]pyrimidine (8c) (21 mg, 0.07 mmol, 1 eq) in DMSO (5 mL) at room temperature was added (1S,3S)-3-amino-1-(Boc-amino)cyclopentane (22 mg, 0.11 mmol, 1.5 eq) and cesium fluoride (17 mg, 0.11 mmol, 1.5 eq). Then the reaction mixture was stirred at 95° C. for 16 h. After completion of the reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3S)-[3-[4-[3-isopropylpyrazolo[1,5-a]pyrimidin-5-yl]pyrimidin-2-yl]aminocyclopentan-1-yl]aminocarboxylate (9j) as yellow solid (25 mg, 81%). TLC system: Hexane:EtOAc (1:1), $R_f$ value: ~0.3.

Synthesis of (1S, 3S)-[3-[4-[3-isopropylpyrazolo[1,5-a]pyrimidin-5-yl]pyrimidin-2-yl]aminocyclopentan-1-yl]-1,3-diamine Trifluoroacetate (Compound I-14)

To a stirred solution of tert-butyl (1S, 3S)-[3-[4-[3-isopropylpyrazolo[1,5-a]pyrimidin-5-yl]pyrimidin-2-yl]aminocyclopentan-1-yl]aminocarboxylate (9j) (25 mg, 0.057 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid appeared in the reaction. The mixture was centrifuged, washed over diethyl ether and dried at room temperature to provide the product, (1S, 3S)-[3-[4-[3-isopropylpyrazolo[1,5-a]pyrimidin-5-yl]pyrimidin-2-yl]aminocyclopentan-1-yl]-1,3-diamine Trifluoroacetate (Compound I-14) as yellow solid (25 mg, 81%). $^1$HNMR (400 MHz, MeOD-d4) δ 8.91 (d, J=7.4 Hz, 1H), 8.47 (d, J=5.3 Hz, 1H), 8.11 (s, 1H), 7.96 (d, J=7.4 Hz, 1H), 7.75 (d, J=5.3 Hz, 1H), 4.69-4.61 (m, 1H), 3.86-3.79 (m, 1H), 3.45-3.37 (m, 1H), 2.39-2.32 (m, 2H), 2.20-2.16 (m, 2H), 1.84-1.73 (m, 2H), 1.46 (d, J=7.0 Hz, 6H); HRMS (ESI) m/z [M+H]$^+$ calcd for $C_{18}H_{23}N_7$, 338.2088, found: 338.2037.

Example 15

Synthesis of Compound I-15

A precursor 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a) was prepared according to the syntheses described in EXAMPLE 1 following the steps 1-6.

Synthesis of tert-butyl (1S, 3S)-[3-[4-[3-cyclopropylpyrazolo[1,5-a]pyrimidin-5-yl]pyrimidin-2-yl]aminocyclopentan-1-yl]aminocarboxylate (9k)

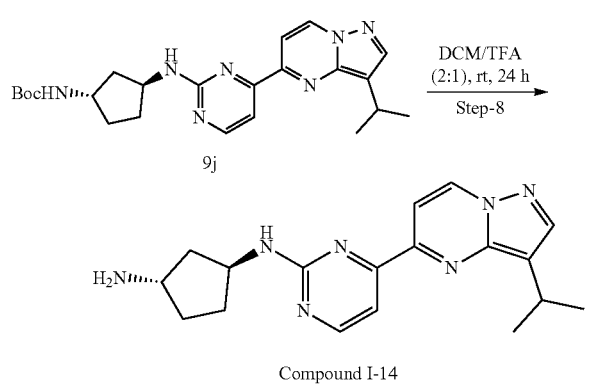

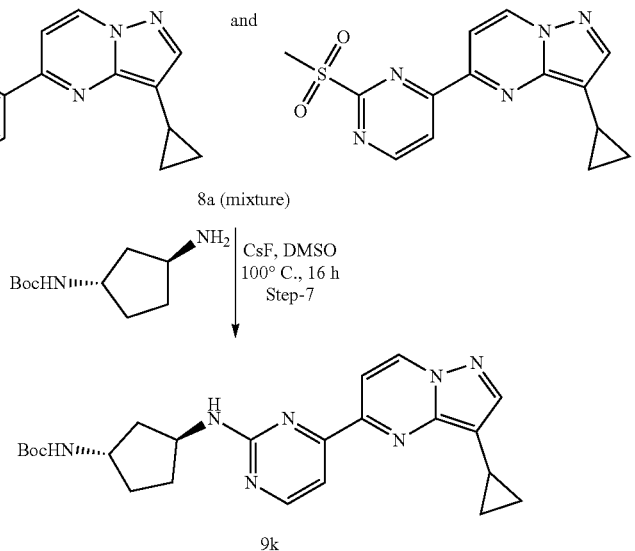

To a stirred solution of mixture of 3-cyclopropyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8a) (20 mg, 0.07 mmol, 1 eq) in DMSO (5 mL) at room temperature was added (1S,3S)-3-amino-1-(BOC-amino)cyclopentane (20 mg, 0.10 mmol, 1.5 eq) and cesium fluoride (15 mg, 0.10 mmol, 1.5 eq). Then the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3S)-[3-[4-[3-cyclopropylpyrazolo[1,5-a]pyrimidin-5-yl]pyrimidin-2-yl]aminocyclopentan-1-yl]aminocarboxylate (9k) as yellow solid (20 mg, 69%). TLC system: EtOAc:Hexane (1:1), $R_f$ value: ~0.2.

Synthesis of (1S, 3S)-[3-[4-[3-cyclopropylpyrazolo[1,5-a]pyrimidin-5-yl]pyrimidin-2-yl]aminocyclopentan-1-yl]-1,3-diamine Trifluoroacetate (Compound I-15)

To a stirred solution of tert-butyl (1S, 3S)-[3-[4-[3-cyclopropylpyrazolo[1,5-a]pyrimidin-5-yl]pyrimidin-2-yl]aminocyclopentan-1-yl]aminocarboxylate (9k) (20 mg, 0.046 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, (1S, 3S)-[3-[4-[3-cyclopropylpyrazolo[1,5-a]pyrimidin-5-yl]pyrimidin-2-yl]aminocyclopentan-1-yl]-1,3-diamine Trifluoroacetate (Compound I-15) as yellow solid (18 mg, 69%). $^1$HNMR (400 MHz, MeOD-d4) δ 8.87 (d, J=7.3 Hz, 1H), 8.46 (d, J=5.3 Hz, 1H), 7.99 (s, 1H), 7.92 (d, J=7.3 Hz, 1H), 7.73 (d, J=5.3 Hz, 1H), 4.65-4.60 (m, 1H), 3.86-3.80 (m, 1H), 2.40-2.32 (m, 2H), 2.20-2.15 (m, 3H), 1.84-1.71 (m, 2H), 1.07-0.99 (m, 4H); HRMS data: HRMS (ESI) m/z [M+H]$^+$ calcd for $C_{18}H_{21}N_7$, 336.1931, found: 336.1914.

Example 16

Synthesis of Compound I-16

A precursor 3-cyclobutyl-5-(2-methylsulfinylpyrimidin-4-yl)pyrazolo[1,5-a]pyrimidine and 3-cyclopropyl-5-(2-methylsulfonylpyrimidin-4-yl)pyrazolo[1,5-a]pyrimidine (8b) was prepared according to the syntheses described in EXAMPLE 1 following the steps 1-4 and EXAMPLE 2 following the steps 5-6.

Synthesis of tert-butyl (1S, 3S)-[3-[4-[3-cyclobutylpyrazolo[1,5-a]pyrimidin-5-yl]pyrimidin-2-yl]aminocyclopentan-1-yl]aminocarboxylate (9l)

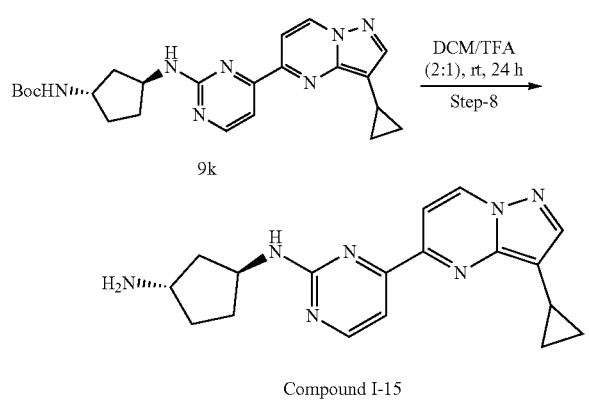

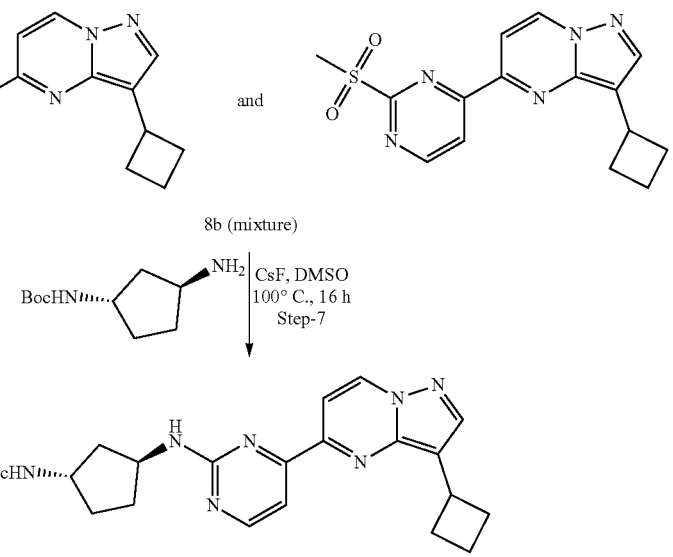

To a stirred solution of mixture of 3-cyclobutyl-5-(2-methylsulfinylpyrimidin-4-yl)pyrazolo[1,5-a]pyrimidine and 3-cyclobutyl-5-(2-methylsulfonylpyrimidin-4-yl)pyrazolo[1,5-a]pyrimidine (8b) (23 mg, 0.07 mmol, 1 eq) in DMSO (5 mL) at room temperature was added (1S,3S)-3-amino-1-(BOC-amino)cyclopentane (22 mg, 0.11 mmol, 1.5 eq) and cesium fluoride (17 mg, 0.11 mmol, 1.5 eq). Then the reaction mixture was stirred at 95° C. for 16 h. After completion of reaction by TLC, the reaction mixture was cooled to room temperature and extracted with ethyl acetate. The organic layer was washed with brine solution, dried over anhydrous sodium sulfate and then concentrated to provide product which was purified by Combiflash Chromatography (4 g column) to afford tert-butyl (1S, 3S)-[3-[4-[3-cyclobutylpyrazolo[1,5-a]pyrimidin-5-yl]pyrimidin-2-yl]aminocyclopentan-1-yl]aminocarboxylate (91) as yellow solid (28 mg, 90%). TLC system: EtOAc:Hexane (1:1), $R_f$ value: ~0.3.

Synthesis of (1S, 3S)-[3-[4-[3-cyclobutylpyrazolo[1,5-a]pyrimidin-5-yl]pyrimidin-2-yl]aminocyclopentan-1-yl]-1,3-diamine Trifluoroacetate (Compound I-16)

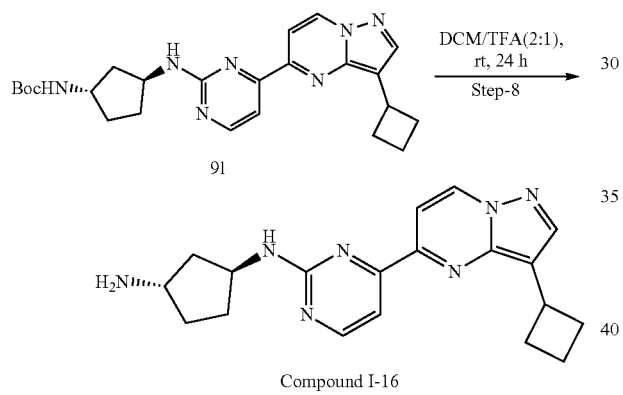

Compound I-16

To a stirred solution of tert-butyl (1S, 3S)-[3-[4-[3-cyclobutylpyrazolo[1,5-a]pyrimidin-5-yl]pyrimidin-2-yl]aminocyclopentan-1-yl]aminocarboxylate (91) (28 mg, 0.06 mmol, 1 eq) in DCM (4 mL) at room temperature was added trifluoroacetic acid (TFA) (2 mL) and the reaction mixture was stirred at room temperature for 24 h. After completion of reaction by TLC, the solvent was removed in vacuum. Then diethyl ether was added to the reaction and a lot of yellow solid will appear in the reaction. The mixture was centrifuged, washed over diethyl ether and dried at room temperature to provide the product, (1S, 3S)-[3-[4-[3-cyclobutylpyrazolo[1,5-a]pyrimidin-5-yl]pyrimidin-2-yl]aminocyclopentan-1-yl]-1,3-diamine Trifluoroacetate (Compound I-16) as yellow solid (27 mg, 75%). $^1$HNMR (400 MHz, MeOD-d4) δ 8.90 (d, J=7.4 Hz, 1H), 8.47 (d, J=5.3 Hz, 1H), 8.17 (s, 1H), 7.95 (d, J=7.4 Hz, 1H), 7.74 (d, J=5.3 Hz, 1H), 4.67-4.60 (m, 1H), 3.98-3.89 (m, 1H), 3.86-3.80 (m, 1H), 2.50-2.44 (m, 4H), 2.40-2.32 (m, 2H), 2.20-2.16 (m, 2H), 2.15-2.10 (m, 1H), 2.06-2.00 (m, 1H), 1.83-1.71 (m, 2H); HRMS data: HRMS (ESI) m/z [M+H]$^+$ calcd for $C_{19}H_{23}N_7$, 350.2088, found: 350.2075.

Example 17

Synthesis of Compound I-17

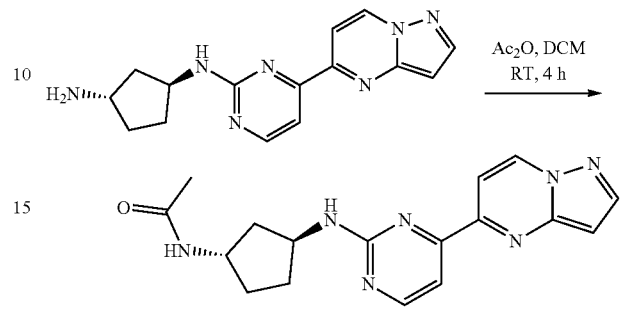

To a stirred solution of (1S,3S)—N1-(4-(pyrazolo[1,5-a]pyrimidin-5-yl)pyrimidin-2-yl)cyclopentane-1,3-diamine (40 mg, 0.14 mmol, 1 eq) in DCM (0.5 mL) at room temperature, was added Ac$_2$O (0.1 mL) and stirred for 4 h. After completion of reaction by TLC, the reaction mixture was concentrated in vacuo, purified by reverse phase column and lyophilized to afford the desired product as white solid (33 mg, yield: 70%). TLC system: MeOH:DCM (10:90), $R_f$ value: ~0.4; LCMS(m/z): 338.2 (M+H)+; $^1$H NMR (400 MHz, DMSO-d$_6$) δ: 9.28 (d, J=7.2 Hz, 1H), 8.49 (d, J=4.8 Hz, 1H), 8.32 (d, J=2.4 Hz, 1H), 7.93-7.90 (br, 2H), 7.52 (d, J=7.2 Hz, 1H), 7.49 (d, J=5.2 Hz, 1H), 6.89 (dd, J=2.4 & 0.8 Hz, 1H), 4.45-4.42 (br, 1H), 4.24-4.15 (m, 1H), 2.19-2.15 (br, 1H), 2.08-2.19 (m, 1H), 1.91-1.82 (m, 2H), 1.79 (s, 3H), 1.58-1.51 (m, 1H), 1.46-1.39 (m, 1H).

Example 18

Synthesis of Compound I-18

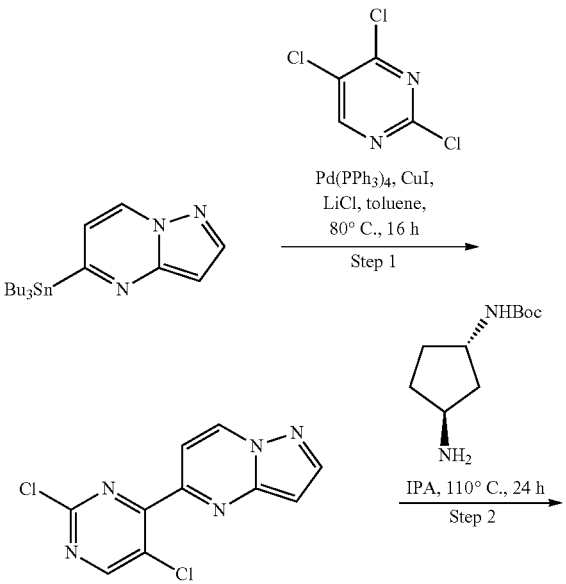

-continued

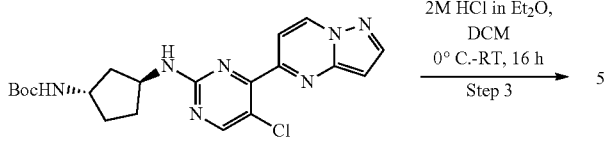

Synthesis of 5-(2,5-dichloropyrimidin-4-yl)pyrazolo[1,5-a]pyrimidine (Step 1)

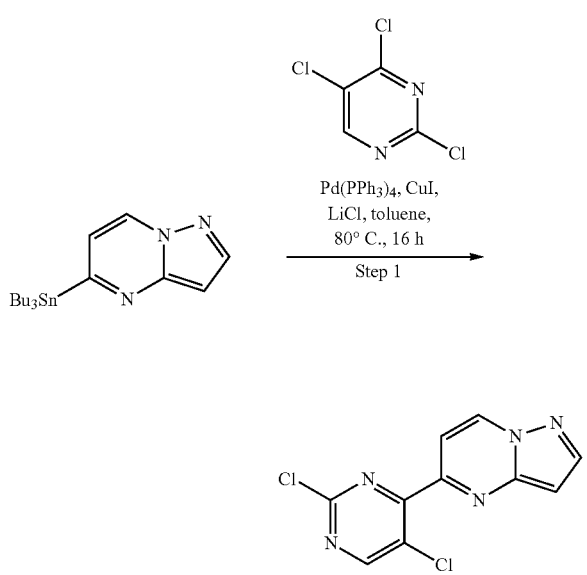

To a stirred solution of 5-(tributylstannyl)pyrazolo[1,5-a]pyrimidine (400 mg, 0.98 mmol, 1 eq) and 2,4,5-trichloropyrimidine (197 mg, 1.08 mmol, 1.1 eq) in toluene (4 mL) at room temperature was added Pd(PPh$_3$)$_4$ (56 mg, 0.05 mmol, 0.05 eq.), CuI (37 mg, 0.19 mmol, 0.2 eq.), LiCl (82 mg, 1.95 mmol, 2 eq.) and stirred at 100° C. for 16 h. After completion of reaction by TLC, the reaction was diluted with water and ethyl acetate, filtered through Celite® (i.e., diatomaceous earth). Organic layer was separated and washed with water, dried over anhydrous Na$_2$SO$_4$, evaporated and purified by silica (100-200 mesh) column (eluent: 0-15% EtOAc in Hexane) to afford 5-(2,5-dichloropyrimidin-4-yl)pyrazolo[1,5-a]pyrimidine as brown solid (150 mg, yield: 57%). TLC system: EtOAc:Hexanes (20:80), R$_f$ value: ~0.3; LCMS(m/z): 266.0 (M+H)+; $^1$H NMR (400 MHz, CDCl$_3$) δ: 8.85 (dd, J=7.2 & 0.8 Hz, 1H), 8.78 (s, 1H), 8.25 (d, J=2.4 Hz, 1H), 7.58 (d, J=7.2 Hz, 1H), 6.90 (d, J=2.4 Hz, 1H).

Synthesis of tert-butyl ((1S,3S)-3-((5-chloro-4-(pyrazolo[1,5-a]pyrimidin-5-yl)pyrimidin-2-yl)amino)cyclopentyl)carbamate (Step 2)

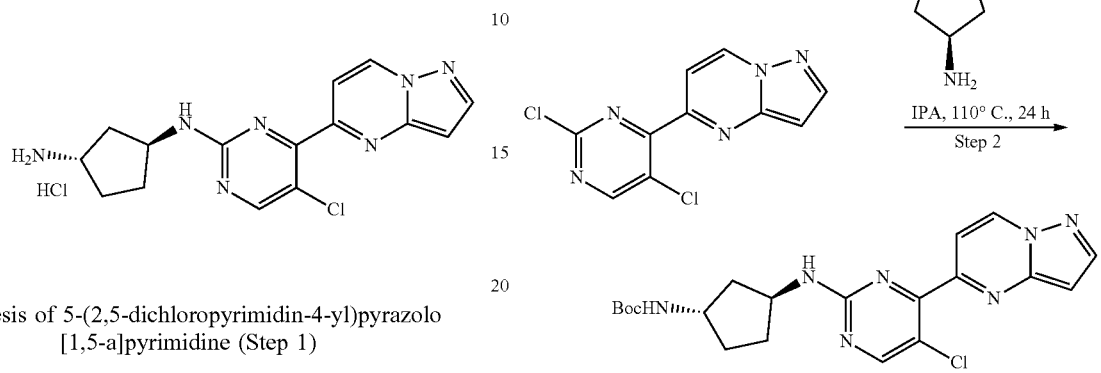

A solution of 5-(2,5-dichloropyrimidin-4-yl)pyrazolo[1,5-a]pyrimidine (140 mg, 0.53 mmol, 1 eq) and tert-butyl ((1S,3S)-3-aminocyclopentyl)carbamate (211 mg, 1.06 mmol, 2 eq) in isopropyl alcohol (2.8 mL) was stirred at 110° C. for 16 h. After completion of reaction by TLC, volatiles removed under vacuum, diluted with water, and extracted with ethyl acetate (3×20 mL). Organic layer was dried over anhydrous Na$_2$SO$_4$, evaporated and purified by silica (100-200 mesh) column (eluent: 0-20% EtOAc in Hexane) to afford tert-butyl((1S,3S)-3-((5-chloro-4-(pyrazolo[1,5-a]pyrimidin-5-yl)pyrimidin-2-yl)amino)cyclopentyl)carbamate as brown solid (140 mg, 61%). TLC system: EtOAc:Hexanes (40:60), R$_f$ value: ~0.25; $^1$H NMR (400 MHz, CDCl$_3$) δ: 8.79 (d, J=7.2 Hz, 1H), 8.40 (s, 1H), 8.21 (d, J=2.4 Hz, 1H), 7.36 (d, J=7.2 Hz, 1H), 6.85 (d, J=2.4 Hz, 1H), 5.28 (d, J=7.2 Hz, 1H), 4.53 (s, 1H), 4.42-4.36 (m, 1H), 4.14 (brs, 1H), 2.30-2.22 (m, 2H), 1.98-1.94 (m, 2H), 1.51-1.47 (m, 2H), 1.44 (s, 9H).

Synthesis of (1S,3S)—N1-(4-(pyrazolo[1,5-a]pyrimidin-5-yl)pyrimidin-2-yl)cyclopentane-1,3-diamine HCl salt (Compound I-18)

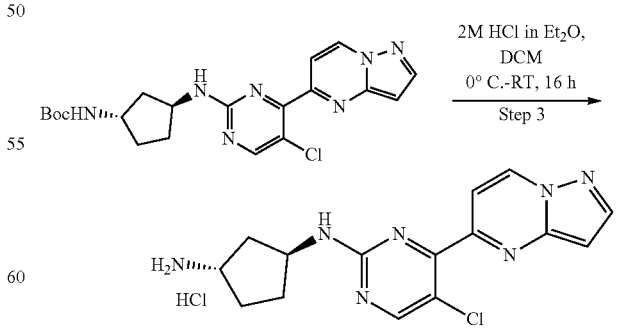

To a stirred solution of tert-butyl ((1S,3S)-3-((5-chloro-4-(pyrazolo[1,5-a]pyrimidin-5-yl)pyrimidin-2-yl)amino)cyclopentyl)carbamate (140 mg, 0.33 mmol, 1 eq) in DCM (1.4 mL) at 0° C. was added 2M HCl in Et$_2$O (0.7 mL, 5 vol)

and stirred at room temperature for 16 h. After completion of reaction by TLC, reaction mixture was evaporated and purified by trituration with n-pentane, ethyl ether and 10% DCM in ethyl ether to afford Compound I-18 as an HCl salt. The compound appeared as yellow solid (80 mg, yield: 74%). TLC system: MeOH:DCM (5:95), R$_f$ value: ~0.2; LCMS (m/z): 330.2 (M+H)+; $^1$H NMR (400 MHz, CD$_3$OD) δ: 9.05 (d, J=7.2 Hz, 1H), 8.47 (s, 1H), 8.27 (d, J=2.4 Hz, 1H), 7.48 (d, J=7.2 Hz, 1H), 6.84 (d, J=2.4 Hz, 1H), 4.54-4.51 (m, 1H), 3.81-3.77 (m, 1H), 2.35-2.26 (m, 2H), 2.12 (d, J=7.2 Hz, 2H), 1.79-1.71 (m, 2H).

Example 19

Synthesis of Compound I-19

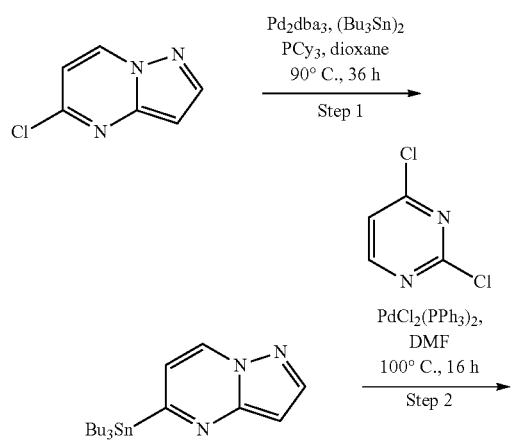

Synthesis of 5-(tributylstannyl)pyrazolo[1,5-a]pyrimidine (Step 1)

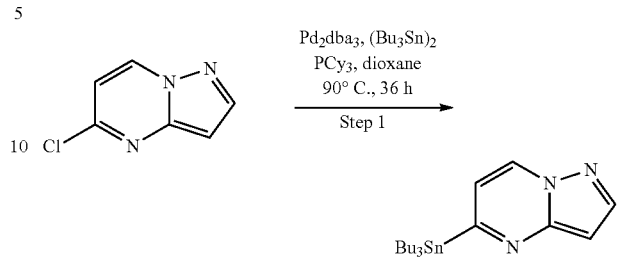

To a stirred solution of 5-chloropyrazolo[1,5-a]pyrimidine (2 g, 13.1 mmol, 1 eq) and bis(tributyltin) (11.2 g, 19.6 mmol, 1.5 eq) in 1,4-dioxane (40 mL) at room temperature, was added PCy$_3$ (360 mg, 1.31 mmol, 0.1 eq.), Pd$_2$(dba)$_3$ (600 mg, 0.66 mmol, 0.05 eq.) and stirred at 90° C. for 36 h. Reaction was not clean observed multiple spots on TLC. Reaction mixture was diluted with water and extracted with ethyl acetate (2×200 mL). Organic layer was dried over anhydrous Na$_2$SO$_4$, concentrated in vacuo and purified by silica (100-200 mesh) column (eluent: 0-10% EtOAc in Hexane) to afford 5-(tributylstannyl)pyrazolo[1,5-a]pyrimidine as yellow oil (700 mg, 17%). TLC system: EtOAc: Hexanes (10:90), R$_f$ value: ~0.6; LCMS(m/z): 410.1 (M+H)+; $^1$H NMR (400 MHz, CDCl$_3$) δ: 8.48 (d, J=6.8 Hz, 1H), 8.05 (d, J=2.4 Hz, 1H), 6.89 (d, J=6.8 Hz, 1H), 6.67 (d, J=2.4 Hz, 1H), 1.67-1.55 (m, 6H), 1.36-1.30 (m, 6H), 1.21-1.17 (m, 6H), 0.94-0.87 (m, 9H).

Synthesis of 5-(2-chloropyrimidin-4-yl)pyrazolo[1,5-a]pyrimidine (Step 2)

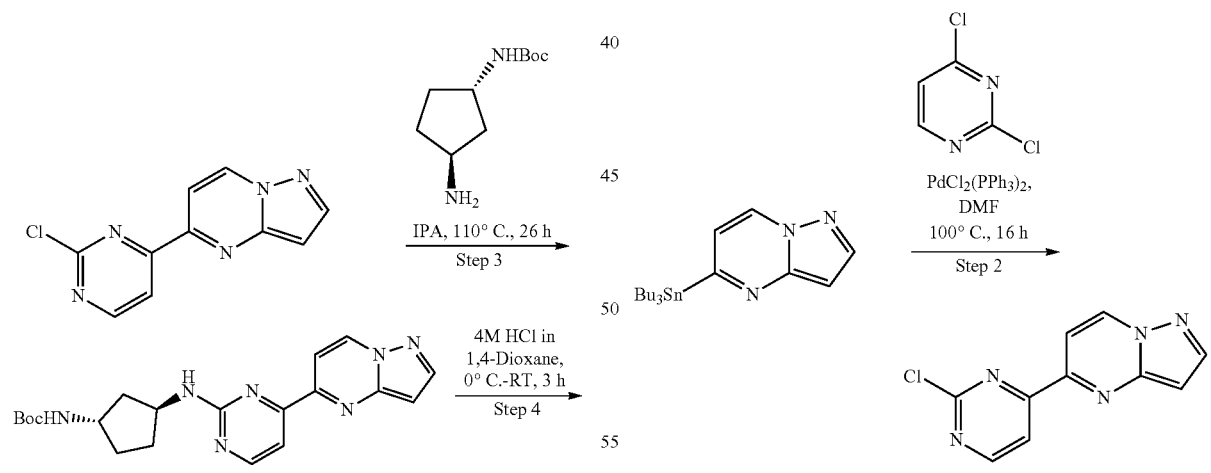

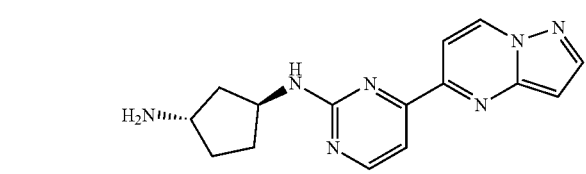

To a stirred solution of 5-(tributylstannyl)pyrazolo[1,5-a]pyrimidine (700 mg, 1.71 mmol, 1 eq) and 2,4-dichloropyrimidine (305 mg, 2.05 mmol, 1.2eq) in DMF (14 mL) at room temperature was added Pd(dppf)Cl$_2$ (70 mg, 0.08 mmol, 0.05 eq.) and stirred at 100° C. for 16 h. After completion of reaction by TLC, diluted with water and extracted with ethyl acetate (2×70 mL). Organic layer was dried over anhydrous Na$_2$SO$_4$, evaporated and purified by silica (100-200 mesh) column (eluent: 0-30% EtOAc in Hexane) to afford 5-(2-chloropyrimidin-4-yl)pyrazolo[1,5- a]pyrimidine as yellow solid (110 mg, yield: 28%). TLC system: EtOAc:Hexanes (30:70), $R_f$ value: ~0.3; LCMS(m/z): 232.1 (M+H)+; $^1$H NMR (400 MHz, CDCl$_3$) δ: 8.83 (d, J=7.2 Hz, 1H), 8.81 (d, J=4.8 Hz, 1H), 8.41 (d, J=5.2 Hz, 1H), 8.24 (d, J=2.4 Hz, 1H), 8.03 (d, J=7.2 Hz, 1H), 6.86-6.85 (m, 1H).

Synthesis of tert-butyl ((1S,3S)-3-((4-(pyrazolo[1,5-a]pyrimidin-5-yl)pyrimidin-2-yl)amino)cyclopentyl)carbamate (Step 3)

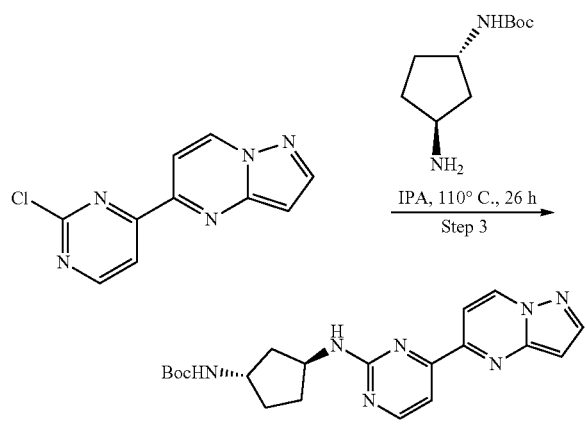

A solution of 5-(2-chloropyrimidin-4-yl)pyrazolo[1,5-a]pyrimidine (120 mg, 0.52 mmol, 1 eq) and tert-butyl((1S,3S)-3-aminocyclopentyl)carbamate (207 mg, 1.04 mmol, 2 eq) in isopropyl alcohol (2 mL) was stirred at 110° C. for 26 h. After completion of reaction by TLC, volatiles removed under vacuum, and the resultant mixture was diluted with water and extracted with ethyl acetate (2×30 mL). Organic layer was dried over anhydrous Na$_2$SO$_4$ and evaporated to afford tert-butyl((1S,3S)-3-((4-(pyrazolo[1,5-a]pyrimidin-5-yl)pyrimidin-2-yl)amino)cyclopentyl)carbamate as brown solid (130 mg). TLC system: EtOAc:Hexanes (50:50), $R_f$ value: ~0.3; LCMS(m/z): 396.2 (M+H)+.

Synthesis of (1S,3S)—N1-(4-(pyrazolo[1,5-a]pyrimidin-5-yl)pyrimidin-2-yl)cyclopentane-1,3-diamine (Step 4)

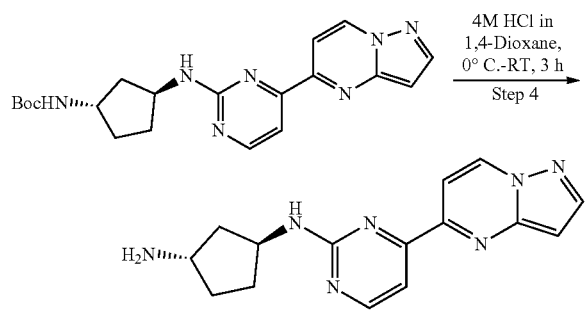

To a stirred solution of tert-butyl((1S,3S)-3-((4-(pyrazolo[1,5-a]pyrimidin-5-yl)pyrimidin-2-yl)amino)cyclopentyl)carbamate (130 mg, 0.33 mmol, 1 eq) in 1,4-dioxane (1.3 mL) at 0° C. was added 4M HCl in dioxane (0.75 mL, 1.5 vol) and stirred at room temperature for 3 h. After completion of reaction by TLC, reaction mixture was evaporated, diluted with sat. aq. NaHCO$_3$ solution and extracted with 20% methanol in DCM (3×20 mL). Organic layer was dried over anhydrous Na$_2$SO$_4$ and evaporated to afford (1S,3S)—N1-(4-(pyrazolo[1,5-a]pyrimidin-5-yl)pyrimidin-2-yl)cyclopentane-1,3-diamine as brown solid (40 mg, yield: 40%). TLC system: MeOH:DCM (5:95), $R_f$ value: ~0.2.

Biological Example 1

Cytotoxicity Assay

Multiplexing the LDH-Glo Cytotoxicity Assay and CellTiter-Glo 2D Cell Viability Assay. The RWPE-1 Normal Prostate Cells were treated with BLX-3030 and AZD-4573 in a 10-dose IC$_{50}$ mode in duplicate, with 3-fold serial dilution starting at 100 µM with 5000 cells/well in 96-well format for 72 hours. Change in toxicity was measured using the LDH-Glo Cytotoxicity Assay by combining 50 µL diluted samples with 50 µL LDH Detection Reagent and recording luminescence after 1 hour incubation. After samples were removed for LDH measurement, an equal volume of CellTiter Glo 2D Reagent was added to the remaining cell suspension and luminescence was recorded after 30-minute incubation period.

Biological Example 2

Cell Titer-Glo Assay

CellTiter-Glo® 2.0 Luminescent cell viability assay reagent was purchased from Promega and 22Rv1 and LASCPC-01 cell lines were purchased from ATCC. A test compound is dosed in 10-dose IC$_{50}$ mode in duplicate with 3-fold serial dilution starting at 100 µM with 4000 cells/well (adherent) in 96-well format and treatment time of 72 hours is used for all the chosen cell lines. An equal volume of CellTiter-Glo 2D Reagent is added to the cell suspensions and luminescence is recorded after 30-minute incubation period. Results can illustrate cellular antiproliferative efficacy of representative compound of Structure (I) in six prostate cancer cell lines over various concentrations.

Biological Example 3

Colony Formation Assay

Colony formation assay is performed on 2 Different NEPC Cell Lines. Cells are seeded at 800 cells per well in a 6-well plate and left to adhere for 24 hours in complete growth media. Treatment with a representative compound of Structure (I) ranges from NT to 10.0 µM for 14 days. Cells are fixed with a 3:1 methanol/acetic acid mixture and stained with methylene blue. SEM from two independent experiments. (*P<0.05,  P<0.01, * P<0.005 vs. DMSO control). The results can show that representative compounds of Structure (I) significantly inhibit the proliferation and colony formation of 22Rv1.

Biological Example 4

Annexin V/7-AAD Apoptosis Assay

Apoptosis induced by representative compounds of Structure (I) is assessed by Annexin V/7-AAD double staining and FACS analysis using a GUAVA Flow Cytometer. Representative compounds of Structure (I) treatments may increase apoptosis in a dose dependent manner. Real-time measurements of apoptosis induced by compounds of Structure (I) in prostate cancer cells are determined using IncuCyte S3 Live-Cell Analysis System. Additionally, apoptosis induced by representative compounds of Structure (I) is also assessed by Annexin V/7-AAD double staining and FACS analysis. Representative compounds of Structure (I) may increase apoptosis in a dose dependent manner according to the Annexin V/7-AAD staining results.

Biological Example 5

Western Blot

Two NEPC cell lines (22Rv1 & LASCPC-01) are treated with representative compounds of Structure (I) for 6 and 24 hours. Cytoplasmic and nuclear extracts from these cells are separated using NE-PER Nuclear and Cytoplasmic Extraction Kit (ThermoFisher). Cell extracts are separated on 4-12% Bis-Tris NuPAGE gel and then transferred onto 0.45 Nitrocellulose Membrane, followed by 30 min blocking with Pierce Fast Blocking Buffer, and then incubated overnight at 4° C. with indicated antibodies. Relative protein expression of CDK9, N-Myc, and other downstream signaling is quantified by GraphPad Prism 8 and ImageJ Software RT-PCR Gene.

Biological Example 6

Expression

Total RNA is extracted using RNeasy Mini Kit (Qiagen). cDNA is synthesized using iScript cDNA Synthesis Kit (Bio-Rad, Hercules, CA). Quantitative RT-PCR is performed with SsoAdvanced SYBR Green Supermix (Bio-Rad) on a CFX96 Real-Time PCR Detection System (Bio-Rad). Data is normalized to GUS and percentage of gene expression is determined by ΔCt method.

Biological Example 7

ADP-Glo Kinase Assay

ADP-Glo assay kit was purchased from Promega and the CDK9/CycT1 protein and PDKtide substrate were purchased from SignalChem. Compounds of Structure (I) are dosed in 10-dose $IC_{50}$ mode in duplicate with 3-fold serial dilution starting at 100 μM. The reaction is started by pre-incubating 4 μL of protein (20 nM), 2 μL of substrate (100 μM), and 2 μL of serial diluted drug in 1× assay buffer (50 mM HEPES, 3 mM $MgCl_2$, 3 mM $MnCl_2$, and 1 mM DTT) for 30 minutes. After pre-incubating, 4 μL of ATP (1 μM) is added to each well and incubated for an additional 90 minutes. The ADP-Glo Reagent (10 μL) and Kinase Detection Reagent (20 μL) are added to each well and incubated as recommended by Promega. The reaction is quantified by measuring luminescence and the $IC_{50}$ is calculated using GraphPad Prism software.

Biological Example 8

Immunofluorescence Staining

LASCPC-01 NEPC cells are treated with representative compounds of Structure (I) starting from NT, 1.1, 3.3 10, and 30 μM for 6 hours. After 6 hours, the cells are fixed with 4% formaldehyde and probed with primary N-Myc antibody overnight. The cells are then incubated with secondary antibody conjugated with Alexa Fluor 488 and counter-stained with Hoechst 33342. Images are taken with Nikon Automated Widefield CCD Camera and are quantified using ImageJ and GraphPad Prism 8 software.

Biological Example 9

Cell Cycle Arrest Assay

NEPC cells are treated with representative compounds of Structure (I) starting from NT, 1, and 3.16 μM for 8 hours. Then cells are harvested with PBS and fixed with ice-cold 70% ethanol at −20° C. overnight. The cells are then washed with ice-cold PBS 2× and then re-suspended in DAPI staining buffer and incubated in the dark for 30 minutes. The cells are analyzed using BD Fortessa flow cytometer and cell cycle distribution is analyzed using FlowJo and GraphPad Prism 8 Software. Western blot analysis of nuclear extract may show representative compounds of Structure (I) inhibited the CDK9 downstream targets. Blots from 22Rv1 and LASCPC-01 are used to show efficacy.

Biological Example 10

Cell Cycle Arrest Assay

Animals: Male BALB/c nude mice (8 week age). NEPC Cell lines: 22Rv1 & LASCPC-01. Number of cells: 22Rv1 ($1.2 \times 10^6$) & LASCPC-01 ($10^6$). Sub. Q. Tumor volume is measured two times per week by calipers and calculated by length×(width$^2$)/2. When tumors reached approximately 100-500 mm$^3$, mice are randomized and selected for treatment with representative compounds of Structure (I) (e.g., as a TFA, an HCl, or a formate salt) with 18-mg/kg oral dose.

Aspects of the embodiments can be modified, if necessary to employ concepts of the various patents, applications, and publications to provide yet further embodiments. These and other changes can be made to the embodiments considering the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

The invention claimed is:

1. A compound having the following Structure (I):

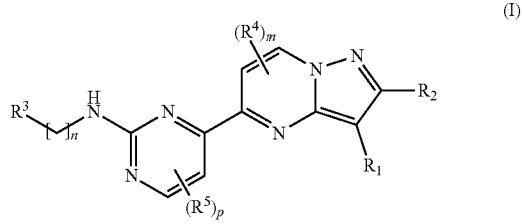

or a stereoisomer or salt thereof, wherein:
$R^1$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;
$R^2$ is hydrogen, halo, hydroxy, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;

R³ is 5-6 membered heterocyclyl;

each occurrence of R⁴ and R⁵ are independently halo, hydroxy, cyano, amino, $C_1$-$C_6$ alkyl, $C_3$-$C_8$ cycloalkyl, $C_1$-$C_6$ haloalkyl, $C_1$-$C_6$ alkoxy, or $C_1$-$C_6$ hydroxyalkyl;

m is 0, 1, or 2;

n is 0, 1, 2, 3, or 4; and p is 0, 1, or 2, wherein each R¹, R², R³, R⁴, and R⁵ is optionally substituted with one or more substituents.

2. The compound of claim 1, wherein R¹ is hydrogen, cyclopropyl, cyclobutyl, cyclopentyl, cyclohexyl, isopropyl, methyl, or ethyl.

3. The compound of claim 1, wherein R² is hydrogen or $C_1$-$C_6$ alkyl.

4. The compound of claim 1, wherein R² is —CH₃.

5. The compound of claim 1, wherein both of R¹ and R² are hydrogen.

6. The compound of claim 1, wherein n is 0 or 1.

7. The compound of claim 1, wherein R³ is unsubstituted or substituted with one or more substituents selected from the group consisting of hydroxy, amino, cyano, halo, $C_1$-$C_6$ alkyl, $C_3$-$C_8$ cycloalkyl, $C_1$-$C_6$ haloalkyl, or —N(R$^{3b}$)R$^{3a}$, wherein:

$R^{3a}$ is —C(=O)alkyl, 3-10 membered heterocyclyl, or 3-10 membered heteroaryl; and $R^{3b}$ is hydrogen or $C_1$-$C_6$ alkyl.

8. The compound of claim 1, wherein R³ has one of the following structures:

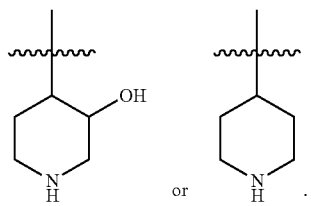 [SMILES: *C1CCNCC1O ; *C1CCNCC1]

9. The compound claim 1, wherein R³ has one of the following structures:

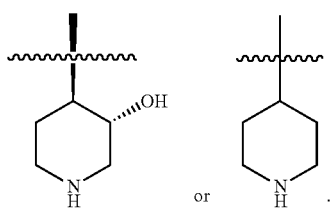

10. The compound of claim 1, wherein m is 1 or 2 and each occurrence of R⁴ is halo.

11. The compound of claim 1, wherein each occurrence of R⁴ is fluoro.

12. The compound of claim 1, wherein p is 0.

13. The compound of claim 1, wherein p is 1 and R⁵ is chloro.

14. The compound of claim 1, wherein the compound has one of the following structures:

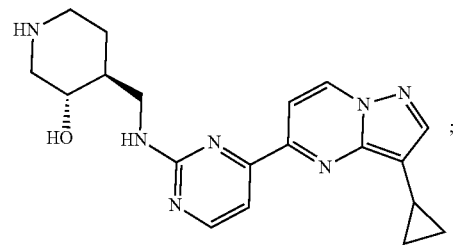

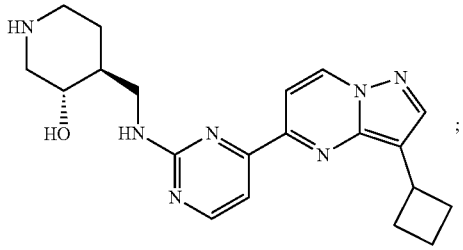

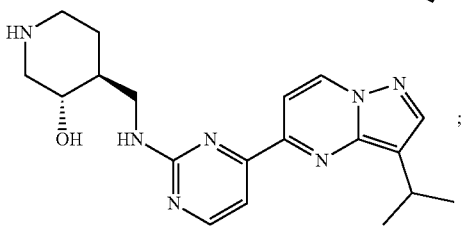

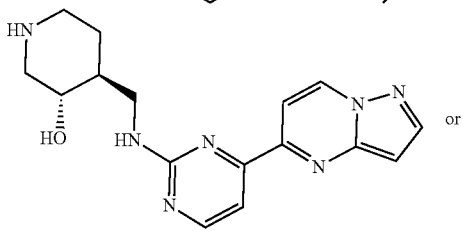

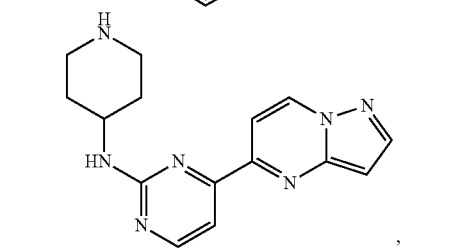

or a salt thereof.

15. The compound of claim 1, wherein the compound is a free base form.

16. The compound of claim 1, wherein the compound is a pharmaceutically acceptable salt.

17. The compound of claim 1, wherein the compound is a trifluoroacetic acid salt, a hydrochloric acid salt, or a formic acid salt.

18. A pharmaceutical composition comprising a compound or salt of claim 1 and a pharmaceutically acceptable carrier.

19. A method for treating bladder cancer, prostate cancer, or acute myeloid leukemia, or an inflammatory disease, the method comprising administering an effective amount of the compound of claim 1 to a subject in need thereof.

* * * * *

UNITED STATES PATENT AND TRADEMARK OFFICE
CERTIFICATE OF CORRECTION

PATENT NO. : 12,275,738 B2
APPLICATION NO. : 18/296930
DATED : April 15, 2025
INVENTOR(S) : Hariprasad Vankayalapati et al.

Page 1 of 1

It is certified that error appears in the above-identified patent and that said Letters Patent is hereby corrected as shown below:

In the Claims

Column 98, Claim 19, Line 59:
"myeloid leukemia, or an inflammatory disease, the" should read: -- myeloid leukemia, the --.

Signed and Sealed this
Fifteenth Day of July, 2025

Coke Morgan Stewart
*Acting Director of the United States Patent and Trademark Office*